United States Patent
Ramseier et al.

(10) Patent No.: US 10,323,261 B2
(45) Date of Patent: Jun. 18, 2019

(54) POLYHYDROXYALKANOATE COPOLYMER COMPOSITIONS AND METHODS OF MAKING THE SAME

(71) Applicant: CJ CheilJedang Corporation, Seoul (KR)

(72) Inventors: Thomas Martin Ramseier, Newton, MA (US); Jeffrey A. Bickmeier, Arlington, MA (US); William R. Farmer, Concord, MA (US); Catherine Morse, Melrose, MA (US); Himani Chinnapen, Quincy, MA (US); Oliver P. Peoples, Arlington, MA (US); Yossef Shabtai, Concord, MA (US)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 15/785,845

(22) Filed: Oct. 17, 2017

(65) Prior Publication Data
US 2018/0057848 A1 Mar. 1, 2018

Related U.S. Application Data

(62) Division of application No. 14/434,651, filed as application No. PCT/US2013/062812 on Oct. 1, 2013.

(60) Provisional application No. 61/734,489, filed on Dec. 7, 2012, provisional application No. 61/711,825, filed on Oct. 10, 2012.

(51) Int. Cl.
*C12P 7/62* (2006.01)
*C08G 63/06* (2006.01)
*C08L 67/04* (2006.01)

(52) U.S. Cl.
CPC .............. *C12P 7/625* (2013.01); *C08G 63/06* (2013.01); *C08L 67/04* (2013.01); *C08L 2201/06* (2013.01)

(58) Field of Classification Search
CPC ...... C12P 7/625; C08L 67/04; C08L 2201/06; C08G 63/06; C08G 63/08
See application file for complete search history.

(56) References Cited

U.S. PATENT DOCUMENTS

| | | | |
|---|---|---|---|
| 6,117,658 | A | 9/2000 | Dennis et al. |
| 6,316,262 | B1 | 11/2001 | Huisman et al. |
| 2010/0168481 | A1 | 7/2010 | Farmer et al. |
| 2011/0319849 | A1 | 12/2011 | Collias et al. |
| 2012/0149844 | A1 | 6/2012 | Whitehouse |
| 2012/0214213 | A1 | 8/2012 | Chen et al. |
| 2013/0034884 | A1 | 2/2013 | Burgard et al. |

FOREIGN PATENT DOCUMENTS

| | | |
|---|---|---|
| CN | 104379671 A | 2/2015 |
| WO | 2011031558 A2 | 3/2011 |
| WO | 2011100601 A1 | 8/2011 |
| WO | 2013184822 A2 | 12/2013 |
| WO | 2013184836 A1 | 12/2013 |

OTHER PUBLICATIONS

Amirul, et al., Improved production of poly (3-hydroxybutyrate-co-4-hydroxbutyrate) copolymer using a combination of 1,4-butanediol and y-butyrolactone, World Journal of Microbiol Biotechnol, 2010, vol. 26, pp. 743-746.
Li, et al., Production of poly(3-hydroxybutyrate-co-4-hydroxybutyrate) from unrelated carbon sources by metabolically engineered *Escherichia coli*, Metabolic Engineering, 2010, vol. 12, pp. 352-359.
Lee, W.H., et al., Magnesium affects poly(3-hydroxybutyrate-co-4-hydroxybutyrate) content and composition by affecting glucose uptake in Delftia acidovorans, Malaysian Journal of Microbiology, 2007, vol. 3(1), pp. 31-34.
Park, Dae Hoo, et al., Production of poly(3-hydroxybutyrate) and poly(3-hydroxybutyrate-co-4-hydroxybutyrate) by Ralstonia eutropha from soybean oil, New Biotechnology, 2011, vol. 38, No. 6, pp. 719-724.
Chanprateep, Suchada, et al., Biosynthesis and biocompatibility of biodegradable poly(3-hydroxybutyrate-co-4-hydroxybutyrate) Polymer Degradation and Stability, 2010, vol. 95, pp. 2003-2012.
Roa, et al., Biosynthesis and biocompatibility of poly( 3-hydroxybutyrate-co-4-hydroxybutyrate) produced by Cupriavidus necator from spent palm oil, Biochemical Engineering Journal, 2010, vol. 49, pp. 13-20.
Hsieh, et al., Fermentation, biodegradation and tensile strength of poly(3-hydroxybutyrate-co-4-hydroxybutyrate) synthesized by Delftia acidovorans, Journal of the Taiwan Institute of Chemkal Engineers, 2009, vol. 40, pp. 143-147.

(Continued)

*Primary Examiner* — Robert S Jones
(74) *Attorney, Agent, or Firm* — Pearne & Gordon LLP

(57) ABSTRACT

A polyhydroxyalkanoate copolymer composition is provided. The composition comprises a plurality of polyhydroxyalkanoate copolymer molecules. The polyhydroxyalkanoate copolymer molecules (i) comprise 3-hydroxybutyrate monomers and 4-hydroxybutyrate monomers, (ii) have a monomeric molar percentage of 4-hydroxybutyrate monomers of 23.5 to 75%, and (iii) have a biobased content of ≥80%. Also provided is a method of making a polyhydroxyalkanoate copolymer composition. The method comprises culturing an organism in the presence of one or more carbon raw materials under conditions under which (a) the one or more carbon raw materials are converted to 3-hydroxybutyryl-CoA and 4-hydroxybutyryl-CoA and (b) the 3-hydroxybutyryl-CoA and the 4-hydroxybutyryl-CoA are polymerized to form the polyhydroxyalkanoate copolymer molecules, thereby forming the composition. The organism has been genetically engineered to comprise particular enzymatic activities, and to not comprise other particular enzymatic activities. The one or more carbon raw materials, taken together, have a biobased content of ≥80%.

14 Claims, 1 Drawing Sheet
Specification includes a Sequence Listing.

(56) References Cited

OTHER PUBLICATIONS

Amirul, et al., Biosynthesis of poly(3-hydroxybutyrate-co-4-hydroxybutyrate) copolymer by *Cupriavidus* sp. USMAA1020 isolated from Lake Kulim, Malaysia, Bioresource Technology, 2008, vol. 99, pp. 4903-4909.

Zhou, et al., Hyperproduction of poly(4-hydroxybutyrate from glucose by recombiant *Escherichia coli*, Microbial Cell Factories, 2012, 11:54, pp. 1-8.

Bioplastics Counsel, Understanding biobased carbon content; Society of the Plastics Industry, Feb. 2012, cover page, copyright page, and pp. 1-12, URL: http://www.plasticsindustry.org/files/about/BPC/Understanding%20Biobased%20Content%20-%2002120Date%20-%20FINAL.pdf.

Hasunuma, et al., Effect of DNA Mutations on the Replication of Plasmid pSCIOI in *Escherichia coli* K-12, Journal of Bacteriology, 1979, vol. 137, No. 3, pp. 1095-1099.

Lenski, et al. Effects of Segregation and Selection on Instability of Plasmid pACYC184 in *Escherichia coli* B, Journal of Bacteriology, 1987, vol. 169, No. 11, pp. 5314-5316.

Martinez-Morales, et al., Chromosomal Integration of Heterologous DNA in *Escherichia coli* with Precise Removal of Markers and Replicons Used during Construction, Journal of Bacteriology, 1999, vol. 181, No. 22, pp. 7143-7148.

Green, R., Current Strategies for Optimizing Polyhydroxyalkanoate Production in Bacterial Systems, MMG 445 Basic Biotech eJournal 2010 6:1, Dec. 14, 2010, pp. 1-6, URL: http://ejournal.vudat.msu.edu/index.php/mmg445/article/viewArticle/MMG45.4573055/394.

Smith, et al., Bacterial fitness and plasmid loss: the importance of culture conditions and plasmid size, Canadian Journal of Microbiology, 1998, vol. 44, pp. 351-355.

Designation: D6866-12, Standard Test Methods for Determining the Biobased Content of Solid, Liquid, and Gaseous Samples Using Radiocarbon Analysis; ASTM International, ANSI order X_289041, Apr. 1, 2012, pp. 1-14.

Yim, et al., Metabolic_engineering of *Escherichia coli* for direct production of 1,4-butanediol, Nature Chemical Biology 2011, vol. 7, pp. 445-452.

Chinese Office action issued in application No. 201380052531.9, dated Dec. 5, 2016.

International Preliminary Report on Patentability issued in application No. PCT/US2013/062812, dated Dec. 5, 2014.

International Search Report and Written Opinion issued in application No. PCT/US2013/062812, dated Feb. 6, 2014.

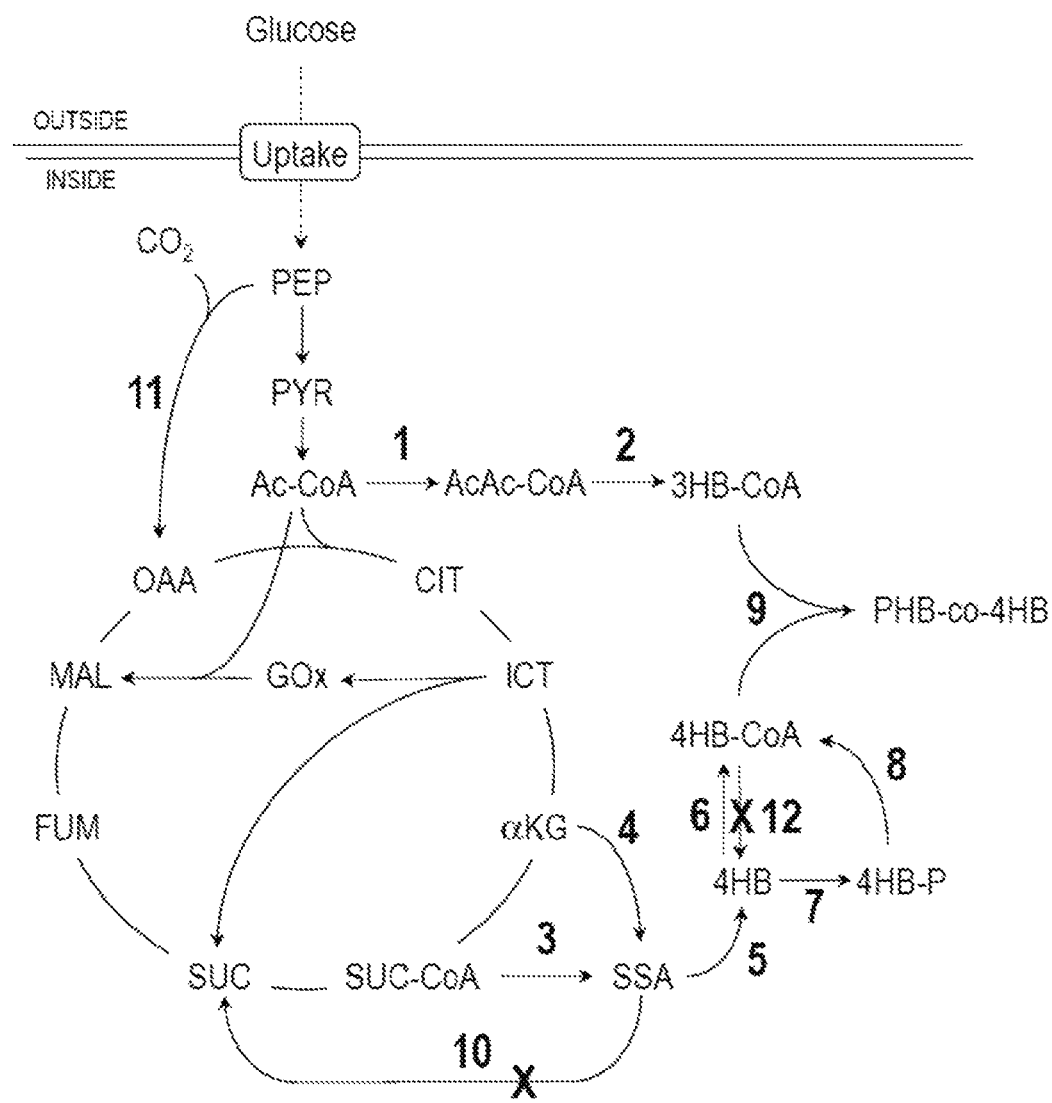

```
                          SEQUENCE LISTING

<160> NUMBER OF SEQ ID NOS: 27

<210> SEQ ID NO 1
<211> LENGTH: 35
<212> TYPE: DNA
<213> ORGANISM: Artificial Sequence
<220> FEATURE:
<223> OTHER INFORMATION: PsynA promoter

<400> SEQUENCE: 1
ttgacagcta gctcagtcct aggtataatg ctagc                                35

<210> SEQ ID NO 2
<211> LENGTH: 35
<212> TYPE: DNA
<213> ORGANISM: Artificial Sequence
<220> FEATURE:
<223> OTHER INFORMATION: PsynC promoter

<400> SEQUENCE: 2
ttgacagcta gctcagtcct aggtactgtg ctagc                                35

<210> SEQ ID NO 3
<211> LENGTH: 35
<212> TYPE: DNA
<213> ORGANISM: Artificial Sequence
<220> FEATURE:
<223> OTHER INFORMATION: PsynE promoter

<400> SEQUENCE: 3
tttacagcta gctcagtcct aggtattatg ctagc                                35

<210> SEQ ID NO 4
<211> LENGTH: 35
<212> TYPE: DNA
<213> ORGANISM: Artificial Sequence
<220> FEATURE:
<223> OTHER INFORMATION: PsynH promoter

<400> SEQUENCE: 4
ctgacagcta gctcagtcct aggtataatg ctagc                                35

<210> SEQ ID NO 5
<211> LENGTH: 35
<212> TYPE: DNA
<213> ORGANISM: Artificial Sequence
<220> FEATURE:
<223> OTHER INFORMATION: PsynK promoter

<400> SEQUENCE: 5
tttacggcta gctcagtcct aggtacaatg ctagc                                35
```

<210> SEQ ID NO 6
<211> LENGTH: 35
<212> TYPE: DNA
<213> ORGANISM: Artificial Sequence
<220> FEATURE:
<223> OTHER INFORMATION: PsynM promoter

<400> SEQUENCE: 6
ttgacagcta gctcagtcct agggactatg ctagc                                35

<210> SEQ ID NO 7
<211> LENGTH: 31
<212> TYPE: DNA
<213> ORGANISM: Artificial Sequence
<220> FEATURE:
<223> OTHER INFORMATION: Px promoter

<400> SEQUENCE: 7
tcgccagtct ggcctgaaca tgatataaaa t                                    31

<210> SEQ ID NO 8
<211> LENGTH: 178
<212> TYPE: DNA
<213> ORGANISM: Artificial Sequence
<220> FEATURE:
<223> OTHER INFORMATION: PuspA promoter

<400> SEQUENCE: 8
aaccactatc aatatattca tgtcgaaaat ttgtttatct aacgagtaag caaggcggat      60
tgacggatca tccgggtcgc tataaggtaa ggatggtctt aacactgaat ccttacggct    120
gggttagccc cgcgcacgta gttcgcagga cgcgggtgac gtaacggcac aagaaacg     178

<210> SEQ ID NO 9
<211> LENGTH: 170
<212> TYPE: DNA
<213> ORGANISM: Artificial Sequence
<220> FEATURE:
<223> OTHER INFORMATION: PrpsU promoter

<400> SEQUENCE: 9
atgcgggttg atgtaaaact ttgttcgccc ctggagaaag cctcgtgtat actcctcacc     60
cttataaaag tcccttttcaa aaaaggccgc ggtgctttac aaagcagcag caattgcagt  120
aaaattccgc accatttttga ataagctgg cgttgatgcc agcggcaaac                170

<210> SEQ ID NO 10
<211> LENGTH: 35
<212> TYPE: DNA
<213> ORGANISM: Artificial Sequence
<220> FEATURE:
<223> OTHER INFORMATION: PsynAF7 promoter

<400> SEQUENCE: 10
ttgacagcta gctcagtcct aggtacagtg ctagc                                35

<210> SEQ ID NO 11
<211> LENGTH: 35
<212> TYPE: DNA
<213> ORGANISM: Artificial Sequence
<220> FEATURE:
<223> OTHER INFORMATION: PsynAF3 promoter

<400> SEQUENCE: 11
ttgacagcta gctcagtcct aggtacaatg ctagc    35

<210> SEQ ID NO 12
<211> LENGTH: 29
<212> TYPE: DNA
<213> ORGANISM: Artificial Sequence
<220> FEATURE:
<223> OTHER INFORMATION: TtrpL terminator

<400> SEQUENCE: 12
ctaatgagcg ggcttttttt tgaacaaaa    29

<210> SEQ ID NO 13
<211> LENGTH: 38
<212> TYPE: DNA
<213> ORGANISM: Artificial Sequence
<220> FEATURE:
<223> OTHER INFORMATION: T1006 terminator

<400> SEQUENCE: 13
aaaaaaaaaa aacccccgctt cggcggggtt tttttttt    38

<210> SEQ ID NO 14
<211> LENGTH: 44
<212> TYPE: DNA
<213> ORGANISM: Artificial Sequence
<220> FEATURE:
<223> OTHER INFORMATION: TrrnB1 terminator

<400> SEQUENCE: 14
ataaaacgaa aggctcagtc gaaagactgg gcctttcgtt ttat    44

<210> SEQ ID NO 15
<211> LENGTH: 28
<212> TYPE: DNA
<213> ORGANISM: Artificial Sequence
<220> FEATURE:
<223> OTHER INFORMATION: TrrnB2 terminator

<400> SEQUENCE: 15
agaaggccat cctgacggat ggcctttt    28

<210> SEQ ID NO 16
<211> LENGTH: 1362
<212> TYPE: DNA
<213> ORGANISM: Clostridium kluyveri

<400> SEQUENCE: 16
atgtccaacg aggttagcat taaggagctg attgagaagg cgaaagtggc gcagaaaaag    60
ctggaagcgt atagccaaga gcaagttgac gttctggtca aggcgctggg taaagttgtg    120
tacgacaacg ccgagatgtt cgcgaaagag gcggtggagg aaaccgagat gggtgtttac    180
gaggataaag tggctaaatg tcatctgaaa tctggtgcaa tctggaatca cattaaagat    240
aagaaaaccg ttggtattat caaggaagaa ccggagcgtg cgctggtgta cgtcgcgaag    300
cctaaaggtg ttgtggcggc gacgaccccct atcaccaatc ctgtggttac cccgatgtgt    360
aacgcgatgg cagcaattaa agtcgcaac accatcattg tcgccccgca tccgaaggcg    420
aagaaggtga gcgcgcacac cgtggagctg atgaatgcag aactgaaaaa gttgggtgcg    480
ccggaaaaca ttatccagat cgttgaagcc ccaagccgtg aagcagccaa ggagttgatg    540
gagagcgcag acgtggttat cgccacgggt ggcgcaggcc gtgttaaagc agcgtactcc    600
tccggccgtc cggcatacgg tgtcggtccg ggcaattctc aggtcattgt cgataagggt    660

-continued

```
tacgattata acaaagctgc ccaggacatc attaccggcc gcaagtatga caacggtatc     720
atttgcagct ctgagcagag cgtgatcgca ccggcggagg actacgacaa ggtcatcgcg     780
gctttcgtcg agaatggcgc gttctatgtc gaggatgagg aaactgtgga gaaattccgt     840
agcacgctgt tcaaggatgg caagatcaat agcaaaatca tcggtaaatc cgtgcagatc     900
atcgctgacc tggctggtgt caaggtgccg gaaggcacca aggtgatcgt gttgaagggc     960
aagggtgccg gtgaaaagga cgttctgtgc aaggagaaaa tgtgcccggt cctggttgcc    1020
ctgaaatatg acacctttga ggaggcggtc gagatcgcga tggccaacta tatgtacgag    1080
ggtgcgggcc ataccgccgg tatccacagc gataacgacg agaatatccg ctacgcgggt    1140
acggtgctgc aatcagccg tctggttgtc aaccagccag caactacggc cggtggtagc    1200
tttaacaatg gttttaatcc gaccaccacc ttgggctgcg gtagctgggg ccgtaactcc    1260
attagcgaga acctgacgta tgagcatctg attaatgtca gccgtattgg ctatttcaat    1320
aaggaggcaa agttcctag ctacgaggag atctggggtt aa                        1362
```

<210> SEQ ID NO 17
<211> LENGTH: 453
<212> TYPE: PRT
<213> ORGANISM: Clostridium kluyveri

<400> SEQUENCE: 17

```
Met Ser Asn Glu Val Ser Ile Lys Glu Leu Ile Glu Lys Ala Lys Val
1               5                   10                  15

Ala Gln Lys Lys Leu Glu Ala Tyr Ser Gln Glu Gln Val Asp Val Leu
            20                  25                  30

Val Lys Ala Leu Gly Lys Val Val Tyr Asp Asn Ala Glu Met Phe Ala
        35                  40                  45

Lys Glu Ala Val Glu Glu Thr Glu Met Gly Val Tyr Glu Asp Lys Val
    50                  55                  60

Ala Lys Cys His Leu Lys Ser Gly Ala Ile Trp Asn His Ile Lys Asp
65                  70                  75                  80

Lys Lys Thr Val Gly Ile Ile Lys Glu Glu Pro Glu Arg Ala Leu Val
                85                  90                  95

Tyr Val Ala Lys Pro Lys Gly Val Val Ala Ala Thr Thr Pro Ile Thr
            100                 105                 110

Asn Pro Val Val Thr Pro Met Cys Asn Ala Met Ala Ala Ile Lys Gly
        115                 120                 125

Arg Asn Thr Ile Ile Val Ala Pro His Pro Lys Ala Lys Lys Val Ser
    130                 135                 140

Ala His Thr Val Glu Leu Met Asn Ala Glu Leu Lys Lys Leu Gly Ala
145                 150                 155                 160

Pro Glu Asn Ile Ile Gln Ile Val Glu Ala Pro Ser Arg Glu Ala Ala
                165                 170                 175

Lys Glu Leu Met Glu Ser Ala Asp Val Val Ile Ala Thr Gly Gly Ala
            180                 185                 190

Gly Arg Val Lys Ala Ala Tyr Ser Ser Gly Arg Pro Ala Tyr Gly Val
        195                 200                 205

Gly Pro Gly Asn Ser Gln Val Ile Val Asp Lys Gly Tyr Asp Tyr Asn
    210                 215                 220

Lys Ala Ala Gln Asp Ile Ile Thr Gly Arg Lys Tyr Asp Asn Gly Ile
225                 230                 235                 240

Ile Cys Ser Ser Glu Gln Ser Val Ile Ala Pro Ala Glu Asp Tyr Asp
```

```
                245                 250                 255
Lys Val Ile Ala Ala Phe Val Glu Asn Gly Ala Phe Tyr Val Glu Asp
            260                 265                 270

Glu Glu Thr Val Glu Lys Phe Arg Ser Thr Leu Phe Lys Asp Gly Lys
        275                 280                 285

Ile Asn Ser Lys Ile Ile Gly Lys Ser Val Gln Ile Ala Asp Leu
    290                 295                 300

Ala Gly Val Lys Val Pro Glu Gly Thr Lys Val Ile Val Leu Lys Gly
305                 310                 315                 320

Lys Gly Ala Gly Glu Lys Asp Val Leu Cys Lys Glu Lys Met Cys Pro
                325                 330                 335

Val Leu Val Ala Leu Lys Tyr Asp Thr Phe Glu Glu Ala Val Glu Ile
            340                 345                 350

Ala Met Ala Asn Tyr Met Tyr Glu Gly Ala Gly His Thr Ala Gly Ile
            355                 360                 365

His Ser Asp Asn Asp Glu Asn Ile Arg Tyr Ala Gly Thr Val Leu Pro
        370                 375                 380

Ile Ser Arg Leu Val Val Asn Gln Pro Ala Thr Thr Ala Gly Gly Ser
385                 390                 395                 400

Phe Asn Asn Gly Phe Asn Pro Thr Thr Thr Leu Gly Cys Gly Ser Trp
                405                 410                 415

Gly Arg Asn Ser Ile Ser Glu Asn Leu Thr Tyr Glu His Leu Ile Asn
            420                 425                 430

Val Ser Arg Ile Gly Tyr Phe Asn Lys Glu Ala Lys Val Pro Ser Tyr
        435                 440                 445

Glu Glu Ile Trp Gly
    450

<210> SEQ ID NO 18
<211> LENGTH: 870
<212> TYPE: DNA
<213> ORGANISM: Arabidopsis thaliana

<400> SEQUENCE: 18
atggaagtag gttttctggg tctgggcatt atgggtaaag ctatgtccat gaacctgctg      60
aaaaacggtt tcaaagttac cgtgtggaac cgcactctgt ctaaatgtga tgaactggtt     120
gaacacggtg caagcgtgtg cgagtctccg gctgaggtga tcaagaaatg caaatacacg     180
atcgcgatgc tgagcgatcc gtgtgcagct ctgtctgttg ttttcgataa aggcggtgtt     240
ctggaacaga tctgcgaggg taagggctac atcgacatgt ctaccgtcga cgcggaaact     300
agcctgaaaa ttaacgaagc gatcacgggc aaaggtggcc gttttgtaga aggtcctgtt     360
agcggttcca aaaagccggc agaagacggc agctgatca tcctggcagc aggcgacaaa     420
gcactgttcg aggaatccat cccggccttt gatgtactgg caaacgttc cttttatctg     480 ggtcaggtgg gtaacggtgc gaaaatgaaa ctgattgtta acatgatcat gggttctatg     540
atgaacgcgt ttagcgaagg tctggtactg gcagataaaa gcggtctgtc tagcgacacg     600
ctgctggata ttctggatct gggtgctatg acgaatccga tgttcaaagg caaaggtccg     660
tccatgacta aatccagcta cccaccggct ttcccgctga acaccagca gaaagacatg     720 cgtctggctc tggctctggg cgacgaaaac gctgttagca tgccggtcgc tgcggctgcg     780
aacgaagcct tcaagaaagc ccgtagcctg ggcctgggcg atctggactt ttctgctgtt     840
atcgaagcgg taaaattctc tcgtgaataa                                      870
```

<210> SEQ ID NO 19
<211> LENGTH: 289
<212> TYPE: PRT
<213> ORGANISM: Arabidopsis thaliana

<400> SEQUENCE: 19

Met Glu Val Gly Phe Leu Gly Leu Gly Ile Met Gly Lys Ala Met Ser
1               5                   10                  15

Met Asn Leu Leu Lys Asn Gly Phe Lys Val Thr Val Trp Asn Arg Thr
            20                  25                  30

Leu Ser Lys Cys Asp Glu Leu Val Glu His Gly Ala Ser Val Cys Glu
        35                  40                  45

Ser Pro Ala Glu Val Ile Lys Lys Cys Lys Tyr Thr Ile Ala Met Leu
    50                  55                  60

Ser Asp Pro Cys Ala Ala Leu Ser Val Val Phe Asp Lys Gly Gly Val
65                  70                  75                  80

Leu Glu Gln Ile Cys Glu Gly Lys Gly Tyr Ile Asp Met Ser Thr Val
                85                  90                  95

Asp Ala Glu Thr Ser Leu Lys Ile Asn Glu Ala Ile Thr Gly Lys Gly
            100                 105                 110

Gly Arg Phe Val Glu Gly Pro Val Ser Gly Ser Lys Lys Pro Ala Glu
        115                 120                 125

Asp Gly Gln Leu Ile Ile Leu Ala Ala Gly Asp Lys Ala Leu Phe Glu
    130                 135                 140

Glu Ser Ile Pro Ala Phe Asp Val Leu Gly Lys Arg Ser Phe Tyr Leu
145                 150                 155                 160

Gly Gln Val Gly Asn Gly Ala Lys Met Lys Leu Ile Val Asn Met Ile
                165                 170                 175

Met Gly Ser Met Met Asn Ala Phe Ser Glu Gly Leu Val Leu Ala Asp
            180                 185                 190

Lys Ser Gly Leu Ser Ser Asp Thr Leu Leu Asp Ile Leu Asp Leu Gly
        195                 200                 205

Ala Met Thr Asn Pro Met Phe Lys Gly Lys Gly Pro Ser Met Thr Lys
    210                 215                 220

Ser Ser Tyr Pro Pro Ala Phe Pro Leu Lys His Gln Gln Lys Asp Met
225                 230                 235                 240

Arg Leu Ala Leu Ala Leu Gly Asp Glu Asn Ala Val Ser Met Pro Val
                245                 250                 255

Ala Ala Ala Ala Asn Glu Ala Phe Lys Lys Ala Arg Ser Leu Gly Leu
            260                 265                 270

Gly Asp Leu Asp Phe Ser Ala Val Ile Glu Ala Val Lys Phe Ser Arg
        275                 280                 285

Glu

<210> SEQ ID NO 20
<211> LENGTH: 1152
<212> TYPE: DNA
<213> ORGANISM: Escherichia coli

<400> SEQUENCE: 20
atgatggcta acagaatgct ggtgaacgaa acggcatggt ttggtcgggg tgctgttggg      60
gctttaaccg atgaggtgaa acgccgtggt tatcagaagg cgctgatcgt caccgataaa     120
acgctggtgc aatgcggcgt ggtggcgaaa gtgaccgata agatggatgc tgcagggctg     180
gcatgggcga tttacgacgg cgtagtgccc aacccaacaa ttactgtcgt caaagaaggg     240

```
ctcggtgtat tccagaatag cggcgcggat tacctgatcg ctattggtgg tggttctcca    300
caggatactt gtaaagcgat tggcattatc agcaacaacc cggagtttgc cgatgtgcgt    360
agcctggaag ggctttcccc gaccaataaa cccagtgtac cgattctggc aattcctacc    420
acagcaggta ctgcggcaga agtgaccatt aactacgtga tcactgacga agagaaacgg    480
cgcaagtttg tttgcgttga tccgcatgat atcccgcagg tggcgtttat tgacgctgac    540
atgatggatg gtatgcctcc agcgctgaaa gctgcgacgg tgtcgatgc gctcactcat    600 gctattgagg ggtatattac ccgtggcgcg tgggcgctaa ccgatgcact gcacattaaa    660
gcgattgaaa tcattgctgg ggcgctgcga ggatcggttg ctggtgataa ggatgccgga    720
gaagaaatgg cgctcgggca gtatgttgcg ggtatgggct ctcgaatgt tgggttaggg    780 ttggtgcatg gtatggcgca tccactgggc gcgttttata acactccaca cggtgttgcg    840
aacgccatcc tgttaccgca tgtcatgcgt tataacgctg actttaccgg tgagaagtac    900
cgcgatatcg cgcgcgttat gggcgtgaaa gtggaaggta tgagcctgga agaggcgcgt    960
aatgccgctg ttgaagcggt gtttgctctc aaccgtgatg tcggtattcc gccacatttg   1020
cgtgatgttg gtgtacgcaa ggaagacatt ccggcactgg cgcaggcggc actggatgat   1080
gtttgtaccg gtggcaaccc gcgtgaagca acgcttgagg atattgtaga gctttaccat   1140
accgcctggt aa                                                        1152

<210> SEQ ID NO 21
<211> LENGTH: 382
<212> TYPE: PRT
<213> ORGANISM: Escherichia coli

<400> SEQUENCE: 21

Met Ala Asn Arg Met Leu Val Asn Glu Thr Ala Trp Phe Gly Arg Gly
1               5                   10                  15

Ala Val Gly Ala Leu Thr Asp Glu Val Lys Arg Arg Gly Tyr Gln Lys
            20                  25                  30

Ala Leu Ile Val Thr Asp Lys Thr Leu Val Gln Cys Gly Val Val Ala
        35                  40                  45

Lys Val Thr Asp Lys Met Asp Ala Ala Gly Leu Ala Trp Ala Ile Tyr
    50                  55                  60

Asp Gly Val Val Pro Asn Pro Thr Ile Thr Val Lys Glu Gly Leu
65                  70                  75                  80

Gly Val Phe Gln Asn Ser Gly Ala Asp Tyr Leu Ile Ala Ile Gly Gly
            85                  90                  95

Gly Ser Pro Gln Asp Thr Cys Lys Ala Ile Gly Ile Ile Ser Asn Asn
        100                 105                 110

Pro Glu Phe Ala Asp Val Arg Ser Leu Glu Gly Leu Ser Pro Thr Asn
    115                 120                 125

Lys Pro Ser Val Pro Ile Leu Ala Ile Pro Thr Thr Ala Gly Thr Ala
    130                 135                 140

Ala Glu Val Thr Ile Asn Tyr Val Ile Thr Asp Glu Glu Lys Arg Arg
145                 150                 155                 160

Lys Phe Val Cys Val Asp Pro His Asp Ile Pro Gln Val Ala Phe Ile
                165                 170                 175

Asp Ala Asp Met Met Asp Gly Met Pro Pro Ala Leu Lys Ala Ala Thr
            180                 185                 190

Gly Val Asp Ala Leu Thr His Ala Ile Glu Gly Tyr Ile Thr Arg Gly
        195                 200                 205
```

Ala Trp Ala Leu Thr Asp Ala Leu His Ile Lys Ala Ile Glu Ile Ile
    210                 215                 220

Ala Gly Ala Leu Arg Gly Ser Val Ala Gly Asp Lys Asp Ala Gly Glu
225                 230                 235                 240

Glu Met Ala Leu Gly Gln Tyr Val Ala Gly Met Gly Phe Ser Asn Val
                245                 250                 255

Gly Leu Gly Leu Val His Gly Met Ala His Pro Leu Gly Ala Phe Tyr
            260                 265                 270

Asn Thr Pro His Gly Val Ala Asn Ala Ile Leu Leu Pro His Val Met
        275                 280                 285

Arg Tyr Asn Ala Asp Phe Thr Gly Glu Lys Tyr Arg Asp Ile Ala Arg
    290                 295                 300

Val Met Gly Val Lys Val Glu Gly Met Ser Leu Glu Glu Ala Arg Asn
305                 310                 315                 320

Ala Ala Val Glu Ala Val Phe Ala Leu Asn Arg Asp Val Gly Ile Pro
                325                 330                 335

Pro His Leu Arg Asp Val Gly Val Arg Lys Glu Asp Ile Pro Ala Leu
            340                 345                 350

Ala Gln Ala Ala Leu Asp Asp Val Cys Thr Gly Gly Asn Pro Arg Glu
        355                 360                 365

Ala Thr Leu Glu Asp Ile Val Glu Leu Tyr His Thr Ala Trp
    370                 375                 380

<210> SEQ ID NO 22
<211> LENGTH: 1680
<212> TYPE: DNA
<213> ORGANISM: Artificial Sequence
<220> FEATURE:
<223> OTHER INFORMATION: phaC3/C5 fusion

<400> SEQUENCE: 22
atgagtaaca agaacaacga tgagctgcag tggcaatcct ggttcagcaa ggcgcccacc        60
accgaggcga acccgatggc caccatgttg caggatatcg gcgttgcgct caaaccggaa       120
gcgatggagc agctgaaaaa cgattatctg cgtgacttca ccgcgttgtg caggattttt       180
ttggctggca aggcgccagc cgtcagcgac cgccgcttca gctcggcagc ctggcagggc       240
aatccgatgt cggccttcaa tgccgcatct tacctgctca acgccaaatt cctcagtgcc       300
atggtggagg cggtggacac cgcaccccag caaaagcaga aaatacgctt tgccgtgcag       360
caggtgattg atgccatgtc gcccgcgaac ttcctcgcca ccaacccgga agcgcagcaa       420
aaactgattg aaaccaaggg cgagagcctg acgcgtggcc tggtcaatat gctgggcgat       480
atcaacaagg ccatatctc gctgtcggac gaatcggcct ttgaagtggg ccgcaacctg       540
gccattaccc cgggcaccgt gatttacgaa atccgctgt tccagctgat ccagtacacg       600
ccgaccacgc cgacggtcag ccagcgcccg ctgttgatgg tgccgccgtg catcaacaag       660
ttctacatcc tcgacctgca accggaaaat tcgctggtgc gctacgcggt ggagcagggc       720
aacaccgtgt tcctgatctc gtggagcaat ccggacaagt cgctggccgg caccacctgg       780
gacgactacg tggagcaggg cgtgatcgaa gcgatccgca tcgtccagga cgtcagcggc       840
caggacaagc tgaacatgtt cggcttctgc gtgggcggca ccatcgttgc caccgcactg       900
gcggtactgg cggcgcgtgg ccagcacccg gcggccagcc tgaccctgct gaccaccttc       960
ctcgacttca gcgacaccgg cgtgctcgac gtcttcgtcg atgaaaccca ggtcgcgctg      1020
cgtgaacagc aattgcgcga tggcggcctg atgccgggcc gtgacctggc ctcgaccttc      1080

```
tcgagcctgc gtccgaacga cctggtatgg aactatgtgc agtcgaacta cctcaaaggc   1140
aatgagccgg cggcgtttga cctgctgttc tggaattcgg acagcaccaa tttgccgggc   1200
ccgatgttct gctggtacct gcgcaacacc tacctggaaa acagcctgaa agtgccgggc   1260
aagctgacgg tggccggcga aaagatcgac ctcggcctga tcgacgcccc ggccttcatc   1320
tacggttcgc gcgaagacca catcgtgccg tggatgtcgg cgtacggttc gctcgacatc   1380
ctcaaccagg gcaagccggg cgccaaccgc ttcgtgctgg gcgcgtccgg ccatatcgcc   1440
ggcgtgatca actcggtggc caagaacaag cgcagctact ggatcaacga cggtggcgcc   1500
gccgatgccc aggcctggtt cgatggcgcg caggaagtgc cgggcagctg gtggccgcaa   1560
tgggccgggt cctgaccca gcatggcggc aagaaggtca agcccaaggc caagcccggc   1620
aacgcccgct acaccgcgat cgaggcggcg cccggccgtt acgtcaaagc caagggctga   1680
```

<210> SEQ ID NO 23
<211> LENGTH: 559
<212> TYPE: PRT
<213> ORGANISM: Artificial Sequence
<220> FEATURE:
<223> OTHER INFORMATION: PhaC3/C5 fusion

<400> SEQUENCE: 23

```
Met Ser Asn Lys Asn Asn Asp Glu Leu Gln Trp Gln Ser Trp Phe Ser
1               5                   10                  15

Lys Ala Pro Thr Thr Glu Ala Asn Pro Met Ala Thr Met Leu Gln Asp
            20                  25                  30

Ile Gly Val Ala Leu Lys Pro Glu Ala Met Glu Gln Leu Lys Asn Asp
        35                  40                  45

Tyr Leu Arg Asp Phe Thr Ala Leu Trp Gln Asp Phe Leu Ala Gly Lys
    50                  55                  60

Ala Pro Ala Val Ser Asp Arg Arg Phe Ser Ser Ala Ala Trp Gln Gly
65                  70                  75                  80

Asn Pro Met Ser Ala Phe Asn Ala Ala Ser Tyr Leu Leu Asn Ala Lys
                85                  90                  95

Phe Leu Ser Ala Met Val Glu Ala Val Asp Thr Ala Pro Gln Gln Lys
            100                 105                 110

Gln Lys Ile Arg Phe Ala Val Gln Gln Val Ile Asp Ala Met Ser Pro
        115                 120                 125

Ala Asn Phe Leu Ala Thr Asn Pro Glu Ala Gln Gln Lys Leu Ile Glu
    130                 135                 140

Thr Lys Gly Glu Ser Leu Thr Arg Gly Leu Val Asn Met Leu Gly Asp
145                 150                 155                 160

Ile Asn Lys Gly His Ile Ser Leu Ser Asp Glu Ser Ala Phe Glu Val
                165                 170                 175

Gly Arg Asn Leu Ala Ile Thr Pro Gly Thr Val Ile Tyr Glu Asn Pro
            180                 185                 190

Leu Phe Gln Leu Ile Gln Tyr Thr Pro Thr Thr Pro Thr Val Ser Gln
        195                 200                 205

Arg Pro Leu Leu Met Val Pro Pro Cys Ile Asn Lys Phe Tyr Ile Leu
    210                 215                 220

Asp Leu Gln Pro Glu Asn Ser Leu Val Arg Tyr Ala Val Glu Gln Gly
225                 230                 235                 240

Asn Thr Val Phe Leu Ile Ser Trp Ser Asn Pro Asp Lys Ser Leu Ala
                245                 250                 255
```

Gly Thr Thr Trp Asp Asp Tyr Val Glu Gln Gly Val Ile Glu Ala Ile
                260                 265                 270

Arg Ile Val Gln Asp Val Ser Gly Gln Asp Lys Leu Asn Met Phe Gly
            275                 280                 285

Phe Cys Val Gly Gly Thr Ile Val Ala Thr Ala Leu Ala Val Leu Ala
        290                 295                 300

Ala Arg Gly Gln His Pro Ala Ala Ser Leu Thr Leu Thr Thr Phe
305                 310                 315                 320

Leu Asp Phe Ser Asp Thr Gly Val Leu Asp Val Phe Val Asp Glu Thr
                325                 330                 335

Gln Val Ala Leu Arg Glu Gln Gln Leu Arg Asp Gly Gly Leu Met Pro
            340                 345                 350

Gly Arg Asp Leu Ala Ser Thr Phe Ser Ser Leu Arg Pro Asn Asp Leu
        355                 360                 365

Val Trp Asn Tyr Val Gln Ser Asn Tyr Leu Lys Gly Asn Glu Pro Ala
    370                 375                 380

Ala Phe Asp Leu Leu Phe Trp Asn Ser Asp Ser Thr Asn Leu Pro Gly
385                 390                 395                 400

Pro Met Phe Cys Trp Tyr Leu Arg Asn Thr Tyr Leu Glu Asn Ser Leu
                405                 410                 415

Lys Val Pro Gly Lys Leu Thr Val Ala Gly Glu Lys Ile Asp Leu Gly
            420                 425                 430

Leu Ile Asp Ala Pro Ala Phe Ile Tyr Gly Ser Arg Glu Asp His Ile
        435                 440                 445

Val Pro Trp Met Ser Ala Tyr Gly Ser Leu Asp Ile Leu Asn Gln Gly
    450                 455                 460

Lys Pro Gly Ala Asn Arg Phe Val Leu Gly Ala Ser Gly His Ile Ala
465                 470                 475                 480

Gly Val Ile Asn Ser Val Ala Lys Asn Lys Arg Ser Tyr Trp Ile Asn
                485                 490                 495

Asp Gly Gly Ala Ala Asp Ala Gln Ala Trp Phe Asp Gly Ala Gln Glu
            500                 505                 510

Val Pro Gly Ser Trp Trp Pro Gln Trp Ala Gly Phe Leu Thr Gln His
        515                 520                 525

Gly Gly Lys Lys Val Lys Pro Lys Ala Lys Pro Gly Asn Ala Arg Tyr
    530                 535                 540

Thr Ala Ile Glu Ala Ala Pro Gly Arg Tyr Val Lys Ala Lys Gly
545                 550                 555

<210> SEQ ID NO 24
<211> LENGTH: 1821
<212> TYPE: DNA
<213> ORGANISM: Artificial Sequence
<220> FEATURE:
<223> OTHER INFORMATION: phaC3/C1 fusion

<400> SEQUENCE: 24
atgactagaa ggaggtttca tatgagtaac aagaacaacg atgagctggc gacgggtaaa        60
ggtgctgctg catcttctac tgaaggtaaa tctcagccgt ttaaattccc accgggtccg       120 ctggaccccgg ccacttggct ggaatggagc cgtcagtggc aaggtccgga gggcaatggc      180
ggtaccgtgc cgggtggctt tccgggtttc gaagcgttcg cggcgtcccc gctggcgggc      240
gtgaaaatcg accggctca gctggcagag atccagcagc gttatatgcg tgatttcacc       300
gagctgtggc gtggtctggc aggcggtgac accgagagcg ctggcaaact gcatgaccgt      360

```
cgcttcgcgt ccgaagcgtg gcacaaaaac gcgccgtatc gctatactgc ggcattttac    420
ctgctgaacg cacgtgcact gacggaactg gctgatgcag tagaagcgga tccgaaaacc    480
cgtcagcgta tccgttttgc ggtttcccag tgggtagatg ctatgagccc ggctaacttc    540
ctggccacca acccggacgc tcagaaccgt ctgatcgaga gccgtggtga aagcctgcgt    600
gccggcatgc gcaatatgct ggaagatctg acccgcggta aaatttccca aaccgatgag    660
actgccttcg aagtaggccg taacatggca gttaccgaag tgctgtggt attcgaaaac     720 gagttcttcc agctgctgca gtacaaacct ctgactgaca agtatacac ccgtccgctg     780 ctgctggtac cgccgtgcat taacaagttc tatattctgg acctgcagcc ggaaggttct    840
ctggtccgtt acgcagtcga acagggtcac actgtattcc tggtgagctg gcgcaatcca    900
gacgctagca tggctggctg tacctgggat gactatattg aaaacgcggc tatccgcgcc    960
atcgaggttg tgcgtgatat cagcggtcag gacaagatca cacccctggg ctttgtgtt    1020 ggtggcacga tcatctccac tgccctggcg gtcctggccg ccgtggtga gcacccggtg     1080 gcctctctga ccctgctgac tacccctgctg gacttcaccg atactggtat cctggatgtt   1140
ttcgtggacg agccacacgt tcagctgcgt gaggcgactc tgggcggcgc cagcggcggt    1200
ctgctgcgtg tgtcgagct ggccaatacc ttttccttcc tgcgcccgaa cgacctggtt     1260
tggaactacg ttgttgacaa ctatctgaaa ggcaacaccc cggtacctt cgatctgctg     1320 ttctggaacg tgatgcaac caacctgcct ggtccatggt actgttggta cctgcgtcat     1380
acttacctgc agaacgaact gaaagagccg ggcaaactga ccgtgtgtaa cgaacctgtg    1440
gacctgggcg cgattaacgt tcctacttac atctacggtt cccgtgaaga tcacatcgta    1500
ccgtggaccg cggcttacgc cagcaccgcg ctgctgaaga cgatctgcg tttcgtactg     1560 ggcgcatccg gccatatcgc aggtgtgatc aaccctcctg caaagaaaaa gcgttctcat    1620
tggaccaacg acgcgctgcc agaatccgcg caggattggc tggcaggtgc tgaggaacac    1680
catggttcct ggtggccgga ttggatgacc tggctgggta acaagccggt gcaaaacgt     1740 gcagctccaa ctgaatatgg tagcaagcgt tatgctgcaa tcgagccagc gccaggccgt    1800
tacgttaaag cgaaagcata a                                              1821
```

<210> SEQ ID NO 25
<211> LENGTH: 599
<212> TYPE: PRT
<213> ORGANISM: Artificial Sequence
<220> FEATURE:
<223> OTHER INFORMATION: PhaC3/C1 fusion

<400> SEQUENCE: 25

```
Met Ser Asn Lys Asn Asn Asp Glu Leu Ala Thr Gly Lys Gly Ala Ala
1               5                   10                  15

Ala Ser Ser Thr Glu Gly Lys Ser Gln Pro Phe Lys Phe Pro Pro Gly
                20                  25                  30

Pro Leu Asp Pro Ala Thr Trp Leu Glu Trp Ser Arg Gln Trp Gln Gly
            35                  40                  45

Pro Glu Gly Asn Gly Gly Thr Val Pro Gly Gly Phe Pro Gly Phe Glu
        50                  55                  60

Ala Phe Ala Ala Ser Pro Leu Ala Gly Val Lys Ile Asp Pro Ala Gln
65                  70                  75                  80

Leu Ala Glu Ile Gln Gln Arg Tyr Met Arg Asp Phe Thr Glu Leu Trp
                85                  90                  95

Arg Gly Leu Ala Gly Gly Asp Thr Glu Ser Ala Gly Lys Leu His Asp
```

```
            100                 105                 110
Arg Arg Phe Ala Ser Glu Ala Trp His Lys Asn Ala Pro Tyr Arg Tyr
        115                 120                 125

Thr Ala Ala Phe Tyr Leu Leu Asn Ala Arg Ala Leu Thr Glu Leu Ala
    130                 135                 140

Asp Ala Val Glu Ala Asp Pro Lys Thr Arg Gln Arg Ile Arg Phe Ala
145                 150                 155                 160

Val Ser Gln Trp Val Asp Ala Met Ser Pro Ala Asn Phe Leu Ala Thr
                165                 170                 175

Asn Pro Asp Ala Gln Asn Arg Leu Ile Glu Ser Arg Gly Glu Ser Leu
            180                 185                 190

Arg Ala Gly Met Arg Asn Met Leu Glu Asp Leu Thr Arg Gly Lys Ile
        195                 200                 205

Ser Gln Thr Asp Glu Thr Ala Phe Glu Val Gly Arg Asn Met Ala Val
    210                 215                 220

Thr Glu Gly Ala Val Val Phe Glu Asn Glu Phe Phe Gln Leu Leu Gln
225                 230                 235                 240

Tyr Lys Pro Leu Thr Asp Lys Val Tyr Thr Arg Pro Leu Leu Leu Val
                245                 250                 255

Pro Pro Cys Ile Asn Lys Phe Tyr Ile Leu Asp Leu Gln Pro Glu Gly
            260                 265                 270

Ser Leu Val Arg Tyr Ala Val Glu Gln Gly His Thr Val Phe Leu Val
        275                 280                 285

Ser Trp Arg Asn Pro Asp Ala Ser Met Ala Gly Cys Thr Trp Asp Asp
    290                 295                 300

Tyr Ile Glu Asn Ala Ala Ile Arg Ala Ile Glu Val Val Arg Asp Ile
305                 310                 315                 320

Ser Gly Gln Asp Lys Ile Asn Thr Leu Gly Phe Cys Val Gly Gly Thr
                325                 330                 335

Ile Ile Ser Thr Ala Leu Ala Val Leu Ala Ala Arg Gly Glu His Pro
            340                 345                 350

Val Ala Ser Leu Thr Leu Leu Thr Thr Leu Leu Asp Phe Thr Asp Thr
        355                 360                 365

Gly Ile Leu Asp Val Phe Val Asp Glu Pro His Val Gln Leu Arg Glu
    370                 375                 380

Ala Thr Leu Gly Gly Ala Ser Gly Gly Leu Leu Arg Gly Val Glu Leu
385                 390                 395                 400

Ala Asn Thr Phe Ser Phe Leu Arg Pro Asn Asp Leu Val Trp Asn Tyr
                405                 410                 415

Val Val Asp Asn Tyr Leu Lys Gly Asn Thr Pro Val Pro Phe Asp Leu
            420                 425                 430

Leu Phe Trp Asn Gly Asp Ala Thr Asn Leu Pro Gly Pro Trp Tyr Cys
        435                 440                 445

Trp Tyr Leu Arg His Thr Tyr Leu Gln Asn Glu Leu Lys Glu Pro Gly
    450                 455                 460

Lys Leu Thr Val Cys Asn Glu Pro Val Asp Leu Gly Ala Ile Asn Val
465                 470                 475                 480

Pro Thr Tyr Ile Tyr Gly Ser Arg Glu Asp His Ile Val Pro Trp Thr
                485                 490                 495

Ala Ala Tyr Ala Ser Thr Ala Leu Leu Lys Asn Asp Leu Arg Phe Val
            500                 505                 510

Leu Gly Ala Ser Gly His Ile Ala Gly Val Ile Asn Pro Pro Ala Lys
        515                 520                 525
```

```
Lys Lys Arg Ser His Trp Thr Asn Asp Ala Leu Pro Glu Ser Ala Gln
    530                 535                 540

Asp Trp Leu Ala Gly Ala Glu Glu His His Gly Ser Trp Trp Pro Asp
545                 550                 555                 560

Trp Met Thr Trp Leu Gly Lys Gln Ala Gly Ala Lys Arg Ala Ala Pro
                565                 570                 575

Thr Glu Tyr Gly Ser Lys Arg Tyr Ala Ala Ile Glu Pro Ala Pro Gly
            580                 585                 590

Arg Tyr Val Lys Ala Lys Ala
            595

<210> SEQ ID NO 26
<211> LENGTH: 1920
<212> TYPE: DNA
<213> ORGANISM: Artificial Sequence
<220> FEATURE:
<223> OTHER INFORMATION: phaC3/C33 fusion

<400> SEQUENCE: 26
atgagtaaca agaacaacga tgagctggcg aatttcgacc cgctggctgg cctgtctggt      60
caatcggtgc aacagttctg gaatgagcag tggagccgta ccctgcagac cttgcagcag     120
atgggtcaac cgggcctgcc gggcattcaa ggtatgccgg gtatgccaga catggcacaa     180
gcgtggaaag ccgctgtgcc ggaaccgggt gcactgcctg agaatgcgct gtctctggat     240
ccggagaagc tgctggaact gcagcgtcaa tatctggacg gtgcaaaagc gatggcagag     300
cagggcggtg cgcaagcatt gctggcaaaa gataaacgtt tcaataccga atcgtgggca     360
ggtaatccgc tgacggctgc gaccgcggca acctacctgc tgaactcccg tatgctgatg     420
ggtctggcgg acgctgttca gcggacgat aagacccgta accgtgtgcg ttttgcgatt     480
gagcagtggc tggcagcgat ggcgccgagc aacttcctgg cgctgaatgc tgaggcccaa     540
aagaaggcga tcgagactca gggcgagagc ctggcccaag cgtggcgaa cctgctggcg     600
gatatgcgtc agggtcatgt ctccatgacc gacgaaagcc tgtttacggt gggcaagaac     660
gtggcaacga ccgaaggtgc ggttgttttc gagaatgagc tgttccagtt gattgagtat     720
aagccgttga cggataaggt gcatgagcgc ccgttcctga tggtgccgcc gtgcatcaac     780
aaattctata tcctggatct gcaaccggac aacagcctga tccgttatgc cgttagccag     840
ggccatcgca cgttcgtcat gtcctggcgc aatccagacg aatctctggc ccgtaaaacg     900
tgggataact acatcgaaga tggcgttctg acgggtattc gcgtcgcgcg tgagattgct     960
ggtgcggagc agatcaacgt tctgggtttt tgtgtgggcg gcactatgtt gagcaccgcg    1020
ttggcggttc tgcaagcccg ccacgaccgc gagcacggcg cagtcgcagc accagccgct    1080
aaagcgccag cggcgaaacg tgcggcaggt agccgcagcg cggctcgtac gtccactgcg    1140
cgtgccaccg ccctgcagg tgttccgttc ccggttgcga cgtcaccctt gctgaccacc    1200
tttatcgatt tctccgacac cggcatcctg acgtgttca ttgatgaatc tgtcgtccgt    1260
tttcgcgaga tgcaaatggg tgaaggtggt ttgatgaagg ccaagacct ggcgagcacc    1320
tttagctttc tgcgcccgaa tgacttggtt tggaattacg tcgtgggcaa ctacctgaaa    1380
ggtgaaaccc ctccgccgtt tgacctgctg tattggaaca gcgatagcac caacctgccg    1440
ggtccgtact acgcgtggta cctgcgtaat ctgtacctgg aaaatcgcct ggcacagccg    1500
ggtgcgttga ctgtttgcgg tgaacgtatc gacatgcacc agctgcgtct gccggcgtac    1560
atctatggca gccgcgaaga tcacattgtt ccggttggtg gtagctatgc cagcacccaa    1620
```

```
gtgctgggtg gtgataagcg ctttgtgatg ggtgcgtccg gtcacattgc aggcgtcatc    1680
aacccgcctg caaagaagaa acgtagctac tggctgcgtg aagatggcca gctgccggcc    1740
acgctgaaag agtggcaggc cggtgccgac gagtatcctg gtagctggtg gcggattgg     1800 agcccgtggc tggccgagca cggtggcaaa ctggtggcag cgccgaagca atacggcaaa    1860
ggccgtgagt acacggcgat tgaaccggct ccaggccgct acgttttggt caaggcgtaa    1920
```

<210> SEQ ID NO 27
<211> LENGTH: 639
<212> TYPE: PRT
<213> ORGANISM: Artificial Sequence
<220> FEATURE:
<223> OTHER INFORMATION: PhaC3/C33 fusion

<400> SEQUENCE: 27

```
Met Ser Asn Lys Asn Asn Asp Glu Leu Ala Asn Phe Asp Pro Leu Ala
1               5                   10                  15

Gly Leu Ser Gly Gln Ser Val Gln Gln Phe Trp Asn Glu Gln Trp Ser
            20                  25                  30

Arg Thr Leu Gln Thr Leu Gln Gln Met Gly Gln Pro Gly Leu Pro Gly
        35                  40                  45

Ile Gln Gly Met Pro Gly Met Pro Asp Met Ala Gln Ala Trp Lys Ala
    50                  55                  60

Ala Val Pro Glu Pro Gly Ala Leu Pro Glu Asn Ala Leu Ser Leu Asp
65                  70                  75                  80

Pro Glu Lys Leu Leu Glu Leu Gln Arg Gln Tyr Leu Asp Gly Ala Lys
                85                  90                  95

Ala Met Ala Glu Gln Gly Gly Ala Gln Ala Leu Leu Ala Lys Asp Lys
            100                 105                 110

Arg Phe Asn Thr Glu Ser Trp Ala Gly Asn Pro Leu Thr Ala Ala Thr
        115                 120                 125

Ala Ala Thr Tyr Leu Leu Asn Ser Arg Met Leu Met Gly Leu Ala Asp
    130                 135                 140

Ala Val Gln Ala Asp Asp Lys Thr Arg Asn Arg Val Arg Phe Ala Ile
145                 150                 155                 160

Glu Gln Trp Leu Ala Ala Met Ala Pro Ser Asn Phe Leu Ala Leu Asn
                165                 170                 175

Ala Glu Ala Gln Lys Lys Ala Ile Glu Thr Gln Gly Glu Ser Leu Ala
            180                 185                 190

Gln Gly Val Ala Asn Leu Leu Ala Asp Met Arg Gln Gly His Val Ser
        195                 200                 205

Met Thr Asp Glu Ser Leu Phe Thr Val Gly Lys Asn Val Ala Thr Thr
    210                 215                 220

Glu Gly Ala Val Val Phe Glu Asn Glu Leu Phe Gln Leu Ile Glu Tyr
225                 230                 235                 240

Lys Pro Leu Thr Asp Lys Val His Glu Arg Pro Phe Leu Met Val Pro
                245                 250                 255

Pro Cys Ile Asn Lys Phe Tyr Ile Leu Asp Leu Gln Pro Asp Asn Ser
            260                 265                 270

Leu Ile Arg Tyr Ala Val Ser Gln Gly His Arg Thr Phe Val Met Ser
        275                 280                 285

Trp Arg Asn Pro Asp Glu Ser Leu Ala Arg Lys Thr Trp Asp Asn Tyr
    290                 295                 300

Ile Glu Asp Gly Val Leu Thr Gly Ile Arg Val Ala Arg Glu Ile Ala
```

```
                305                 310                 315                 320
Gly Ala Glu Gln Ile Asn Val Leu Gly Phe Cys Val Gly Gly Thr Met
            325                 330             335

Leu Ser Thr Ala Leu Ala Val Leu Gln Ala Arg His Asp Arg Glu His
            340                 345             350

Gly Ala Val Ala Ala Pro Ala Lys Ala Pro Ala Ala Lys Arg Ala
            355                 360             365

Ala Gly Ser Arg Ser Ala Ala Arg Thr Ser Thr Ala Arg Ala Thr Ala
    370                 375                 380

Pro Ala Gly Val Pro Phe Pro Val Ala Ser Val Thr Leu Leu Thr Thr
385                 390                 395                 400

Phe Ile Asp Phe Ser Asp Thr Gly Ile Leu Asp Val Phe Ile Asp Glu
            405                 410             415

Ser Val Val Arg Phe Arg Glu Met Gln Met Gly Glu Gly Gly Leu Met
            420                 425             430

Lys Gly Gln Asp Leu Ala Ser Thr Phe Ser Phe Leu Arg Pro Asn Asp
            435                 440             445

Leu Val Trp Asn Tyr Val Val Gly Asn Tyr Leu Lys Gly Glu Thr Pro
    450                 455                 460

Pro Pro Phe Asp Leu Leu Tyr Trp Asn Ser Asp Ser Thr Asn Leu Pro
465                 470                 475                 480

Gly Pro Tyr Tyr Ala Trp Tyr Leu Arg Asn Leu Tyr Leu Glu Asn Arg
            485                 490             495

Leu Ala Gln Pro Gly Ala Leu Thr Val Cys Gly Glu Arg Ile Asp Met
            500                 505             510

His Gln Leu Arg Leu Pro Ala Tyr Ile Tyr Gly Ser Arg Glu Asp His
            515                 520             525

Ile Val Pro Val Gly Gly Ser Tyr Ala Ser Thr Gln Val Leu Gly Gly
    530                 535                 540

Asp Lys Arg Phe Val Met Gly Ala Ser Gly His Ile Ala Gly Val Ile
545                 550                 555                 560

Asn Pro Pro Ala Lys Lys Lys Arg Ser Tyr Trp Leu Arg Glu Asp Gly
            565                 570             575

Gln Leu Pro Ala Thr Leu Lys Glu Trp Gln Ala Gly Ala Asp Glu Tyr
            580                 585             590

Pro Gly Ser Trp Trp Ala Asp Trp Ser Pro Trp Leu Ala Glu His Gly
            595                 600             605

Gly Lys Leu Val Ala Ala Pro Lys Gln Tyr Gly Lys Gly Arg Glu Tyr
    610                 615                 620

Thr Ala Ile Glu Pro Ala Pro Gly Arg Tyr Val Leu Val Lys Ala
625                 630                 635
```

POLYHYDROXYALKANOATE COPOLYMER COMPOSITIONS AND METHODS OF MAKING THE SAME

CROSS-REFERENCE TO RELATED APPLICATIONS

This application is a divisional of U.S. application Ser. No. 14/434,651, filed Apr. 9, 2015, which is a national stage application of International Appl. PCT/US2013/062812, filed Oct. 1, 2013, which claims the benefit of U.S. Provisional Application No. 61/734,489, filed Dec. 7, 2012, and U.S. Provisional Application No. 61/711,825, filed Oct. 10, 2012, the entire disclosures of which are hereby incorporated herein by reference.

TECHNICAL FIELD

The present disclosure relates to polyhydroxyalkanoate copolymer compositions and methods of making the same, and more particularly to polyhydroxyalkanoate copolymer compositions comprising a plurality of polyhydroxyalkanoate copolymer molecules, wherein the polyhydroxyalkanoate copolymer molecules (i) comprise 3-hydroxybutyrate monomers and 4-hydroxybutyrate monomers, (ii) have a monomeric molar percentage of 4-hydroxybutyrate monomers of 23.5 to 75%, and (iii) have a biobased content of ≥80%, and to methods of making the same comprising culturing an organism in the presence of one or more carbon raw materials.

BACKGROUND

Polyhydroxyalkanoates are biodegradable and biocompatible thermoplastic materials that can be produced from renewable resources and that have a broad range of industrial and biomedical applications. Polyhydroxyalkanoates can be produced as homopolymers, such as poly-3-hydroxybutyrate (also termed "PHB") and poly-4-hydroxybutyrate (also termed "P4HB"), or as copolymers, such as poly(3-hydroxybutyrate-co-4-hydroxybutyrate) (also termed "PHB-co-4HB"). Poly(3-hydroxybutyrate-co-4-hydroxybutyrate) copolymers are of interest for their potential to be produced from renewable resources and to be used for conferring rubber-like elasticity in polymer blends. Thus, for example, production of poly(3-hydroxybutyrate-co-4-hydroxybutyrate) with high amounts of 4HB monomer incorporation into the copolymer has been described previously in the literature using various microorganisms, but this was accomplished only when immediate precursors of 4-hydroxybutyryl-CoA, such as e.g. 4-hydroxybutyrate, γ-butyrolactone, and/or 1,4-butanediol were supplied with other carbon sources. E.g., Kunioka et al., Polymer Communications 29:174-176 (1988); Doi et al., Polymer Communications 30:169-171 (1989); Kimura et al., Biotechnol. Letters 14(6):445-450 (1992); Nakamura et al., Macromolecules 25(17):4237-4241 (1992); Saito and Doi, Int. J. Biol. Macromol. 16(2):99-104 (1994); Lee et al., Biotechnol. Letters 19(8):771-774 (1997); Choi et al., Appl. Environm. Microbiol. 65(4):1570-1577 (1999); Hsieh et al., J. Taiwan Inst. Chem. Engin. 40:143-147 (2009). Production of poly(3-hydroxybutyrate-co-4-hydroxybutyrate) copolymer from glucose as a sole carbon source in genetically engineered *Escherichia coli* cells has also been accomplished, but the reported monomeric molar percentages of 4-hydroxybutyrate monomers of the resulting copolymers have been low, e.g. 12.5% or less during stationary phase, unless other carbon sources were co-fed. Chen et al., U.S. Pub. No. 2012/0214213; see also Dennis and Valentin, U.S. Pat. No. 6,117,658; Valentin and Dennis, J. Biotechnol. 58:33-38 (1997), Chen et al., Chinese Patent Application CN 102382789 A; Li et al., Metab. Eng. 12:352-359 (2010). Production of poly-4-hydroxybutyrate homopolymer from a genetically engineered microbial biomass metabolizing a renewable feedstock, such as glucose, has also been described, but exemplary poly-4-hydroxybutyrate homopolymer titers were less than 50% by weight of biomass titers, and in any case poly-4-hydroxybutyrate homopolymer does not have the same properties as poly(3-hydroxybutyrate-co-4-hydroxybutyrate) copolymer. Van Walsem et al., WO 2011/100601.

SUMMARY

A polyhydroxyalkanoate copolymer composition is provided. The composition comprises a plurality of polyhydroxyalkanoate copolymer molecules. The polyhydroxyalkanoate copolymer molecules (i) comprise 3-hydroxybutyrate monomers and 4-hydroxybutyrate monomers, (ii) have a monomeric molar percentage of 4-hydroxybutyrate monomers of 23.5 to 75%, and (iii) have a biobased content of ≥80%.

Also provided is a method of making a polyhydroxyalkanoate copolymer composition. The composition comprises a plurality of polyhydroxyalkanoate copolymer molecules. The polyhydroxyalkanoate copolymer molecules (i) comprise 3-hydroxybutyrate monomers and 4-hydroxybutyrate monomers, (ii) have a monomeric molar percentage of 4-hydroxybutyrate monomers of 23.5 to 75%, and (iii) have a biobased content of ≥80%. The method comprises culturing an organism in the presence of one or more carbon raw materials under conditions under which (a) the one or more carbon raw materials are converted to 3-hydroxybutyryl-CoA and 4-hydroxybutyryl-CoA and (b) the 3-hydroxybutyryl-CoA and the 4-hydroxybutyryl-CoA are polymerized to form the polyhydroxyalkanoate copolymer molecules, thereby forming the composition. The organism has been genetically engineered to comprise enzymatic activities of a polyhydroxyalkanoate synthase, an acetyl-CoA acetyltransferase, an acetoacetyl-CoA reductase, a succinate semialdehyde dehydrogenase, a succinic semialdehyde reductase, and a CoA transferase, and to not comprise enzymatic activities of either an NAD+-dependent succinate-semialdehyde dehydrogenase or an NADP+-dependent succinate-semialdehyde dehydrogenase or both. The one or more carbon raw materials, taken together, have a biobased content of ≥80%.

BRIEF DESCRIPTION OF THE DRAWING

FIG. 1 is a schematic diagram of exemplary *E. coli* central metabolic pathways showing reactions that were modified or introduced in the Examples or that could be modified in the future. Reactions that were eliminated by deleting the corresponding genes in certain Examples are marked with an "X". Abbreviations: "PEP", phosphoenolpyruvate; "PYR", pyruvate; "Ac-CoA", acetyl-CoA; "AcAc-CoA", acetoacetyl-CoA; "3HB-CoA", 3-hydroxybutyryl-CoA; "CIT", citrate; "ICT", isocitrate; "αKG", alpha-ketoglutarate; "SUC-CoA", succinyl-CoA; "SUC", succinate; "Fum", fumarate; "MAL", L-malate; "OAA", oxaloacetate; "SSA", succinic semialdehyde; "4HB", 4-hydroxybutyrate; "4HB-P", 4-hydroxybutyryl-phosphate; "4HB-CoA", 4-hydroxybutyryl-CoA; "PHB-co-4HB", poly(3-hydroxybutyrate-co-4-hydroxybutyrate). Numbered reactions: "1", acetyl-CoA acetyltransferase (a.k.a. beta-ketothiolase); "2", acetoacetyl-CoA reductase; "3", succinate semialdehyde dehydrogenase; "4", alpha-ketoglutarate decarboxylase; "5", succinic semialdehyde reductase; "6", CoA transferase; "7", butyrate kinase; "8", phosphotransbutyrylase; "9", polyhydroxyalkanoate synthase; "10", succinate semialdehyde dehydrogenase; "11", phosphoenolpyruvate carboxylase; "12", 4-hydroxybutyryl-CoA thioesterase.

DETAILED DESCRIPTION

A description of example embodiments of the disclosure follows.

A polyhydroxyalkanoate copolymer composition is provided. The composition comprises a plurality of polyhydroxyalkanoate copolymer molecules. The composition can be, for example, a biomass composition, e.g. an organism that has produced, and comprises therein, the plurality of polyhydroxyalkanoate copolymer molecules, a composition free of non-polyhydroxyalkanoate biomass, e.g. a composition comprising polyhydroxyalkanoate copolymer molecules that have been isolated and/or purified from an organism that has produced the polyhydroxyalkanoate copolymer molecules, or a bioplastic composition, e.g. a homogeneous or blended composition comprising the polyhydroxyalkanoate copolymer molecules and suitable for use as a bioplastic.

The polyhydroxyalkanoate copolymer molecules comprise 3-hydroxybutyrate monomers and 4-hydroxybutyrate monomers. Accordingly, each polyhydroxyalkanoate copolymer molecule comprises both 3-hydroxybutyrate monomers and 4-hydroxybutyrate monomers. Such molecules can be synthesized, for example, by PHA-synthase mediated copolymerization of 3-hydroxybutyryl-CoA and 4-hydroxybutyryl-CoA to yield molecules of the copolymer, e.g. poly(3-hydroxybutyrate-co-4-hydroxybutyrate) copolymer. Exemplary suitable PHA synthases are described in the Examples below. Each polyhydroxyalkanoate copolymer molecule also optionally can comprise further additional monomers, e.g. 5-hydroxyvalerate monomers, for example based on the further presence of polymerizable precursors of the additional monomers during PHA-synthase mediated copolymerization of 3-hydroxybutyryl-CoA and 4-hydroxybutyryl-CoA.

The polyhydroxyalkanoate copolymer molecules have a monomeric molar percentage of 4-hydroxybutyrate monomers of 23.5 to 75%. Accordingly, 23.5 to 75% of the monomeric units of the polyhydroxyalkanoate copolymer molecules, taken together, are 4-hydroxybutyrate monomers, with the remaining 25 to 76.5% of the monomeric units of the polyhydroxyalkanoate copolymer molecules corresponding to 3-hydroxybutyrate monomers and optionally further additional monomers. In some embodiments, substantially all, e.g. ≥95% or ≥99%, of the remaining 25 to 76.5% of the monomeric units correspond to 3-hydroxybutyrate monomers, with the rest corresponding to further additional monomers. In some embodiments, all of the remaining 25 to 76.5% of the monomeric units correspond to 3-hydroxybutyrate monomers, such that the polyhydroxyalkanoate copolymer molecules include no further additional monomers. Thus, for example with regard to poly(3-hydroxybutyrate-co-4-hydroxybutyrate) copolymer in particular, for polyhydroxyalkanoate copolymer molecules having a monomeric molar percentage of 4-hydroxybutyrate monomers of 23.5 to 75%, the remaining 25 to 76.5% of the monomeric units of the polyhydroxyalkanoate copolymer molecules correspond to 3-hydroxybutyrate monomers. Exemplary suitable methods for determining the monomeric molar percentage of 3-hydroxybutyrate monomers and 4-hydroxybutyrate monomers of polyhydroxyalkanoate copolymer molecules are described in the Examples below.

In some embodiments, the monomeric molar percentage of 4-hydroxybutyrate monomers of the polyhydroxyalkanoate copolymer molecules can be 25 to 70%. The monomeric molar percentage of 4-hydroxybutyrate monomers of the polyhydroxyalkanoate copolymer molecules can be, for example, 30 to 40%, 40 to 50%, 50 to 60%, or 60 to 70%.

The monomeric molar percentages of 4-hydroxybutyrate monomers of polyhydroxyalkanoate copolymer molecules affect properties of compositions thereof, for example with respect to melting temperatures, elongation to break, glass transition temperatures, and the like. For example, as the monomeric molar percentages of 4-hydroxybutyrate monomers of poly(3-hydroxybutyrate-co-4-hydroxybutyrate) copolymer molecules increase above 10%, the melting temperature decreases below 130° C. and the elongation to break increases above 400%. Saito Y. et al., 39 Polym. Int. 169 (1996). Thus, polyhydroxyalkanoate copolymer molecules having monomeric molar percentages of 4-hydroxybutyrate monomers in each of the various ranges disclosed above can be used to engineer compositions to have particular desired properties.

The polyhydroxyalkanoate copolymer molecules have a biobased content of ≥80%. Biobased content, as the term is used herein, means the amount of biobased carbon in a material or product as a percent of the weight (mass) of the total organic carbon of the material or product, as defined in ASTM D6866-12, Standard Test Methods for Determining the Biobased Content of Solid, Liquid, and Gaseous Samples Using Radiocarbon Analysis (ASTM International, U.S., 2012), which is incorporated by reference herein. As discussed in ASTM D6866-12, total organic carbon can include both biobased carbon and fossil carbon. Biobased carbon corresponds to organic carbon that includes radiocarbon, i.e. $^{14}C$, in an amount indicative of recent cycling through the living biosphere, e.g. recent incorporation of atmospheric $CO_2$, including a known percentage of $^{14}C$, into organic carbon. Fossil carbon corresponds to organic carbon that includes little or no radiocarbon because the age of the fossil carbon, as measured from the date of incorporation of atmospheric $CO_2$, is much greater than the half-life of $^{14}C$, i.e. all or essentially all of the $^{14}C$ that had been incorporated has decayed. Accordingly, as applied to polyhydroxyalkanoate copolymer molecules, biobased content means the amount of biobased carbon in the polyhydroxyalkanoate copolymer molecules as a percent of the weight (mass) of the total organic carbon of the polyhydroxyalkanoate copolymer molecules. The biobased content of the polyhydroxyalkanoate copolymer molecules can be measured, for example, in accordance with ASTM D6866-12, based on determining the contents of $^{14}C$ and $^{12}C$ in $CO_2$ derived by combustion of the polyhydroxyalkanoate, and correcting for post 1950 bomb $^{14}C$ injection into the atmosphere, among other methods. Thus, for example, the polyhydroxyalkanoate copolymer molecules can have a biobased content of ≥80% as measured in accordance with ASTM D6866-12. Other suitable approaches for measuring biobased content, as are known in the art, also can be used. Differences in biobased contents between different polyhydroxyalkanoate copolymer molecules are indicative of structural differences, i.e. differences in the ratios of $^{14}C$ to $^{12}C$ thereof, between the different polyhydroxyalkanoate copolymer molecules.

In some embodiments, the biobased content of the polyhydroxyalkanoate copolymer molecules is ≥95%. In some embodiments, the biobased content of the polyhydroxyalkanoate copolymer molecules is ≥99%. In some embodiments, the biobased content of the polyhydroxyalkanoate copolymer molecules is 100%. Thus, for example, the biobased content of the polyhydroxyalkanoate copolymer molecules can be ≥95%, or ≥99%, or 100%, in each case again as measured in accordance with ASTM D6866-12.

Polyhydroxyalkanoate copolymer molecules having the above-noted biobased contents can be used for the manufacture of biobased plastics in which most or all fossil carbon has been replaced by renewable biobased carbon, with accompanying environmental benefits. Moreover, polyhydroxyalkanoate copolymer molecules having the above-noted biobased contents can be distinguished readily from polyhydroxyalkanoate copolymer molecules and other polymers and compounds not having the above-noted biobased contents, based on the above-noted structural differences associated with differences in biobased contents, with accompanying regulatory benefits.

The polyhydroxyalkanoate copolymer molecules can have a weight average molecular weight of 250 kilodalton ("kDa") to 2.0 megadalton ("MDa"). The polyhydroxyalkanoate copolymer molecules can occur in a distribution with respect to their molecular weights, and the physical properties and rheological properties of compositions of the polyhydroxyalkanoate copolymer molecules can depend on the distribution. Molecular weights of polymers can be calculated various ways. Weight average molecular weight, also termed $M_w$, is the sum of the weights of the various chain lengths, times the molecular weight of the chain, divided by the total weight of all of the chains ($\Sigma N_i M_i^2 / \Sigma N_i M_i$). Number average molecular weight, also termed $M_n$, is the sum of the number of chains of a given length, times the molecular weight of the chain, divided by the total number of chains ($\Sigma N_i M_i / \Sigma N_i$). Polydispersity index provides a measure of the broadness of a molecular weight distribution of a polymer and is calculated as the weight average molecular weight divided by the number average molecular weight. As used herein, the term molecular weight refers to weight average molecular weight unless context indicates otherwise.

Weight average molecular weight of polyhydroxyalkanoate copolymer molecules can be determined, for example, by use of light scattering and gel permeation chromatography with polystyrene standards. Chloroform can be used as both the eluent for the gel permeation chromatography and as the diluent for the polyhydroxyalkanoates. Calibration curves for determining molecular weights can be generated by using linear polystyrenes as molecular weight standards and a calibration method based on log molecular weight as a function of elution volume.

In some embodiments, the weight average molecular weight of the polyhydroxyalkanoate copolymer molecules is 1.5 MDa to 2.0 MDa, e.g. as determined by use of light scattering and gel permeation chromatography with polystyrene standards. In some embodiments the weight average molecular weight of the polyhydroxyalkanoate copolymer molecules is 1.7 MDa to 2.0 MDa, e.g. again as determined by use of light scattering and gel permeation chromatography with polystyrene standards.

Unexpectedly, it has been observed here that the polyhydroxyalkanoate copolymer molecules having a monomeric molar percentage of 4-hydroxybutyrate monomers of 23.5 to 75%, e.g. 25 to 70%, 30 to 40%, 40 to 50%, 50 to 60%, or 60 to 70%, can be obtained in polyhydroxyalkanoate titers ≥50% by weight of biomass titers in accordance with the methods described below, e.g. culturing an organism in the presence of one or more carbon raw materials, as discussed below, wherein the organism has been genetically engineered, as also discussed below. More specifically, it has been observed that the polyhydroxyalkanoate copolymer molecules can be obtained in polyhydroxyalkanoate titers exceeding 50% by weight of biomass titers by culturing the organism in the presence of glucose as a sole carbon source and thus in the absence of compounds that are immediate precursors of 4-hydroxybutyryl-CoA and/or compounds that are typically manufactured from nonrenewable resources. It has also been observed that during culturing of an organism, not so genetically engineered, in the presence of glucose and 1,4-butanediol, which is a compound that is both an immediate precursor of 4-hydroxybutyryl-CoA and typically manufactured from nonrenewable resources, increasing the amount of 1,4-butanediol, while being useful for achieving relatively higher monomeric molar percentages of 4-hydroxybutyrate monomers of the polyhydroxyalkanoate copolymer molecules, results in relatively lower yields of the polyhydroxyalkanoate copolymer molecules and relatively lower weight average molecular weights thereof. Without wishing to be bound by theory, it is believed that the polyhydroxyalkanoate titers ≥50% by weight of biomass titers of the polyhydroxyalkanoate copolymer molecules that can be obtained by the methods described below are indicative of unexpectedly higher molecular weights associated with the polyhydroxyalkanoate copolymer molecules. Polyhydroxyalkanoate copolymer molecules having weight average molecular weights in the above-noted ranges can be used to prepare polyhydroxyalkanoate copolymer compositions having desired physical properties and rheological properties.

The composition can have a glass transition temperature of −60° C. to −5° C. Glass transition temperature is the temperature above which polymer molecules begin coordinated molecular motions. Physically, the polymer modulus begins to drop several orders of magnitude until the polymer finally reaches a rubbery state. In some embodiments, the glass transition temperature of the composition is, for example, −50° C. to −15° C., −50° C. to −20° C., or −45° C. to −15° C. Compositions having glass transition temperatures in the above-noted ranges can be used to ensure that the compositions are in a rubbery state at desired temperatures of use.

The composition can be one wherein the monomeric molar percentage of 4-hydroxybutyrate monomers of the polyhydroxyalkanoate copolymer molecules does not decrease with increasing molecular weight of the polyhydroxyalkanoate copolymer molecules. As noted above, the polyhydroxyalkanoate copolymer molecules can occur in a distribution with respect to their molecular weights. Monomeric molar percentages of 4-hydroxybutyrate monomers may vary between individual polyhydroxyalkanoate copolymer molecules. A composition wherein the monomeric molar percentage of 4-hydroxybutyrate monomers of the polyhydroxyalkanoate copolymer molecules does not decrease with increasing molecular weight of the polyhydroxyalkanoate copolymer molecules can be, for example, a composition wherein the monomeric molar percentage of 4-hydroxybutyrate monomers of polyhydroxyalkanoate copolymer molecules at the high end of the molecular weight distribution is not lower than the monomeric molar percentage of 4-hydroxybutyrate monomers of polyhydroxyalkanoate copolymer molecules at the low end of the molecular weight distribution. Thus, for example, the composition can be one wherein the monomeric molar percentage of 4-hydroxybutyrate monomers of the polyhydroxyalkanoate copolymer molecules does not vary substantially, e.g. at all, with increasing molecular weight of the polyhydroxyalkanoate copolymer molecules, e.g. the monomeric molar percentage of 4-hydroxybutyrate monomers of polyhydroxyalkanoate copolymer molecules at the high end of the molecular weight distribution is essentially the same, e.g. identical, to that of polyhydroxyalkanoate copolymer molecules at the low end of the molecular weight distribution. Also for example, the composition can be one wherein the monomeric molar percentage of 4-hydroxybutyrate monomers of the polyhydroxyalkanoate copolymer molecules increases with increasing molecular weight of the polyhydroxyalkanoate copolymer molecules, e.g. the monomeric molar percentage of 4-hydroxybutyrate monomers of polyhydroxyalkanoate copolymer molecules at the high end of the molecular weight distribution is higher than that of polyhydroxyalkanoate copolymer molecules at the low end of the molecular weight distribution.

Unexpectedly, it has been observed here that the polyhydroxyalkanoate copolymer molecules having a monomeric molar percentage of 4-hydroxybutyrate monomers of 23.5 to 75%, and more particularly about 50 to 60%, can be obtained in forms in which the monomeric molar percentages of 4-hydroxybutyrate monomers of the polyhydroxyalkanoate copolymer molecules of a culture of an organism do not decrease during later stages of culturing of the organism, e.g. during stationary phase, in accordance with the methods described below, e.g. culturing an organism in the presence of one or more carbon raw materials, such as glucose as a sole carbon source, as discussed below, wherein the organism has been genetically engineered, as also discussed below. It has also been observed that during culturing of an organism not so genetically engineered, in the presence of glucose and 1,4-butanediol, decreasing amounts of 1,4-butanediol that are typical of later stages of such culturing (e.g. reflecting consumption of most of the 1,4-butanediol that had been present) result in decreasing monomeric molar percentages of 4-hydroxybutyrate monomers of polyhydroxyalkanoate copolymer molecules of a culture of the organism with concomitant increasing weight average molecular weights of the copolymer molecules. Without wishing to be bound by theory, it is believed that the absence of a decrease of the monomeric molar percentage of 4-hydroxybutyrate monomers of the polyhydroxyalkanoate copolymer molecules of a culture of an organism during later stages of the culturing of the organism, in accordance with the methods described below, is indicative of polyhydroxyalkanoate copolymer molecules wherein the monomeric molar percentage of 4-hydroxybutyrate monomers of the polyhydroxyalkanoate copolymer molecules does not decrease with increasing molecular weight of the polyhydroxyalkanoate copolymer molecules. Polyhydroxyalkanoate copolymer molecules wherein the monomeric molar percentage of 4-hydroxybutyrate monomers of the polyhydroxyalkanoate copolymer molecules does not decrease with increasing molecular weight of the polyhydroxyalkanoate copolymer molecules can be used to ensure consistent structural and physical properties of compositions thereof.

The composition can be one wherein the polyhydroxyalkanoate copolymer molecules are produced in a fermentation process using one or more carbon raw materials that, taken together, have a biobased content of ≥80%; the one or more carbon raw materials comprise a carbon source selected from the group consisting of glucose, levoglucosan, sucrose, lactose, fructose, xylose, maltose, arabinose, and mixtures thereof; and the yield is greater than 0.25 g of the polyhydroxyalkanoate copolymer molecules per gram of the carbon source. For example, in some embodiments the yield is greater than 0.30 g, or greater than 0.35 g, or greater than 0.40 g, of the polyhydroxyalkanoate copolymer molecules per gram of the carbon source.

Methods of making polyhydroxyalkanoate copolymer compositions, as described above, are disclosed below.

A polymer blend composition is also provided. The polymer blend composition comprises a polyhydroxyalkanoate composition and a plurality of molecules of a second polymer. The polyhydroxyalkanoate composition can be any of the polyhydroxyalkanoate compositions as described above, for example a polyhydroxyalkanoate copolymer composition comprising a plurality of polyhydroxyalkanoate copolymer molecules, wherein the polyhydroxyalkanoate copolymer molecules (i) comprise 3-hydroxybutyrate monomers and 4-hydroxybutyrate monomers, (ii) have a monomeric molar percentage of 4-hydroxybutyrate monomers of 23.5 to 75%, and (iii) have a biobased content of ≥80%. Moreover, the polyhydroxyalkanoate composition can be one, for example, wherein (a) the monomeric molar percentage of 4-hydroxybutyrate monomers of the polyhydroxyalkanoate copolymer molecules is 25 to 70%, 30 to 40%, 40 to 50%, 50 to 60%, or 60 to 70%, (b) the biobased content of the polyhydroxyalkanoate copolymer molecules is ≥95%, ≥99%, or 100% (c) the polyhydroxyalkanoate copolymer molecules have a weight average molecular weight of 250 kDa to 2.0 MDa, 1.5 MDa to 2.0 MDa, or 1.7 MDa to 2.0 MDa, (d) the composition has a glass transition temperature of −60° C. to −5° C., −50° C. to −15° C., −50° C. to −20° C., or −45° C. to −15° C., (e) the monomeric molar percentage of 4-hydroxybutyrate monomers of the polyhydroxyalkanoate copolymer molecules does not decrease with increasing molecular weight of the polyhydroxyalkanoate copolymer molecules, and/or (f) the polyhydroxyalkanoate copolymer molecules are produced in a fermentation process using one or more carbon raw materials that, taken together, have a biobased content of ≥80%, as described above.

The second polymer can be, for example, a biobased polymer or a non-biobased polymer. Suitable biobased polymers include, for example, polylactic acid, polybutylene succinate, polybutylene succinate adipate, polybutylene adipate terephthalate, and/or polypropylene carbonate, wherein the polymers of the biobased plastics are derived from biobased succinic acid, biobased adipic acid, biobased 1,4-butanediol, biobased polypropylene oxide, and/or carbon dioxide. Suitable biobased polymers also include, for example, additional polyhydroxyalkanoates other than poly (3-hydroxybutyrate-co-4-hydroxybutyrate) copolymer, such as, for example, homopolymers such as poly-3-hydroxybutyrate homopolymer and poly-4-hydroxybutyrate homopolymer, other copolymers, such as poly-3-hydroxybutyrate-co-hydroxyvalerate and poly-3-hydroxybutyrate-co-3-hydroxyhexanoate, and blends of these and other polyhydroxyalkanoates. Suitable non-biobased polymers include, for example, polyvinylchloride.

The polymer blend composition can be used for a wide variety of applications, e.g. packaging film, based on optimization of mechanical properties (e.g. tensile strength, puncture resistance, and elongation), thermal properties (e.g. heat distortion temperature), and/or optical properties (e.g. clarity). The polymer blend composition wherein the second polymer is a biobased polymer in particular can be used for optimizing performance properties and to achieve high biobased contents. The polymer blend composition wherein the second polymer is polyvinylchloride has improved properties including improved processing in comparison to polyvinylchloride alone. The polymer blend composition can be blended by suitable methods that are known in the art.

The polymer blend composition can be one, for example, wherein the polyhydroxyalkanoate copolymer molecules are present at 5 to 95 weight percent of the polymer blend composition. For example, the polymer blend composition can be one wherein the polyhydroxyalkanoate copolymer molecules are present at 20 to 40 weight percent, 25 to 35 weight percent, or 28 to 33 weight percent, of the polymer blend composition. The polymer blend composition also can be, for example, continuous or co-continuous. The polymer blend composition also can be one, for example, wherein the polyhydroxyalkanoate copolymer molecules and the molecules of the second polymer form a single phase, e.g. wherein the second polymer is polyvinyl chloride. The polymer blend composition also can be one, for example, wherein the polyhydroxyalkanoate copolymer molecules and the molecules of the second polymer form more than a single phase, e.g. wherein the second polymer is polylactic acid. The polymer blend composition also can have, for example, a lower crystallizability, i.e. maximum theoretical crystallinity, than a corresponding composition that lacks the polyhydroxyalkanoate copolymer molecules.

A biomass composition is also provided. The biomass composition comprises a polyhydroxyalkanoate composition, e.g. any of the polyhydroxyalkanoate compositions as described above, wherein the polyhydroxyalkanoate copolymer molecules are present at ≥50 weight percent of the biomass composition. Thus, again, the polyhydroxyalkanoate copolymer composition can be one, for example, comprising a plurality of polyhydroxyalkanoate copolymer molecules, wherein the polyhydroxyalkanoate copolymer molecules (i) comprise 3-hydroxybutyrate monomers and 4-hydroxybutyrate monomers, (ii) have a monomeric molar percentage of 4-hydroxybutyrate monomers of 23.5 to 75%, and (iii) have a biobased content of ≥80%. Moreover, the polyhydroxyalkanoate composition can be one, for example, wherein (a) the monomeric molar percentage of 4-hydroxybutyrate monomers of the polyhydroxyalkanoate copolymer molecules is 25 to 70%, 30 to 40%, 40 to 50%, 50 to 60%, or 60 to 70%, (b) the biobased content of the polyhydroxyalkanoate copolymer molecules is ≥95%, ≥99%, or 100%, (c) the polyhydroxyalkanoate copolymer molecules have a weight average molecular weight of 250 kDa to 2.0 MDa, 1.5 MDa to 2.0 MDa, or 1.7 MDa to 2.0 MDa, (d) the composition has a glass transition temperature of −60° C. to −5° C., −50° C. to −15° C., −50° C. to −20° C., or −45° C. to −15° C., (e) the monomeric molar percentage of 4-hydroxybutyrate monomers of the polyhydroxyalkanoate copolymer molecules does not decrease with increasing molecular weight of the polyhydroxyalkanoate copolymer molecules, and/or (f) the polyhydroxyalkanoate copolymer molecules are produced in a fermentation process using one or more carbon raw materials that, taken together, have a biobased content of ≥80%, as described above.

As noted, the polyhydroxyalkanoate copolymer molecules are present at ≥50 weight percent of the biomass composition. As used herein, weight percent of the biomass composition refers to dry weight of the biomass composition, e.g. cell dry weight. The polyhydroxyalkanoate copolymer molecules can be present, for example, at ≥60, ≥70, ≥80, ≥85, or ≥90 weight percent of the biomass composition.

A method of making a polyhydroxyalkanoate copolymer composition is also provided. Again, the polyhydroxyalkanoate composition can be any of the polyhydroxyalkanoate compositions as described above, for example a polyhydroxyalkanoate copolymer composition comprising a plurality of polyhydroxyalkanoate copolymer molecules, wherein the polyhydroxyalkanoate copolymer molecules (i) comprise 3-hydroxybutyrate monomers and 4-hydroxybutyrate monomers, (ii) have a monomeric molar percentage of 4-hydroxybutyrate monomers of 23.5 to 75%, and (iii) have a biobased content of ≥80%. Moreover, the polyhydroxyalkanoate composition can be one, for example, wherein (a) the monomeric molar percentage of 4-hydroxybutyrate monomers of the polyhydroxyalkanoate copolymer molecules is 25 to 70%, 30 to 40%, 40 to 50%, 50 to 60%, or 60 to 70%, (b) the biobased content of the polyhydroxyalkanoate copolymer molecules is ≥95%, ≥99%, or 100%, (c) the polyhydroxyalkanoate copolymer molecules have a weight average molecular weight of 250 kDa to 2.0 MDa, 1.5 MDa to 2.0 MDa, or 1.7 MDa to 2.0 MDa, (d) the composition has a glass transition temperature of −60° C. to −5° C., −50° C. to −15° C., −50° C. to −20° C., or −45° C. to −15° C., (e) the monomeric molar percentage of 4-hydroxybutyrate monomers of the polyhydroxyalkanoate copolymer molecules does not decrease with increasing molecular weight of the polyhydroxyalkanoate copolymer molecules, and/or (f) the polyhydroxyalkanoate copolymer molecules are produced in a fermentation process using one or more carbon raw materials that, taken together, have a biobased content of ≥80%, as described above.

The method can comprise culturing an organism in the presence of one or more carbon raw materials under conditions under which (a) the one or more carbon raw materials are converted to 3-hydroxybutyryl-CoA and 4-hydroxybutyryl-CoA and (b) the 3-hydroxybutyryl-CoA and the 4-hydroxybutyryl-CoA are polymerized to form the polyhydroxyalkanoate copolymer molecules, thereby forming the composition.

The culturing can comprise, for example, cultivating the organism by fermentation, shake-flask cultivation, and the like. Fermentation can be carried out, for example, at scales ranging from laboratory scale, e.g. 1 L, to industrial manufacturing scale, e.g. 20,000 to 100,000 L. Additional suitable culturing approaches are described in the Examples below.

The organism can be, for example, a microbial strain or an algal strain. Suitable microbial strains include, for example, an *Escherichia coli* strain or a *Ralstonia eutropha* strain. Suitable algal strains include, for example, a *Chlorella* strain. Additional suitable organisms are described in the Examples below.

The one or more carbon raw materials can comprise a carbon raw material that can be used in an industrial process, e.g. to supply a carbon or other energy source for cells of a fermentation process, and/or that is renewable, e.g. material derived from living organisms or their metabolic byproducts including material derived from biomass, often consisting of underutilized components like chaff or stover. For example, the one or more carbon raw materials can comprise a carbon source selected from the group consisting of glucose, levoglucosan, sucrose, lactose, fructose, xylose, maltose, arabinose, and mixtures thereof. Also for example, the one or more carbon raw materials can comprise one or more of molasses, starch, a fatty acid, a vegetable oil, a lignocellulosic material, ethanol, acetic acid, glycerol, a biomass-derived synthesis gas, and methane originating from a landfill gas.

Considering the one or more carbon raw materials further, in some embodiments, the one or more carbon raw materials can consist essentially of a carbon source selected from the group consisting of glucose, levoglucosan, sucrose, lactose, fructose, xylose, maltose, arabinose, and mixtures thereof. In some embodiments, the one or more carbon raw materials can consist of a carbon source selected from the group consisting of glucose, levoglucosan, sucrose, lactose, fructose, xylose, maltose, arabinose, and mixtures thereof. Thus, in some embodiments the one or more carbon raw materials can consist essentially of a single carbon source, e.g. glucose. Also, in some embodiments the one or more carbon raw materials can consist of a single carbon source, again e.g. glucose.

The one or more carbon raw materials can also exclude particular compounds, such as compounds that are immediate precursors of 4-hydroxybutyryl-CoA and/or compounds that are typically manufactured from nonrenewable resources, e.g. from petroleum, based on substantially lower cost in comparison to manufacture thereof from renewable resources, e.g. crops. Incorporation of such compounds for production of polyhydroxyalkanoate copolymer molecules can be costly, particularly with respect to industrial manufacturing scale, e.g. by fermentation using 20,000 to 100,000 L vessels, based on requiring additional feeds and thus infrastructure and quality control, and can result in a need for tighter control in order to achieve polyhydroxyalkanoate copolymer compositions with structural consistency. The one or more carbon raw materials can be, for example, ones that do not comprise γ-butyrolactone, 1,4-butanediol, 4-hydroxybutyrate, 3-hydroxybutyrate, α-ketoglutarate, oxaloacetate, malate, fumarate, citrate, succinate, or 3-hydroxybutyrate, and thus that exclude each of these compounds. Thus, for example, the culturing of the organism can be carried out in the absence of γ-butyrolactone, 1,4-butanediol, 4-hydroxybutyrate, 3-hydroxybutyrate, α-ketoglutarate, oxaloacetate, malate, fumarate, citrate, succinate, and 3-hydroxybutyrate, i.e. without adding any of these compounds exogenously before, during, or after the culturing.

The conditions can be conditions that are suitable, e.g. typical and/or optimal, for cultivation of the organism, e.g. with respect to temperature, oxygenation, initial titer of the organism, time of cultivation, etc. Exemplary suitable conditions are provided in the Examples below.

The one or more carbon raw materials can be converted to 3-hydroxybutyryl-CoA and 4-hydroxybutyryl-CoA by enzymes expressed by the organism, as discussed in detail in the Examples. The 3-hydroxybutyryl-CoA and the 4-hydroxybutyryl-CoA also can be polymerized to form the polyhydroxyalkanoate copolymer molecules, thereby forming the composition, by enzymes expressed by the organism, again as discussed in detail in the Examples.

In accordance with the method, the organism has been genetically engineered to comprise enzymatic activities of a polyhydroxyalkanoate synthase, an acetyl-CoA acetyltransferase, an acetoacetyl-CoA reductase, a succinate semialdehyde dehydrogenase, a succinic semialdehyde reductase, and a CoA transferase, and to not comprise enzymatic activities of either an NAD+-dependent succinate-semialdehyde dehydrogenase or an NADP+-dependent succinate-semialdehyde dehydrogenase or both.

The organism can be genetically engineered to comprise the enzymatic activities of a polyhydroxyalkanoate synthase, an acetyl-CoA acetyltransferase, an acetoacetyl-CoA reductase, a succinate semialdehyde dehydrogenase, a succinic semialdehyde reductase, and a CoA transferase, for example, by transforming the organism with one or more genes encoding each of the enzymatic activities. For example, the genes can be stably incorporated into the organism, e.g. by introduction on one or more stable plasmids and/or by integration into the genome of the organism. The organism can also be genetically engineered to comprise the enzymatic activities, for example, by altering the promoter regions of one or more genes encoding each of the enzymatic activities, for example by replacing naturally occurring promoters with stronger promoters and/or by eliminating repressor sequences. In addition, combinations of these approaches and the like can be used. Using approaches such as these can result in integration of the genes in the organism with high stability, e.g. greater than 50 generations of the organism, and high expression, sufficient for industrial production, for example, by fermentation using 20,000 to 100,000 L vessels. Suitable exemplary approaches are discussed in more detail below.

The organism also can be genetically engineered to not comprise enzymatic activities of either an NAD+-dependent succinate-semialdehyde dehydrogenase or an NADP+-dependent succinate-semialdehyde dehydrogenase or both, for example, by introducing one or more inhibitory mutations or sequences in the organism to inhibit expression of either or both activities, by deleting from the genome of the organism the corresponding genes that encode either or both activities, by disrupting either or both of the corresponding genes partially or completely by homologous recombination, and/or by interfering with expression of either or both of the corresponding genes such as by expressing siRNAs that interfere with expression of the corresponding genes. Suitable exemplary approaches are discussed in more detail below.

In accordance with the method, the organism can further be genetically engineered to comprise enzymatic activities of an alpha-ketoglutarate decarboxylase or 2-oxoglutarate decarboxylase, and an L-1,2-propanediol oxidoreductase. The organism also can be genetically engineered to not comprise enzymatic activities of one or more of a thioesterase II, a multifunctional acyl-CoA thioesterase I and protease I and lysophospholipase L, an acyl-CoA thioesterase, and an aldehyde dehydrogenase.

Also in accordance with the method, the one or more carbon raw materials, taken together, have a biobased content of ≥80%. By this it is meant that the amount of biobased carbon in the one or more carbon raw materials, taken together, is ≥80% of the weight (mass) of the total organic carbon of the one or more carbon raw materials, taken together. Thus, for example, the one or more carbon raw materials, taken together, can have a biobased content of ≥80% as measured in accordance with ASTM D6866-12. This can be accomplished, for example, by including at least one carbon raw material corresponding to a renewable resource, e.g. glucose, levoglucosan, sucrose, lactose, fructose, xylose, maltose, arabinose, and mixtures thereof, such that the biobased content of the renewable resource is 100% and that ≥80% of the weight (mass) of the total organic carbon of the one or more carbon raw materials corresponds to the renewable resource. The one or more carbon raw materials, taken together, can have, for example, a biobased content of ≥95%, ≥99%, or 100%.

The method can also comprise isolating the polyhydroxyalkanoate copolymer molecules from the organism, such that the polyhydroxyalkanoate copolymer composition is substantially free of the organism. Suitable exemplary approaches for such isolation are known in the art.

A polyhydroxyalkanoate copolymer composition made in accordance with the methods described above is also provided. The polyhydroxyalkanoate copolymer composition can be one, for example, comprising a plurality of polyhydroxyalkanoate copolymer molecules, wherein the polyhydroxyalkanoate copolymer molecules (i) comprise 3-hydroxybutyrate monomers and 4-hydroxybutyrate monomers, (ii) have a monomeric molar percentage of 4-hydroxybutyrate monomers of 23.5 to 75%, and (iii) have a biobased content of ≥80%. Moreover, the polyhydroxyalkanoate composition can be one, for example, wherein (a) the monomeric molar percentage of 4-hydroxybutyrate monomers of the polyhydroxyalkanoate copolymer molecules is 25 to 70%, 30 to 40%, 40 to 50%, 50 to 60%, or 60 to 70%, (b) the biobased content of the polyhydroxyalkanoate copolymer molecules is ≥95%, ≥99%, or 100%, (c) the polyhydroxyalkanoate copolymer molecules have a weight average molecular weight of 250 kDa to 2.0 MDa, 1.5 MDa to 2.0 MDa, or 1.7 MDa to 2.0 MDa, (d) the composition has a glass transition temperature of −60° C. to −5° C., −50° C. to −15° C., −50° C. to −20° C., or −45° C. to −15° C., (e) the monomeric molar percentage of 4-hydroxybutyrate monomers of the polyhydroxyalkanoate copolymer molecules does not decrease with increasing molecular weight of the polyhydroxyalkanoate copolymer molecules, and/or (f) the polyhydroxyalkanoate copolymer molecules are produced in a fermentation process using one or more carbon raw materials that, taken together, have a biobased content of ≥80%, as described above.

EXAMPLES

The present technology is further illustrated by the following examples, which should not be construed as limiting in any way. These examples describe a number of biotechnology tools and methods for the construction of strains that generate a product of interest. Suitable host strains, the potential source and a list of recombinant genes used in these examples, suitable extrachromosomal vectors, suitable strategies and regulatory elements to control recombinant gene expression, and a selection of construction techniques to overexpress genes in or inactivate genes from host organisms are described. These biotechnology tools and methods are well known to those skilled in the art.

Suitable Host Strains

In some embodiments, the host strain is *E. coli* K-12 strain LS5218 (Sprat et al., *J. Bacteriol.* 146 (3):1166-1169 (1981); Jenkins and Nunn, *J. Bacteriol.* 169 (1):42-52 (1987)) or strain MG1655 (Guyer et al., *Cold Spr. Harb. Symp. Quant. Biol.* 45:135-140 (1981)). Other suitable *E. coli* K-12 host strains include, but are not limited to, WG1 and W3110 (Bachmann *Bacteriol. Rev.* 36(4):525-57 (1972)). Alternatively, *E. coli* strain W (Archer et al., *BMC Genomics* 2011, 12:9 doi:10.1186/1471-2164-12-9) or *E. coli* strain B (Delbruck and Luria, Arch. Biochem. 1:111-141 (1946)) and their derivatives such as REL606 (Lenski et al., Am. Nat. 138:1315-1341 (1991)) are other suitable *E. coli* host strains.

Other exemplary microbial host strains include but are not limited to: *Ralstonia eutropha, Zoogloea ramigera, Allochromatium vinosum, Rhodococcus ruber, Delftia acidovorans, Aeromonas caviae, Synechocystis* sp. PCC 6803, *Synechococcus elongatus* PCC 7942, *Thiocapsa pfenigii, Bacillus megaterium, Acinetobacter baumannii, Acinetobacter baylyi, Clostridium kluyveri, Methylobacterium extorquens, Nocardia corralina, Nocardia salmonicolor, Pseudomonas fluorescens, Pseudomonas oleovorans, Pseudomonas* sp. 6-19, *Pseudomonas* sp. 61-3 and *Pseudomonas putida, Rhodobacter sphaeroides, Alcaligenes latus, Klebsiella oxytoca, Anaerobiospirillum succiniciproducens, Actinobacillus succinogenes, Mannheimia succiniciproducens, Rhizobium etli, Bacillus subtilis, Corynebacterium glutamicum, Gluconobacter oxydans, Zymomonas mobilis, Lactococcus lactis, Lactobacillus plantarum, Streptomyces coelicolor,* and *Clostridium acetobutylicum.* Exemplary yeasts or fungi include species selected from *Saccharomyces cerevisiae, Schizosaccharomyces pombe, Kluyveromyces lactis, Kluyveromyces marxianus, Aspergillus terreus, Aspergillus niger* and *Pichia pastoris.*

Exemplary algal strains include but are not limited to: *Chlorella* strains, species selected from: *Chlorella minutissima, Chlorella emersonii, Chlorella sorokiniana, Chlorella elhpsoidea, Chlorella* sp., or *Chlorella protothecoides.*

Source of Recombinant Genes

Sources of encoding nucleic acids for a PHB-co-4HB pathway enzyme can include, for example, any species where the encoded gene product is capable of catalyzing the referenced reaction. Such species include both prokaryotic and eukaryotic organisms including, but not limited to, bacteria, including archaea and eubacteria, and eukaryotes, including yeast, plant, insect, animal, and mammal, including human. Exemplary species for such sources include, for example, *Escherichia coli, Saccharomyces cerevisiae, Saccharomyces kluyveri, Synechocystis* sp. PCC 6803, *Synechococcus elongatus* PCC 7942, *Synechococcus* sp. PCC 7002, *Chlorogleopsis* sp. PCC 6912, *Chloroflexus aurantiacus, Clostridium kluyveri, Clostridium acetobutylicum, Clostridium beijerinckii, Clostridium saccharoperbutylacetonicum, Clostridium perjringens, Clostridium difficile, Clostridium botulinum, Clostridium tyrobutyricum, Clostridium tetanomorphum, Clostridium tetani, Clostridium propionicum, Clostridium aminobutyricum, Clostridium subterminale, Clostridium sticklandii, Ralstonia eutropha, Mycobacterium bovis, Mycobacterium tuberculosis, Porphyromonas gingivalis, Arabidopsis thaliana, Thermus thermophilus, Pseudomonas* species, including *Pseudomonas aeruginosa, Pseudomonas putida, Pseudomonas stutzeri, Pseudomonas fluorescens, Chlorella minutissima, Chlorella emersonii, Chlorella sorokiniana, Chlorella ellipsoidea, Chlorella* sp., *Chlorella protothecoides, Homo sapiens, Oryctolagus cuniculus, Rhodobacter sphaeroides, Thermoanaerobacter brockii, Metallosphaera sedula, Leuconostoc mesenteroides, Roseiflexus castenholzii, Erythrobacter, Simmondsia chinensis, Acinetobacter* species, including *Acinetobacter calcoaceticus* and *Acinetobacter baylyi, Sulfolobus tokodaii, Sulfolobus solfataricus, Sulfolobus acidocaldarius, Bacillus subtilis, Bacillus cereus, Bacillus megaterium, Bacillus brevis, Bacillus pumilus, Rattus norvegicus, Klebsiella pneumonia, Klebsiella oxytoca, Euglena gracilis, Treponema denticola, Moorella thermoacetica, Thermotoga maritima, Halobacterium salinarum, Geobacillus stearothermophilus, Aeropyrum pernix, Sus scrofa, Caenorhabditis elegans, Corynebacterium glutamicum, Acidaminococcus fermentans, Lactococcus lactis, Lactobacillus plantarum, Streptococcus thermophilus, Enterobacter aerogenes, Candida* sp., *Aspergillus terreus, Pedicoccus pentosaceus, Zymomonas mobilus, Acetobacter pasteurians, Kluyveromyces lactis, Eubacterium barkeri, Bacteroides capillosus, Anaerotruncus colihominis, Natranaerobius thermophilus, Campylobacter jejuni, Haemophilus influenzae, Serratia marcescens, Citrobacter amalonaticus, Myxococcus xanthus, Fusobacterium nuleatum, Penicillium chrysogenum,* marine gamma proteobacterium, and butyrate-producing bacterium. For example, microbial hosts (e.g., organisms) having PHB-co-4HB biosynthetic production are exemplified herein with reference to an *E. coli* host. However, with the complete genome sequence available for now more than 550 species (with more than half of these available on public databases such as the NCBI), including 395 microorganism genomes and a variety of yeast, fungi, plant, and mammalian genomes, the identification of genes encoding the requisite PHB-co-4HB biosynthetic activity for one or more genes in related or distant species, including for example, homologues, orthologs, paralogs and nonorthologous gene displacements of known genes, and the interchange of genetic alterations between organisms is routine and well known in the art. Accordingly, the metabolic alterations enabling biosynthesis of PHB-co-4HB and other compounds of the disclosure herein with reference to a particular organism such as E. coli can be readily applied to other microorganisms, including prokaryotic and eukaryotic organisms alike. Given the teachings and guidance provided herein, those skilled in the art will know that a metabolic alteration exemplified in one organism can be applied equally to other organisms.

Production of Transgenic Host for Producing 4HB

Transgenic (recombinant) hosts for producing PHB-co-4HB are genetically engineered using conventional techniques known in the art. The genes cloned and/or assessed for host strains producing PHB-co-4HB are presented below in Table 1A, along with the appropriate Enzyme Commission number (EC number) and references. Some genes were synthesized for codon optimization while others were cloned via PCR from the genomic DNA of the native or wild-type host. As used herein, "heterologous" means from another host. The host can be the same or different species. FIG. 1 is an exemplary pathway for producing PHB-co-4HB.

TABLE 1A

Genes overproduced or deleted in microbial host strains producing PHB-co-4HB, in accordance with FIG. 1. A star (*) after the gene name denotes that the nucleotide sequence was optimized for expression in E. coli.

| Reaction number (FIG. 1) | Gene Name | Enzyme Name | EC Number | Accession No. or Reference |
|---|---|---|---|---|
| 1 | phaA5 | Acetyl-CoA acetyltransferase (a.k.a. beta-ketothiolase) | 2.3.1.9 | 2VU2_A |
| 2 | phaB5 | Acetoacetyl-CoA reductase | 1.1.1.36 | P23238 |
| 3 | sucD* | Succinate semialdehyde dehydrogenase | 1.2.1.76 | Gene/Protein ID 1; U.S. Patent Appl. No. 2011/024612 |
| 4 | kgdM | Alpha-ketoglutarate decarboxylase | 4.1.1.71 | NP_335730 |
| 4 | kgdP | Alpha-ketoglutarate decarboxylase | 4.1.1.n | YP_004335105 |
| 4 | kgdS | 2-Oxoglutarate decarboxylase | 4.1.1.n | ACB00744.1 |
| 5 | ssaR$_{At}$* | Succinic semialdehyde reductase | 1.1.1.61 | Gene/Protein ID 2; U.S. Patent Appl. No. 2011/024612 |
| 5 | fucO$_{I6L-L7V}$ | L-1,2-propanediol oxidoreductase | 1.1.1.77 | Gene/Protein ID 3 |
| 6 | orfZ | CoA transferase | 2.8.3.n | AAA92344 |
| 6 | orfZ150 | CoA transferase | 2.8.3.n | NP_904965 |
| 7 | buk1 | Butyrate kinase I | 2.7.2.7 | NP_349675 |
| 7 | buk2 | Butyrate kinase II | 2.7.2.7 | NP_348286 |
| 8 | ptb | Phosphotransbutyrylase | 2.3.1.19 | NP_349676 |
| 9 | phaC3/C5 | Polyhydroxyalkanoate synthase fusion protein | 2.3.1.n | Gene/Protein ID 4; U.S. Pat. No. 6,316,262; U.S. Patent Appl. No. 20100168481 A1 |
| 9 | phaC3/C1* | Polyhydroxyalkanoate synthase fusion protein | 2.3.1.n | Gene/Protein ID 5; U.S. Patent Appl. No. 2011/024612 |
| 9 | phaC3/C33 | Polyhydroxyalkanoate synthase fusion protein | 2.3.1.n | Gene/Protein ID 6 |
| 10 | yneI | Succinate-semialdehyde dehydrogenase, NAD+-dependent | 1.2.1.24 | NP_416042 |
| 10 | gabD | Succinate-semialdehyde dehydrogenase, NADP+-dependent | 1.2.1.16 | NP_417147 |
| 10 | astD | Aldehyde dehydrogenase | 1.2.1.71 | NP_416260 |
| 11 | ppc$_{Ec}$ | Phosphoenolpyruvate carboxylase | 4.1.1.31 | NP_418391 |
| 12 | tesA | Multifunctional acyl-CoA thioesterase I and protease I and lysophospholipase L1 | 3.1.1.5, 3.1.2.14 | NP_415027 |
| 12 | tesB | Thioesterase II | 3.1.2.20 | ZP_08342109 |
| 12 | yciA | Acyl-CoA thioesterase | 3.1.2.20 | NP_415769 |

Other proteins capable of catalyzing the reactions listed in Table 1A can be discovered by consulting the scientific literature, patents, BRENDA searches (http://www.brenda-enzymes.info/), and/or by BLAST searches against e.g., nucleotide or protein databases at NCBI (www.ncbi.nlm.nih.gov/). Synthetic genes can then be created to provide an easy path from sequence databases to physical DNA. Such synthetic genes are designed and fabricated from the ground up, using codons to enhance heterologous protein expression, and optimizing characteristics needed for the expression system and host. Companies such as e.g., DNA 2.0 (Menlo Park, Calif. 94025, USA) will provide such routine service. Proteins that may catalyze some of the biochemical reactions listed in Table 1A are provided in Tables 1B through 1X.

TABLE 1B

Suitable homologues for the PhaA5 protein (beta-ketothiolase, from *Zoogloea ramigera*, EC No. 2.3.1.9, which acts on acetyl-CoA + acetyl-CoA to produce acetoacetyl-CoA; protein acc. no. 2VU2_A).

| Protein Name | Protein Accession No. |
| --- | --- |
| acetyl-CoA acetyltransferase | YP_002827756 |
| acetyl-CoA acetyltransferase | YP_002283310 |
| acetyl-CoA acetyltransferase | YP_002733453 |
| acetyl-CoA acetyltransferase | ZP_01011874 |
| acetyl-CoA acetyltransferase | ZP_00961105 |
| acetyl-CoA acetyltransferase | YP_426557 |
| acetyl-Coenzyme A acetyltransferase 3 | NP_694791 |
| acetyl-CoA acetyltransferase | YP_003153095 |
| Acetyl-CoA acetyltransferase | CCF95917 |
| acetyl-CoA acetyltransferase | ZP_07454459 |

TABLE 1C

Suitable homologues for the PhaB5 protein (acetoacetyl-CoA reductase, from *Zoogloea ramigera*, EC No. 1.1.1.36, which acts on acetoacetyl-CoA to produce 3-hydroxybutyryl-CoA; protein acc. no. P23238).

| Protein Name | Protein Accession No. |
| --- | --- |
| acetoacetyl-CoA reductase | YP_002827755 |
| phaB gene product | YP_770184 |
| acetoacetyl-CoA reductase | ZP_08627619 |
| molybdopterin-guanine dinucleotide biosynthesis protein A | ZP_01901796 |
| acetoacetyl-CoA reductase | YP_006369576 |
| putative acetoacetyl-CoA reductase PhaB | ZP_09394630 |
| acetoacetyl-CoA reductase | YP_001352246 |
| acetoacetyl-CoA reductase | ZP_02467262 |
| acetoacetyl-CoA reductase | ZP_01985557 |

TABLE 1D

Suitable homologues for the SucD protein (succinate semialdehyde dehydrogenase, from *Clostridium kluyveri*, EC No. 1.2.1.76, which acts on succinyl-CoA to produce succinate semialdehyde; protein acc. no. YP_001396394).

| Protein Name | Protein Accession No. |
| --- | --- |
| CoA-dependent succinate semialdehyde dehydrogenase | AAA92347 |
| succinate-semialdehyde dehydrogenase [NAD(P)+] | ZP_06559980 |
| succinate-semialdehyde dehydrogenase [NAD(P)+] | ZP_05401724 |
| aldehyde-alcohol dehydrogenase family protein | ZP_07821123 |

TABLE 1D-continued

Suitable homologues for the SucD protein (succinate semialdehyde dehydrogenase, from *Clostridium kluyveri*, EC No. 1.2.1.76, which acts on succinyl-CoA to produce succinate semialdehyde; protein acc. no. YP_001396394).

| Protein Name | Protein Accession No. |
| --- | --- |
| succinate-semialdehyde dehydrogenase [NAD(P)+] | ZP_06983179 |
| succinate-semialdehyde dehydrogenase | YP_001928839 |
| hypothetical protein CLOHYLEM_05349 | ZP_03778292 |
| succinate-semialdehyde dehydrogenase [NAD(P)+] | YP_003994018 |
| succinate-semialdehyde dehydrogenase | NP_904963 |

TABLE 1E

Suitable homologues for the KgdM protein (alpha-ketoglutarate decarboxylase, from *Mycobacterium tuberculosis*, EC No. 4.1.1.71, which acts on alpha-ketoglutarate to produce succinate semialdehyde and carbon dioxide; protein acc. no. NP_335730).

| Protein Name | Protein Accession No. |
| --- | --- |
| alpha-ketoglutarate decarboxylase | YP_001282558 |
| alpha-ketoglutarate decarboxylase | NP_854934 |
| 2-oxoglutarate dehydrogenase sucA | ZP_06454135 |
| 2-oxoglutarate dehydrogenase sucA | ZP_04980193 |
| alpha-ketoglutarate decarboxylase | NP_961470 |
| alpha-ketoglutarate decarboxylase Kgd | YP_001852457 |
| alpha-ketoglutarate decarboxylase | NP_301802 |
| alpha-ketoglutarate decarboxylase | ZP_05215780 |
| alpha-ketoglutarate decarboxylase | YP_001702133 |

TABLE 1F

Suitable homologues for the KgdP protein (Alpha-ketoglutarate decarboxylase, from *Pseudonocardia dioxanivorans* CB1190, EC No. 4.1.1.n, which acts on alpha-ketoglutarate to produce succinate semialdehyde and carbon dioxide; protein acc. no. YP_004335105).

| Protein Name | Protein Accession No. |
| --- | --- |
| alpha-ketoglutarate decarboxylase | ZP_08119245 |
| 2-oxoglutarate dehydrogenase, E1 component | ZP_09743222 |
| alpha-ketoglutarate decarboxylase | YP_705947 |
| alpha-ketoglutarate decarboxylase | NP_961470 |
| alpha-ketoglutarate decarboxylase | ZP_08024348 |
| alpha-ketoglutarate decarboxylase | YP_003343675 |
| kgd gene product | NP_737800 |
| 2-oxoglutarate dehydrogenase complex, dehydrogenase (E1) component | YP_004223349 |
| oxoglutarate dehydrogenase (succinyl-transferring), E1 component | EJF35718 |

TABLE 1G

Suitable homologues for the KgdS protein (2-oxoglutarate decarboxylase, from *Synechococcus* sp. PCC 7002, EC No. 4.1.1.n, which acts on alpha-ketoglutarate to produce succinate semialdehyde and carbon dioxide; protein acc. no. ACB00744.1).

| Protein Name | Protein Accession No. |
| --- | --- |
| alpha-ketoglutarate decarboxylase | YP_001282558 |
| alpha-ketoglutarate decarboxylase | NP_854934 |
| 2-oxoglutarate dehydrogenase sucA | ZP_06454135 |
| 2-oxoglutarate dehydrogenase sucA | ZP_04980193 |
| alpha-ketoglutarate decarboxylase | NP_961470 |
| alpha-ketoglutarate decarboxylase Kgd | YP_001852457 |

TABLE 1G-continued

Suitable homologues for the KgdS protein (2-oxoglutarate decarboxylase, from *Synechococcus* sp. PCC 7002, EC No. 4.1.1.n, which acts on alpha-ketoglutarate to produce succinate semialdehyde and carbon dioxide; protein acc. no. ACB00744.1).

| Protein Name | Protein Accession No. |
| --- | --- |
| alpha-ketoglutarate decarboxylase | NP_301802 |
| alpha-ketoglutarate decarboxylase | ZP_05215780 |
| alpha-ketoglutarate decarboxylase | YP_001702133 |

TABLE 1H

Suitable homologues for the SsaR$_{At}$ protein (succinic semialdehyde reductase, from *Arabidopsis thaliana*, EC No. 1.1.1.61, which acts on succinate semialdehyde to produce 4-hydroxybutyrate; protein acc. no. AAK94781).

| Protein Name | Protein Accession No. |
| --- | --- |
| 6-phosphogluconate dehydrogenase NAD-binding domain-containing protein | XP_002885728 |
| hypothetical protein isoform 1 | XP_002266252 |
| predicted protein | XP_002320548 |
| hypothetical protein isoform 2 | XP_002266296 |
| unknown | ACU22717 |
| 3-hydroxyisobutyrate dehydrogenase, putative | XP_002524571 |
| unknown | ABK22179 |
| unknown | ACJ85049 |
| predicted protein | XP_001784857 |

TABLE 1I

Suitable homologues for the FucO$_{I6L\_L7V}$ protein (L-1,2-propanediol oxidoreductase, from *Escherichia coli* str. K-12 substr. MG1655, EC No. 1.1.1.77, which acts on succinate semialdehyde to produce 4-hydroxybutyrate).

| Protein Name | Protein Accession No. |
| --- | --- |
| L-1,2-propanediol oxidoreductase | YP_001459571 |
| lactaldehyde reductase | ZP_12475782 |
| L-1,2-propanediol oxidoreductase | YP_001455658 |
| lactaldehyde reductase | ZP_17109585 |
| L-1,2-propanediol oxidoreductase | YP_003294352 |
| L-1,2-propanediol oxidoreductase | YP_002988900 |
| L-1,2-propanediol oxidoreductase | ZP_09185179 |
| lactaldehyde reductase | ZP_06759418 |
| alcohol dehydrogenase | ZP_05943499 |

TABLE 1J

Suitable homologues for the OrfZ protein (CoA transferase, from *Clostridium kluyveri* DSM 555, EC No. 2.8.3.n, which acts on 4-hydroxybutyrate to produce 4-hydroxybutyryl CoA; protein acc. no. AAA92344).

| Protein Name | Protein Accession No. |
| --- | --- |
| 4-hydroxybutyrate coenzyme A transferase | YP_001396397 |
| acetyl-CoA hydrolase/transferase | ZP_05395303 |
| acetyl-CoA hydrolase/transferase | YP_001309226 |
| 4-hydroxybutyrate coenzyme A transferase | NP_781174 |
| 4-hydroxybutyrate coenzyme A transferase | ZP_05618453 |
| acetyl-CoA hydrolase/transferase | ZP_05634318 |
| 4-hydroxybutyrate coenzyme A transferase | ZP_00144049 |
| hypothetical protein ANASTE_01215 | ZP_02862002 |
| 4-hydroxybutyrate coenzyme A transferase | ZP_07455129 |

TABLE 1K

Suitable homologues for the OrfZ150 protein (CoA transferase, from *Porphyromonas gingivalis* W83, EC No. 2.8.3.n, which acts on 4-hydroxybutyrate to produce 4-hydroxybutyryl CoA; protein acc. no. NP_904965).

| Protein Name | Protein Accession No. |
| --- | --- |
| 4-hydroxybutyrate CoA-transferase | YP_005014371 |
| hypothetical protein FUAG_02467 | ZP_10973595 |
| acetyl-CoA hydrolase/transferase | ZP_10325539 |
| 4-hydroxybutyrate coenzyme A transferase | ZP_10895308 |
| 4-hydroxybutyrate CoA-transferase | ZP_15973607 |
| acetyl-CoA hydrolase/transferase | YP_003639307 |
| 4-hydroxybutyrate coenzyme A transferase | ZP_08514074 |
| succinyl:benzoate coenzyme A transferase | YP_006721017 |
| 4-hydroxybutyrate CoA-transferase | YP_003961374 |

TABLE 1L

Suitable homologues for the Buk1 protein (butyrate kinase I, from *Clostridium acetobutylicum* ATCC824, EC No. 2.7.2.7, which acts on 4-hydroxybutyrate to produce 4-hydroxybutyryl phosphate).

| Protein Name | Protein Accession No. |
| --- | --- |
| butyrate kinase | YP_001788766 |
| butyrate kinase | YP_697036 |
| butyrate kinase | YP_003477715 |
| butyrate kinase | YP_079736 |
| acetate and butyrate kinase | ZP_01667571 |
| butyrate kinase | YP_013985 |
| butyrate kinase | ZP_04670620 |
| butyrate kinase | ZP_04670188 |
| butyrate kinase | ZP_07547119 |

TABLE 1M

Suitable homologues for the Buk2 protein (butyrate kinase II, from *Clostridium acetobutylicum* ATCC824, EC No. 2.7.2.7, which acts on acts on 4-hydroxybutyrate to produce 4-hydroxybutyryl phosphate).

| Protein Name | Protein Accession No. |
| --- | --- |
| butyrate kinase | YP_001311072 |
| hypothetical protein CLOSPO_00144 | ZP_02993103 |
| hypothetical protein COPEUT_01429 | ZP_02206646 |
| butyrate kinase | EFR5649 |
| butyrate kinase | ZP_0720132 |
| butyrate kinase | YP_0029418 |
| butyrate kinase | YP_002132418 |
| butyrate kinase | ZP_05389806 |
| phosphate butyryltransferase | ADQ27386 |

TABLE 1N

Suitable homologues for the Ptb protein (phosphotrans-butyrylase, from *Clostridium acetobutylicum* ATCC824, EC No. 2.3.1.19, which acts on 4-hydroxybutyryl phosphate to produce 4-hydroxybutyryl CoA).

| Protein Name | Protein Accession No. |
| --- | --- |
| phosphate butyryltransferase | YP_001884531 |
| hypothetical protein COPCOM_01477 | ZP_03799220 |
| phosphate butyryltransferase | YP_00331697 |
| phosphate butyryltransferase | YP_004204177 |
| phosphate acetyl/butyryltransferase | ZP_05265675 |
| putative phosphate acetyl/butyryltransferase | ZP_05283680 |

TABLE 1N-continued

Suitable homologues for the Ptb protein (phosphotrans-butyrylase, from *Clostridium acetobutylicum* ATCC824, EC No. 2.3.1.19, which acts on 4-hydroxybutyryl phosphate to produce 4-hydroxybutyryl CoA).

| Protein Name | Protein Accession No. |
|---|---|
| bifunctional enoyl-CoA hydratase/phosphate acetyltransferase | YP_426556 |
| hypothetical protein CLOBOL_07039 | ZP_02089466 |
| phosphate butyryltransferase | YP_003564887 |

TABLE 1O

Suitable homologues for the PhaC3/C5 protein (Polyhydro- xyalkanoate synthase fusion protein from *Pseudomonas putida* and *Zoogloea ramigera*, EC No. 2.3.1.n, which acts on (R)-3-hydroxybutyryl-CoA or or 4-hydroxybutyryl-CoA + [(R)-3-hydroxybutanoate-co-4-hydroxybutanoate]$_n$ to produce [(R)-3-hydroxybutanoate-co-4-hydroxybutanoate]$_{(n+1)}$ + CoA and also acts on 4-hydroxybutyryl-CoA + [4-hydroxybutanoate]$_n$ to produce [4-hydroxybutanoate]$_{(n+1)}$ + CoA.

| Protein Name | Protein Accession No. |
|---|---|
| PHB polymerase | AAB06755 |
| polyhydroxyalkanoic acid synthase | ZP_10443466 |
| poly(R)-hydroxyalkanoic acid synthase, class I | ZP_10719804 |
| poly(3-hydroxybutyrate) polymerase PhaC | YP_004685292 |
| poly(R)-hydroxyalkanoic acid synthase, class I | ZP_02382303 |
| poly-beta-hydroxybutyrate polymerase | YP_003977718 |
| phaC2 gene product | YP_583821 |
| poly(R)-hydroxyalkanoic acid synthase | YP_001003639 |
| poly(R)-hydroxyalkanoic acid synthase | YP_283333 |

TABLE 1P

Suitable homologues for the PhaC3/C1 protein (Polyhydroxy-alkanoate synthase fusion protein from *Pseudomonas putida* and *Ralstonia eutropha* JMP134, EC No. 2.3.1.n, which acts on (R)-3-hydroxybutyryl-CoA or 4-hydroxybutyryl-CoA + [(R)-3-hydroxybutanoate-co-4-hydroxybutanoate]$_n$ to produce [(R)-3-hydroxybutanoate-co-4-hydroxybutanoate]$_{(n+1)}$ + CoA and also acts on 4-hydroxybutyryl-CoA + [4-hydroxybutanoate]$_n$ to produce [4-hydroxybutanoate]$_{(n+1)}$ + CoA.

| Protein Name | Protein Accession No. |
|---|---|
| Poly(R)-hydroxyalkanoic acid synthase, class I | YP_295561 |
| Poly(3-hydroxybutyrate) polymerase | YP_725940 |
| polyhydroxyalkanoic acid synthase | AAW65074 |
| polyhydroxyalkanoic acid synthase | YP_002005374 |
| Poly(R)-hydroxyalkanoic acid synthase, class I | YP_583508 |
| intracellular polyhydroxyalkanoate synthase | ADM24646 |
| Poly(3-hydroxyalkanoate) polymerase | ZP_00942942 |
| polyhydroxyalkanoic acid synthase | YP_003752369 |
| PhaC | AAF23364 |

TABLE 1Q

Suitable homologues for the PhaC3/C33 protein (Polyhydroxy-alkanoate synthase fusion protein from *Pseudomonas putida* and *Delftia acidovorans* 89-11-102, EC No. 2.3.1.n, which acts on (R)-3-hydroxybutyryl-CoA or 4-hydroxybutyryl-CoA + [(R)-3-hydroxybutanoate-co-4-hydroxybutanoate]$_n$ to produce [(R)-3-hydroxybutanoate-co-4-hydroxybutanoate]$_{(n+1)}$ + CoA and also acts on 4-hydroxybutyryl-CoA + [4-hydroxybutanoate]$_n$ to produce [4-hydroxybutanoate]$_{(n+1)}$ + CoA.

| Protein Name | Protein Accession No. |
|---|---|
| polyhydroxybutyrate synthase | AAL17611 |
| poly(R)-hydroxyalkanoic acid synthase, class I | ZP_04764634 |

TABLE 1Q-continued

Suitable homologues for the PhaC3/C33 protein (Polyhydroxy-alkanoate synthase fusion protein from *Pseudomonas putida* and *Delftia acidovorans* 89-11-102, EC No. 2.3.1.n, which acts on (R)-3-hydroxybutyryl-CoA or 4-hydroxybutyryl-CoA + [(R)-3-hydroxybutanoate-co-4-hydroxybutanoate]$_n$ to produce [(R)-3-hydroxybutanoate-co-4-hydroxybutanoate]$_{(n+1)}$ + CoA and also acts on 4-hydroxybutyryl-CoA + [4-hydroxybutanoate]$_n$ to produce [4-hydroxybutanoate]$_{(n+1)}$ + CoA.

| Protein Name | Protein Accession No. |
|---|---|
| poly-beta-hydroxybutyrate polymerase protein | CAQ36337 |
| poly-beta-hydroxybutyrate polymerase | YP_004360851 |
| poly(R)-hydroxyalkanoic acid synthase, class I | ZP_08961344 |
| poly(R)-hydroxyalkanoic acid synthase | YP_983028 |
| polyhydroxyalkanoic acid synthase | EGF41868 |
| Poly-beta-hydroxybutyrate polymerase | ZP_02489627 |
| polyhydroxyalkanoate synthase | ABN71571 |

TABLE 1R

Suitable homologues for the YneI (Sad) protein (succinate semialdehyde dehydrogenase, NAD+-dependent, from *Escherichia coli* str. K-12 substr. MG1655, EC No. 1.2.1.24, which acts on glutarate semialdehyde (succinic semialdehyde) to produce glutarate (succinate); Protein acc. no. NP_416042 (Fuhrer et al., J Bacteriol. 2007 November; 189(22): 8073-8. Dennis and Valentin, U.S. Pat. No. 6,117,658)).

| Protein Name | Protein Accession No. |
|---|---|
| succinate semialdehyde dehydrogenase | NP_805238 |
| putative aldehyde dehydrogenase | YP_002919404 |
| aldehyde dehydrogenase | NP_745295 |
| aldehyde dehydrogenase | ZP_03269266 |
| aldehyde dehydrogenase | ZP_05726943 |
| aldehyde dehydrogenase | YP_001906721 |
| hypothetical protein | BAF01627 |
| aldehyde dehydrogenase | ZP_03739186 |
| succinate-semialdehyde dehydrogenase | NP_637690 |

TABLE 1S

Suitable homologues for the GabD protein (succinate semialdehyde dehydrogenase, NADP+-dependent, from *Escherichia coli* str. K-12 substr. MG1655, EC No. 1.2.1.20, which acts on glutarate semialdehyde (or succinic semialdehyde) to produce glutarate (or succinate); Protein acc. no. NP_417147 (Riley et al., Nucleic Acids Res. 34 (1), 1-9 (2006))).

| Protein Name | Protein Accession No. |
|---|---|
| succinate-semialdehyde dehydrogenase I | ZP_05433422 |
| succinate-semialdehyde dehydrogenase (NAD(P)(+)) | YP_001744810 |
| hypothetical protein CIT292_04137 | ZP_03838093 |
| succinate-semialdehyde dehydrogenase | YP_002638371 |
| succinate-semialdehyde dehydrogenase I | YP_001333939 |
| succinate-semialdehyde dehydrogenase I | NP_742381 |
| succinate-semialdehyde dehydrogenase [NADP+] (ssdh) | YP_002932123 |
| succinic semialdehyde dehydrogenase | YP_001951927 |
| succinate semialdehyde dehydrogenase | YP_298405 |

TABLE 1T

Suitable homologues for the AstD protein (aldehyde dehydrogenase from *Escherichia coli* K-12 substr. MG1655, EC No. 1.2.1.71, which acts on succinate semialdehyde to produce succinate); Protein acc. no. NP_416260.

| Protein Name | Protein Accession No. |
| --- | --- |
| succinylglutamic semialdehyde dehydrogenase | YP_002382476 |
| hypothetical protein D186_18882 | ZP_16280274 |
| succinylglutamic semialdehyde dehydrogenase | YP_003942089 |
| succinylglutamate-semialdehyde dehydrogenase | ZP_16225314 |
| succinylglutamic semialdehyde dehydrogenase AstD | YP_005933902 |
| succinylglutamic semialdehyde dehydrogenase | YP_005431041 |
| succinylglutamic semialdehyde dehydrogenase | ZP_10352779 |
| succinylglutamic semialdehyde dehydrogenase | ZP_10036944 |
| succinylglutamic semialdehyde dehydrogenase | YP_004730031 |

TABLE 1U

Suitable homologues for the Ppc protein (phosphoenolpyruvate carboxylase, from *Escherichia coli* str. K-12 substr. MG1655, EC No. 4.1.1.31, which acts on phosphoenolpyruvate and carbon dioxide to produce oxaloacetate; protein acc. no. NP_418391).

| Protein Name | Protein Accession No. |
| --- | --- |
| phosphoenolpyruvate carboxylase | ZP_02904134 |
| phosphoenolpyruvate carboxylase | YP_002384844 |
| phosphoenolpyruvate carboxylase | YP_003367228 |
| phosphoenolpyruvate carboxylase | ZP_02345134 |
| phosphoenolpyruvate carboxylase | ZP_04558550 |
| phosphoenolpyruvate carboxylase | YP_003615503 |
| phosphoenolpyruvate carboxylase | YP_002241183 |
| phosphoenolpyruvate carboxylase | CBK84190 |
| phosphoenolpyruvate carboxylase | YP_003208553 |

TABLE 1V

Suitable homologues for the TesA protein (multifunctional acyl-CoA thioesterase I and protease I and lysophospholipase L1, from *Escherichia coli* K-12 substr. MG1655, EC No. 3.1.1.5 and 3.1.2.14, which acts on 4-hydroxybutyryl-CoA to produce 4-hydroxybutyrate; protein acc. no. NP_415027).

| Protein Name | Protein Accession No. |
| --- | --- |
| multifunctional acyl-CoA thioesterase I/protease I/lysophospholipase L1 | ZP_16276771 |
| multifunctional acyl-CoA thioesterase I/protease I/lysophospholipase L1 | YP_001175703 |
| tesA; acyl-CoA thioesterase I | ZP_06549555 |
| Arylesterase precursor | ZP_16338589 |
| multifunctional acyl-CoA thioesterase I/protease I/lysophospholipase L1 | YP_006343946 |
| lysophospholipase | YP_002986681 |
| multifunctional acyl-CoA thioesterase I and protease I and lysophospholipase L1 | YP_049328 |
| multifunctional acyl-CoA thioesterase I and protease I and lysophospholipase L1 | ZP_10113091 |
| hypothetical protein PROSTU_03568 | ZP_02997848 |

TABLE 1W

Suitable homologues for the TesB protein (thioesterase II, from *Escherichia coli* K-12 substr. MG1655, EC No. 3.1.2.20, which acts on 4-hydroxybutyryl-CoA to produce 4-hydroxybutyrate; protein acc. no. ZP_08342109).

| Protein Name | Protein Accession No. |
| --- | --- |
| acyl-CoA thioesterase II | ZP_09460164 |
| acyl-CoA thioesterase | NP_455062 |
| acyl-CoA thioesterase II | ZP_10490626 |
| acyl-CoA thioesterase II TesB | YP_005196718 |
| acyl-CoA thioesterase II | YP_002649594 |
| acyl-CoA thioesterase II (TEII) | NP_931060 |
| Acyl-CoA thioesterase II | ZP_01217095 |
| acyl-CoA thioesterase II | ZP_10142747 |
| acyl-CoA thioesterase II | ZP_10354000 |

TABLE 1X

Suitable homologues for the YciA protein (acyl-CoA thioesterase, from *Escherichia coli* K-12 substr. MG1655, EC No. 3.1.2.20, which acts on 4-hydroxybutyryl-CoA to produce 4-hydroxybutyrate; protein acc. no. NP_415769).

| Protein Name | Protein Accession No. |
| --- | --- |
| acyl-CoA thioester hydrolase | YP_002382845 |
| acyl-CoA thioester hydrolase | YP_001570262 |
| thioesterase superfamily protein | YP_005019613 |
| acyl-CoA thioester hydrolase | YP_050409 |
| acyl-CoA thioester hydrolase | YP_002151085 |
| acyl-CoA thioester hydrolase YciA | NP_777876 |
| hypothetical protein VC1701 | NP_231337 |
| thioesterase superfamily protein | YP_002893359 |
| acyl-CoA thioester hydrolase | ZP_11128814 |

Suitable Extrachromosomal Vectors and Plasmids

A "vector," as used herein, is an extrachromosomal replicon, such as a plasmid, phage, or cosmid, into which another DNA segment may be inserted so as to bring about the replication of the inserted segment. Vectors vary in copy number, depending on their origin of replication, and size. Vectors with different origins of replication can be propagated in the same microbial cell unless they are closely related such as pMB1 and ColE1. Suitable vectors to express recombinant proteins can constitute pUC vectors with a pMB1 origin of replication having 500-700 copies per cell, pBluescript vectors with a ColE1 origin of replication having 300-500 copies per cell, pBR322 and derivatives with a pMB1 origin of replication having 15-20 copies per cell, pACYC and derivatives with a p15A origin of replication having 10-12 copies per cell, and pSC101 and derivatives with a pSC101 origin of replication having about 5 copies per cell as described in the QIAGEN® Plasmid Purification Handbook (found on the world wide web at: //kirshner.med-.harvard.edu/files/protocols/QIAGEN_QIAGENPlasmid-Purification_EN.pdf). A widely used vector is pSE380 that allows recombinant gene expression from an IPTG-inducible trc promoter (Invitrogen, La Jolla, Calif.).

Suitable Strategies and Expression Control Sequences for Recombinant Gene Expression Strategies for achieving expression of recombinant genes in *E. coli* have been extensively described in the literature (Gross, Chimica Oggi 7(3):21-29 (1989); Olins and Lee, Cur. Op. Biotech. 4:520-525 (1993); Makrides, Microbiol. Rev. 60(3):512-538 (1996); Hannig and Makrides, Trends in Biotech. 16:54-60 (1998)). Expression control sequences can include constitutive and inducible promoters, transcription enhancers, transcription terminators, and the like which are well known in the art. Suitable promoters include, but are not limited to, $P_{lac}$, $P_{tac}$, $P_{trc}$, $P_R$, $P_L$, $P_{phoA}$, $P_{ara}$, $P_{uspA}$, $P_{rpsU}$, $P_{syn}$ (Rosenberg and Court, Ann. Rev. Genet. 13:319-353 (1979); Hawley and McClure, Nucl. Acids Res. 11 (8):2237-2255 (1983); Harley and Raynolds, Nucl. Acids Res. 15:2343-2361 (1987); also at the world wide web at ecocyc.org and partsregistry.org).

```
Exemplary promoters are:
                                          (SEQ ID NO: 1)
P_synA  (5'-TTGACAGCTAGCTCAGTCCTAGGTATAATGCTAGC-3'), (SEQ ID NO: 2)
P_synC  (5'-TTGACAGCTAGCTCAGTCCTAGGTACTGTGCTAGC-3'), (SEQ ID NO: 3)
P_synE  (5'-TTTACAGCTAGCTCAGTCCTAGGTATTATGCTAGC-3'), (SEQ ID NO: 4)
P_synH  (5'-CTGACAGCTAGCTCAGTCCTAGGTATAATGCTAGC-3'), (SEQ ID NO: 5)
P_synK  (5'-TTTACGGCTAGCTCAGTCCTAGGTACAATGCTAGC-3'), (SEQ ID NO: 6)
P_synM  (5'-TTGACAGCTAGCTCAGTCCTAGGGACTATGCTAGC-3'), (SEQ ID NO: 7)
P_x     (5'-TCGCCAGTCTGGCCTGAACATGATATAAAAT-3'), (SEQ ID NO: 8)
P_uspA  (5'-AACCACTATCAATATATTCATGTCGAAAATTTGTTTATCT

AACGAGTAAGCAAGGCGGATTGACGGATCATCCGGGTCGCTATAAGGTA

AGGATGGTCTTAACACTGAATCCTTACGGCTGGGTTAGCCCCGCGCACG

TAGTTCGCAGGACGCGGGTGACGTAACGGCACAAGAAACG-3'), (SEQ ID NO: 9)
P_rpsU  (5'-ATGCGGGTTGATGTAAAACTTTGTTCGCCCTGGAGAAAG

CCTCGTGTATACTCCTCACCCTTATAAAAGTCCCTTTCAAAAAAGGCCG

CGGTGCTTTACAAAGCAGCAGCAATTGCAGTAAAATTCCGCACCATTTT

GAAATAAGCTGGCGTTGATGCCAGCGGCAAAC-3'), (SEQ ID NO: 10)
P_synAF7 (5'-TTGACAGCTAGCTCAGTCCTAGGTACAGTGCTAGC-3'),
and (SEQ ID NO: 11)
P_synAF3 (5'-TTGACAGCTAGCTCAGTCCTAGGTACAATGCTAGC-3').
Exemplary terminators are:
                                          (SEQ ID NO: 12)
T_trpL  (5'-CTAATGAGCGGGCTTTTTTTGAACAAAA-3'), (SEQ ID NO: 13)
T_1006  (5-AAAAAAAAAAAACCCCGCTTCGGCGGGGTTTTTTTTT-3'), (SEQ ID NO: 14)
T_rrnB1 (5-ATAAAACGAAAGGCTCAGTCGAAAGACTGGGCCTTTCGTTTT AT-3'),
and (SEQ ID NO: 15)
T_rrnB2 (5-AGAAGGCCATCCTGACGGATGGCCTTTT-3').
```

Construction of Recombinant Hosts

Recombinant hosts containing the necessary genes that will encode the enzymatic pathway for the conversion of a carbon substrate to PHB-co-4HB may be constructed using techniques well known in the art.

Methods of obtaining desired genes from a source organism (host) are common and well known in the art of molecular biology. Such methods are described in, for example, Sambrook et al., *Molecular Cloning: A Laboratory Manual*, Third Ed., Cold Spring Harbor Laboratory, New York (2001); Ausubel et al., *Current Protocols in Molecular Biology*, John Wiley and Sons, Baltimore, Md. (1999). For example, if the sequence of the gene is known, the DNA may be amplified from genomic DNA using polymerase chain reaction (Mullis, U.S. Pat. No. 4,683,202) with primers specific to the gene of interest to obtain amounts of DNA suitable for ligation into appropriate vectors. Alternatively, the gene of interest may be chemically synthesized de novo in order to take into consideration the codon bias of the host organism to enhance heterologous protein expression. Expression control sequences such as promoters and transcription terminators can be attached to a gene of interest via polymerase chain reaction using engineered primers containing such sequences. Another way is to introduce the isolated gene into a vector already containing the necessary control sequences in the proper order by restriction endonuclease digestion and ligation. One example of this latter approach is the BioBrick™ technology (www.biobricks.org) where multiple pieces of DNA can be sequentially assembled together in a standardized way by using the same two restriction sites.

In addition to using vectors, genes that are necessary for the enzymatic conversion of a carbon substrate to PHB-co-4HB can be introduced into a host organism by integration into the chromosome using either a targeted or random approach. For targeted integration into a specific site on the chromosome, the method generally known as Red/ET recombineering is used as originally described by Datsenko and Wanner (*Proc. Natl. Acad. Sci. USA*, 2000, 97, 6640-6645). Random integration into the chromosome involves using a mini-Tn5 transposon-mediated approach as described by Huisman et al. (U.S. Pat. Nos. 6,316,262 and 6,593,116).

Culturing of Host to Produce PHB-co-4HB Biomass

In general, the recombinant host is cultured in a medium with a carbon source and other essential nutrients to produce the PHB-co-4HB biomass by fermentation techniques either in batches or using continuously operating methods known in the art. Additional additives can also be included, for example, antifoaming agents and the like for achieving desired growth conditions. Fermentation is particularly useful for large scale production. An exemplary method uses bioreactors for culturing and processing the fermentation broth to the desired product. Other techniques such as separation techniques can be combined with fermentation for large scale and/or continuous production.

As used herein, the term "feedstock" refers to a substance used as a carbon raw material in an industrial process. When used in reference to a culture of organisms such as microbial or algae organisms such as a fermentation process with cells, the term refers to the raw material used to supply a carbon or other energy source for the cells. Carbon sources useful for the production of PHB-co-4HB include simple, inexpensive sources, for example, glucose, levoglucosan, sucrose, lactose, fructose, xylose, maltose, arabinose, and the like alone or in combination. In other embodiments, the feedstock is molasses, starch, a fatty acid, a vegetable oil, a lignocellulosic material, and the like, again alone or in combination. In still other embodiments the feedstock can be ethanol, acetic acid, glycerol, and the like, alone or in combination. It is also possible to use organisms to produce the PHB-co-4HB biomass that grow on synthesis gas ($CO_2$, CO and hydrogen) produced from renewable biomass resources, i.e. a biomass-derived synthesis gas, and/or methane originating from a landfill gas.

Introduction of PHB-co-4HB pathway genes allows for flexibility in utilizing readily available and inexpensive feedstocks. A "renewable" feedstock refers to a renewable energy source such as material derived from living organisms or their metabolic byproducts including material derived from biomass, often consisting of underutilized components like chaff or stover. Agricultural products specifically grown for use as renewable feedstocks include, for example, corn, soybeans, switchgrass and trees such as poplar, wheat, flaxseed and rapeseed, sugar cane and palm oil. As renewable sources of energy and raw materials, agricultural feedstocks based on crops are the ultimate replacement for declining oil reserves. Plants use solar energy and carbon dioxide fixation to make thousands of complex and functional biochemicals beyond the current capability of modern synthetic chemistry. These include fine and bulk chemicals, pharmaceuticals, nutraceuticals, flavonoids, vitamins, perfumes, polymers, resins, oils, food additives, bio-colorants, adhesives, solvents, and lubricants.

Extraction of PHB-co-4HB Copolymers from Biomass

PHB-co-4HB copolymer was extracted as described in U.S. Pat. Nos. 7,713,720 and 7,252,980.

Molecular Weight Determination using Gel Permeation Chromatography (GPC)

Molecular weight of PHA is estimated by Gel Permeation Chromatography using a Waters Alliance HPLC System equipped with a refractive index detector. The column set is a series of three PLGel 10 μm Mixed-B (Polymer Labs, Amherst, Mass.) columns with chloroform as mobile phase pumped at 1 ml/min. The column set is calibrated with narrow distribution polystyrene standards. The PHA sample is dissolved in chloroform at a concentration of 2.0 mg/ml at 60° C. The sample is filtered with a 0.2 μm Teflon syringe filter. A 50 μ-liter injection volume is used for the analysis. The chromatogram is analyzed with Waters Empower GPC Analysis software. Molecular weights are reported as polystyrene equivalent molecular weights.

Measurement of Thermal Properties

The glass transition of PHB-co-4HB copolymers was measured using a TA Instruments Q100 Differential scanning calorimeter (DSC) with autosampler. 8-12 mg of a PHA sample was carefully weighed into an aluminum pan and sealed with an aluminum lid. The sample was then placed in the DSC under a nitrogen purge and analyzed using a heat-cool-heat cycle. The heating/cooling range was −80° C. to 200° C. with a heating rate of 10° C/min and cooling rate of 5° C./min.

Determination of Biobased Content

The biobased content of the PHB-co-4HB copolymer was measured by radiocarbon dating based on ASTM D6866. ASTM D6866 is the method approved by the U.S. Department of Agriculture for determining the renewable/biobased content of natural range materials. The method provides a percentage determination of fossil carbon content versus renewable or biomass carbon content of a product or fuel blend. ASTM D6866 is used extensively to certify the biobased content of bioplastics.

Example 1: Production of PHB-co-4HB with 50% or Higher 4HB co-monomer Content from Glucose as Sole Carbon Source This example shows PHB-co-4HB production with 50% or higher 4HB co-monomer content from glucose as sole carbon source in engineered E. coli host cells. The strains used in this example are listed in Table 2. All these strains were constructed using the well-known biotechnology tools and methods described above. They all contained chromosomal deletions of yneI and gabD with the exception of strains 31 and 32 which also contained chromosomal deletions of tesB, tesA, yciA, and astD.

TABLE 2

Strains used in Example 1.

| Strains | Operon Configuration |
|---|---|
| 31 | $P_x$-phaC3/C5-$P_{uspA}$-sucD-ssaR, $P_{uspA}$-phaA5-phaB5, $P_{syn1}$-kgdS-$T_{1006}$-$P_{rpsU}$-fucO$_{16L-L71}$-orfZ150, $P_{rpsU}$::orfZ |
| 32 | $P_x$-phaC3/C5-$P_{uspA}$-sucD-ssaR, $P_{uspA}$-phaA5-phaB5, $P_{synAF7}$-kgdS-$T_{1006}$-$P_{rpsU}$-fucO$_{16L-L71}$-orfZ150, $P_{rpsU}$::orfZ |
| 16 | $P_x$-phaC3/C1*-$T_{trpL}$-$P_{uspA}$-phaA5-phaB5-$T_{1006}$-$P_{synH}$-ssaR$_{At}$*-sucD*, $P_{rpsU}$-orfZ |
| 17 | $P_x$-phaC3/C1*-$T_{trpL}$-$P_{uspA}$-phaA5-phaB5-$T_{1006}$-$P_{synA}$-ssaR$_{At}$*-sucD*, $P_{rpsU}$-orfZ |
| 19 | $P_x$-phaC3/C1*-$T_{trpL}$-$P_{uspA}$-phaA5-phaB5-$T_{1006}$-$P_{synM}$-ssaR$_{At}$*-sucD*, $P_{rpsU}$-orfZ |
| 1 | $P_x$-phaC3/C5-$T_{trpL}$-$P_{uspA}$-sucD-ssaR$_{At}$*, $P_{uspA}$-phaA5-phaB5, $P_{rpsU}$-orfZ |
| 20 | $P_x$-phaC3/C1*-$P_{uspA}$-sucD*-ssaR$_{At}$*, $P_{uspA}$-phaA5-phaB5, $P_{rpsU}$-orfZ |
| 33 | $P_x$-phaC3/C5-$P_{uspA}$-sucD-ssaR, $P_{uspA}$-phaA5-phaB5; $P_{synAF3}$-kgdS-$T_{1006}$-$P_{rpsU}$-fucO$_{16L-L71}$-orfZ150, $P_{rpsU}$::orfZ |

The strains were evaluated in a shake plate assay. The production medium consisted of 1×E2 minimal salts, 1×E0 minimal salts, 5 mM MgSO$_4$, and 1×Trace Salts Solution. The carbon source consisted of 40 g/L glucose for strains 31, 32, and 33, whereas for all other strains in Examples 1 to 5, glucose concentration was 20 g/L. 50×E2 stock solution consists of 1.28 M NaNH$_4$HPO$_4$.4H$_2$O, 1.64 M K$_2$HPO$_4$, and 1.36 M KH$_2$PO$_4$. 50×E0 stock solution consists of 1.28 M Na$_2$HPO$_4$, 1.64 M K$_2$HPO$_4$ and 1.36 M KH$_2$PO$_4$. 1000× Trace Salts Solution is prepared by adding per 1 L of 1.5 N HCl: 50 g FeSO$_4$.7H$_2$O, 11 g ZnSO$_4$.7H$_2$O, 2.5 g MnSO$_4$.4H$_2$O, 5 g CuSO$_4$.5H$_2$O, 0.5 g (NH$_4$)$_6$Mo$_7$O$_{24}$.4H$_2$O, 0.1 g Na$_2$B$_4$O$_7$, and 10 g CaCl$_2$.2H$_2$O.

To examine production of PHB-co-4HB, the strains were cultured in triplicate overnight in sterile tubes containing 3 mL of LB and appropriate antibiotics. After culturing was complete, 60 μL, was removed from a tube and then added to 1440 μL of production medium. The resulting 1500 μL cultures were then added to three wells of a Duetz deep-well plate as 500 μL aliquots. The shake plate was incubated at 37° C. with shaking for 6 hours and then shifted to 30° C. for 40 hours with shaking for all strains in Examples 1 to 5, except for strains 31, 32, and 33 which were incubated at 37° C. with shaking for 6 hours and then shifted to 28° C. for 42 hours with shaking. Thereafter, cultures from the three wells were combined (1.5 mL total) and analyzed for polymer content. At the end of the experiment, cultures were spun down at 4150 rpm, washed once with distilled water, frozen at −80° C. for at least 30 minutes, and lyophilized overnight. The next day, a measured amount of lyophilized cell pellet was added to a glass tube, followed by 3 mL of butanolysis reagent that consists of an equal volume mixture of 99.9% n-butanol and 4.0 N HCl in dioxane with 2 mg/mL diphenylmethane as internal standard. After capping the tubes, they were vortexed briefly and placed on a heat block set to 93° C. for six hours with periodic vortexing. Afterwards, the tube was cooled down to room temperature before adding 3 mL distilled water. The tube was vortexed for approximately 10 s before spinning down at 620 rpm (Sorvall Legend RT benchtop centrifuge) for 2 min. 1 mL of the organic phase was pipetted into a GC vial, which was then analyzed by gas chromatography-flame ionization detection (GC-FID) (Hewlett-Packard 5890 Series II). The quantity of PHA in the cell pellet was determined by comparing against standard curves for both 3HB and 4HB (for PHB-co-4HB analysis). The 4HB standard curve was generated by adding different amounts of a 10% solution of γ-butyrolactone (GBL) in butanol to separate butanolysis reactions. The 3HB standard curve was generated by adding different amounts of 99% ethyl 3-hydroxybutyrate to separate butanolysis reactions.

All examinations for PHB-co-4HB production were performed in triplicate as indicated above. Some strains were examined for polymer production in this manner on different days. Representative results for each strain tested are shown in Table 3 and demonstrate that the % 4HB content for each copolymer composition was 50% or higher.

TABLE 3

PHB-co-4HB polymer production from microbial strains.

| Strains | Biomass Titer (g/L) | PHA Titer (g/L) | PHA Composition (% 4HB) |
|---|---|---|---|
| 31 | 6.6 ± 0.3 | 3.7* | 84.6* |
| 32 | 8.1 ± 0.1 | 4.8* | 74.8* |
| 16 | 7.2 ± 0.1 | 4.5 ± 0.0 | 69.7 ± 0.0 |
| 17 | 6.9 ± 0.1 | 4.3 ± 0.1 | 69.4 ± 0.5 |
| 19 | 7.0 ± 0.0 | 4.2 ± 0.1 | 65.8 ± 1.2 |
| 1 | 5.1 ± 0.1 | 2.9 ± 0.0 | 64.5 ± 0.7 |
| 20 | 5.6 ± 0.1 | 3.4 ± 0.1 | 63.9 ± 0.5 |
| 33 | 7.9 ± 0.2 | 3.2* | 50.3* |

*replicate measurements not available

Example 2: Production of PHB-co-4HB with 4HB Co-monomer Content Between 40% and 50% from Glucose as Sole Carbon Source This example shows PHB-co-4HB production with 4HB co-monomer content between 40 and 50% from glucose as sole carbon source in engineered *E. coli* host cells. The strains used in this example are listed in Table 4. All these strains were constructed using the well-known biotechnology tools and methods described above. They all contained chromosomal deletions of yneI and gabD.

TABLE 4

Strains used in Example 2.

| Strains | Operon Configuration |
|---|---|
| 23 | $P_x$-phaC3/C33*-$T_{trpL}$-$P_{uspA}$-phaA5-phaB5-ssaR$_{At}$*-sucD*, $P_{rpsU}$-orfZ |
| 22 | $P_x$-phaC3/C1*-$P_{uspA}$-phaA5-phaB5-ssaR$_{At}$*-sucD*, $P_{rpsU}$-orfZ |
| 21 | $P_x$-phaC3/C1*-$T_{trpL}$-$P_{uspA}$-phaA5-phaB5-$T_{1006}$-$P_{synC}$-ssaR$_{At}$*-sucD*, $P_{rpsU}$-orfZ |
| 2 | $P_x$-phaC3/C5-$T_{trpL}$-$P_{uspA}$-phaA5-phaB5-$T_{1006}$-$P_{synC}$-ssaR$_{At}$*-sucD*, $P_{rpsU}$-orfZ |
| 3 | $P_x$-phaC3/C5-$T_{trpL}$-$P_{uspA}$-phaA5-phaB5-ssaR$_{At}$*-$T_{1006}$-$P_{synH}$-sucD*, $P_{rpsU}$-orfZ |

Strains were grown and polymer content was analyzed in the same manner as described in Example 1. Representative results for each strain tested are shown in Table 5 and demonstrate that the % 4 HB content for each copolymer composition was between 40% and 50%.

TABLE 5

PHB-co-4HB polymer production from microbial strains.

| Strains | Biomass Titer (g/L) | PHA Titer (g/L) | PHA Composition (% 4HB) |
|---|---|---|---|
| 23 | 7.0 ± 0.1 | 4.7 ± 0.2 | 46.0 ± 3.0 |
| 22 | 6.6 ± 0.1 | 4.3 ± 0.1 | 43.6 ± 1.5 |
| 21 | 6.7 ± 0.2 | 4.0 ± 0.3 | 41.6 ± 1.3 |
| 2 | 4.7 ± 0.0 | 2.7 ± 0.1 | 41.5 ± 0.4 |
| 3 | 5.7 ± 0.0 | 3.5 ± 0.0 | 40.4 ± 1.2 |

Example 3 : Production of PHB-co-4HB with 4HB Co-monomer Content Between 30% and 40% from Glucose as Sole Carbon Source This example shows PHB-co-4HB production with 4HB co-monomer content between 30 and 40% from glucose as sole carbon source in engineered *E. coli* host cells. The strains used in this example are listed in Table 6. All these strains were constructed using the well-known biotechnology tools and methods described above. They all contained chromosomal deletions of yneI and gabD.

TABLE 6

Strains used in Example 3.

| Strains | Operon Configuration |
|---|---|
| 26 | $P_{uspA}$-phaC3/C1*-phaA5-phaB5-ssaR$_{At}$*-sucD*, $P_{rpsU}$-orfZ |
| 4 | $P_x$-phaC3/C5-$T_{trpL}$-$P_{uspA}$-phaA5-phaB5-ssaR$_{At}$*-$T_{1006}$-$P_{synM}$-sucD*, $P_{rpsU}$-orfZ |
| 5 | $P_x$-phaC3/C5-$T_{trpL}$-$P_{uspA}$-ssaR$_{At}$*-$P_{syn1}$-phaA5-phaB5-sucD*, $P_{rpsU}$-orfZ |
| 6 | $P_x$-phaC3/C5-$T_{trpL}$-$P_{uspA}$-phaA5-phaB5-$T_{1006}$-ssaR$_{At}$*-sucD*, $P_{rpsU}$-orfZ |
| 7 | $P_x$-phaC3/C5-$T_{trpL}$-$P_{uspA}$-phaA5-phaB5-ssaR$_{At}$*-sucD*, $P_{rpsU}$-orfZ |
| 27 | $P_x$-phaC3/C1*-$T_{trpL}$-$P_{uspA}$-phaA5-phaB5-$T_{1006}$-ssaR$_{At}$*-sucD*, $P_{rpsU}$-orfZ |

Strains were grown and polymer content was analyzed in the same manner as described in Example 1. Representative results for each strain tested are shown in Table 7 and demonstrate that the % 4HB content for each copolymer composition was between 30% and 40%.

TABLE 7

PHB-co-4HB polymer production from microbial strains.

| Strains | Biomass Titer (g/L) | PHA Titer (g/L) | PHA Composition (% 4HB) |
|---|---|---|---|
| 26 | 7.7 ± 0.0 | 5.3 ± 0.1 | 39.3 ± 0.3 |
| 4 | 6.5 ± 0.2 | 4.3 ± 0.1 | 39.2 ± 1.6 |
| 5 | 5.9 ± 0.1 | 4.0 ± 0.2 | 35.9 ± 0.9 |
| 6 | 5.7 ± 0.2 | 2.8 ± 0.0 | 34.6 ± 2.1 |
| 7 | 6.1 ± 0.3 | 3.8 ± 0.1 | 32.2 ± 0.9 |
| 27 | 6.7 ± 0.2 | 4.0 ± 0.1 | 31.7 ± 1.3 |

Example 4 : Production of PHB-co-4HB with 4HB Co-monomer Content Between 20% and 30% from Glucose as Sole Carbon Source This example shows PHB-co-4HB production with 4HB co-monomer content between 20 and 30% from glucose as sole carbon source in engineered *E. coli* host cells. The strains used in this example are listed in Table 8. All these strains were constructed using the well-known biotechnology tools and methods described above. They all contained chromosomal deletions of ynel and gabD.

TABLE 8

Strains used in Example 4.

| Strains | Operon Configuration |
|---|---|
| 8 | $P_x$-phaC3/C5-$T_{trpL}$-$P_{uspA}$-phaA5-phaB5-$T_{1006}$-$P_{synH}$-ssaR$_{At}$*-sucD*, $P_{rpsU}$-orfZ |
| 28 | $P_{syn1}$-phaC1-$P_{uspA}$-sucD*-ssaR$_{At}$*-$P_{syn1}$-phaA5-phaB5, $P_{rpsU}$-orfZ |
| 10 | $P_x$-phaC3/C5-$T_{trpL}$-$P_{uspA}$-sucD*-ssaR$_{At}$*-$P_{syn1}$-phaA5-phaB5, $P_{rpsU}$-orfZ |
| 25 | $P_{uspA}$-phaC3/C1*-sucD*-ssaR$_{At}$*, $P_{syn1}$-phaA5-phaB5, $P_{rpsU}$-orfZ |
| 9 | $P_{uspA}$-phaC3/C5-phaA5-phaB5-ssaR$_{At}$*-sucD*, $P_{rpsU}$-orfZ |
| 11 | $P_x$-phaC3/C5, $T_{trpL}$-$P_{uspA}$-phaA5-phaB5, $P_{rpsU}$-orfZ, sucD*-ssaR$_{At}$* |
| 29 | $P_x$-phaC3/C1*-$T_{trpL}$-$P_{uspA}$-phaA5-phaB5-$T_{1006}$-sucD*-ssaR$_{At}$*, $P_{rpsU}$-orfZ |

Strains were grown and polymer content was analyzed in the same manner described in example 1. Representative results for each strain tested are shown in Table 9 and demonstrate that the % 4HB content for each copolymer composition was between 20% and 30%.

TABLE 9

PHB-co-4HB polymer production from microbial strains.

| Strains | Biomass Titer (g/L) | PHA Titer (g/L) | PHA Composition (% 4HB) |
|---|---|---|---|
| 8 | 4.5 ± 0.1 | 2.2 ± 0.2 | 28.6 ± 2.6 |
| 28 | 5.6 ± 0.1 | 4.4 ± 0.1 | 27.5 ± 0.4 |
| 10 | 6.5 ± 0.0 | 4.3 ± 0.0 | 27.5 ± 0.3 |
| 25 | 6.4 ± 0.0 | 5.2 ± 0.1 | 26.3 ± 0.1 |
| 9 | 6.2 ± 0.0 | 3.9 ± 0.0 | 25.8 ± 0.3 |
| 11 | 5.4 ± 0.2 | 2.4 ± 0.2 | 24.7 ± 2.0 |
| 29 | 5.7 ± 0.2 | 3.0 ± 0.1 | 22.5 ± 0.8 |

Example 5: Production of PHB-co-4HB with 4HB Co-monomer Content Between 1% and 20% from Glucose as Sole Carbon Source This example shows PHB-co-4HB production with 4HB co-monomer content between 1 and 20% from glucose as sole carbon source in engineered *E. coli* host cells. The strains used in this example are listed in Table 10. All these strains were constructed using the well-known biotechnology tools and methods described above. They all contained chromosomal deletions of ynel and gabD.

TABLE 10

Strains used in Example 5.

| Strains | Operon Configuration |
|---|---|
| 13 | $P_x$-phaC3/C5, $T_{trpL}$-$P_{uspA}$-phaA5-phaB5, $P_{rpsU}$-orfZ, sucD*-ssaR$_{At}$* |
| 12 | $P_x$-phaC3/C5-$T_{trpL}$-$P_{uspA}$-phaA5-phaB5-$T_{1006}$-sucD*-ssaR$_{At}$*, $P_{rpsU}$-orfZ |
| 14 | $P_x$-phaC3/C5-$T_{trpL}$-$P_{uspA}$-phaA5-phaB5-ssaR$_{At}$*-$T_{1006}$-sucD*, $P_{rpsU}$-orfZ |
| 30 | $P_x$-phaC3/C1*-$T_{trpL}$-$P_{uspA}$-phaA5-phaB5-ssaR$_{At}$*-$T_{1006}$-sucD*, $P_{rpsU}$-orfZ |
| 15 | $P_x$-phaC3/C5, $T_{trpL}$-$P_{uspA}$-phaA5-phaB5, $P_{rpsU}$-orfZ, sucD*-ssaR$_{At}$* |

Strains were grown and polymer content was analyzed in the same manner described in example 1. Representative results for each strain tested are shown in Table 11 and demonstrate that the % 4HB content for each copolymer composition was between 1% and 20%.

TABLE 11

PHB-co-4HB polymer production from microbial strains.

| Strains | Biomass Titer (g/L) | PHA Titer (g/L) | PHA Composition (% 4HB) |
|---|---|---|---|
| 13 | 5.4 ± 0.1 | 2.4 ± 0.1 | 18.8 ± 0.4 |
| 12 | 6.1 ± 0.1 | 3.2 ± 0.2 | 10.1 ± 0.7 |
| 14 | 5.4 ± 0.1 | 2.5 ± 0.1 | 6.4 ± 0.5 |
| 30 | 4.1 ± 0.2 | 1.7 ± 0.1 | 1.8 ± 0.3 |
| 15 | 4.5 ± 0.1 | 1.4 ± 0.1 | 1.4 ± 0.3 |

Example 6: Extraction of PHB-co-4HB Copolymers and Determination of Molecular Weights and Polydispersity For purification of larger amounts of PHB-co-4HB copolymers, strains 1, 5 and 12 with various PHA compositions as shown in Example 1 were first grown in 20 mL LB medium in 250 mL shake flasks at 37° C. overnight. The entire volume was then transferred into 1 L baffled shake flasks containing 500 mL of a production medium comprised of 1×E2 minimal salts, 1×E0 minimal salts, 5 mM MgSO4, 30 g/L glucose, and 1×Trace Salts Solution. E2 and E0 minimal salts and Trace Salts Solution are described in Example 1. The 500 mL cultures were incubated at 37° C. with shaking for 6 hours and then shifted to 28° C. for 70 hours with shaking. Thereafter, cultures were spun down at 6000×g, washed once with distilled water, frozen at −80° C. for at least 30 minutes, and lyophilized overnight.

The copolymer of strains 1, 5 and 12 were purified from dried biomass by first extracting with cyclo-hexanone at 65-70° C. for 30 min before spinning down at 2000×g for 5 min. Afterwards, the supernatant was decanted and mixed with an equal volume of heptane at 5-10° C. The resulting precipitated polymer was filtered and dried overnight at room temperature.

The molecular weights of the purified copolymers were determined using gel permeation chromatography (GPC) using a Waters Alliance HPLC System. Table 12 shows the weight average molecular weights (Mw), the number average molecular weights (Mn), and the polydispersity index (PD) measured from the copolymers purified from strains 1, 5 and 12.

TABLE 12

Molecular weights and polydispersity of copolymers produced by strains 1, 5 and 12.

| Strains | Mw (g/mole) | Mn (g/mole) | PD |
|---|---|---|---|
| 1 | 950,040 | 537,150 | 1.769 |
| 5 | 1,227,939 | 659,590 | 1.862 |
| 12 | 1,271,813 | 636,416 | 1.998 |

Example 7: Determination of PHA Composition and Glass Transition Temperature of PHB-co-4HB Copolymers The copolymers purified from strains 1, 5 and 12 as described in Example 6 were used to determine the PHA composition as outlined in Example 1. The glass transition temperature (T$_g$) was measured using differential scanning calorimetry (DSC) analysis. Table 13 lists the 4HB content and the T$_g$ measured from the copolymers purified from strains 1, 5 and 12. The glass transition temperature decreased with higher 4HB content in the copolymer.

TABLE 13

PHB-co-4HB polymer production and T$_g$ measured from the copolymers purified from strains 1, 5 and 12.

| Strains | Biomass Titer (g/L) | PHA Titer (g/L) | PHA Composition (% 4HB) | T$_g$ (° C.) |
|---|---|---|---|---|
| 1 | 8.0 | 4.7 | 56 | −25.93 |
| 5 | 10.0 | 6.6 | 33 | −21.32 |
| 12 | 6.8 | 3.9 | 19 | −12.93 |

Example 8: Determination of Biobased Content of a PHB-co-4HB Copolymer

The copolymer purified from strain 1 as described in Example 6 was used to determine the biobased content by radiocarbon dating based on ASTM D6866 by Beta Analytic (Miami, Fla., USA). The purified copolymer from strain 1 was determined to contain a biobased content of 97%.

Example 9: Production of PHB-co-4HB from Glycerol as the Sole Carbon Source

Strains 1 and 6 were grown and polymer content analyzed in the same manner as described in Example 1 with the exception that the carbohydrate fed was 30 g/L glycerol instead of 20 g/L glucose. A representative result for both strains is shown in Table 14.

TABLE 14

PHB-co-4HB polymer production from glycerol as the sole carbon source.

| Strains | Biomass Titer (g/L) | PHA Titer (g/L) | PHA Composition (% 4HB) |
|---|---|---|---|
| 1 | 5.5 ± 0.3 | 2.1 ± 0.1 | 45 ± 3 |
| 6 | 4.8 ± 0.2 | 1.5 ± 0.1 | 18 ± 2 |

```
Gene ID 001 Nucleotide Sequence: Clostridium kluyveri succinate
semialdehyde dehydrogenase gene sucD*
                                                      (SEQ ID NO: 16)
ATGTCCAACGAGGTTAGCATTAAGGAGCTGATTGAGAAGGCGAAAGTGGCGCAGAAAAAGCTGGAAGCGTATA

GCCAAGAGCAAGTTGACGTTCTGGTCAAGGCGCTGGGTAAAGTTGTGTACGACAACGCCGAGATGTTCGCGAA

AGAGGCGGTGGAGGAAACCGAGATGGGTGTTTACGAGGATAAAGTGGCTAAATGTCATCTGAAATCTGGTGCA

ATCTGGAATCACATTAAAGATAAGAAAACCGTTGGTATTATCAAGGAAGAACCGGAGCGTGCGCTGGTGTACG

TCGCGAAGCCTAAAGGTGTTGTGGCGGCGACGACCCCTATCACCAATCCTGTGGTTACCCCGATGTGTAACGC

GATGGCAGCAATTAAAGGTCGCAACACCATCATTGTCGCCCCCGCATCCGAAGGCGAAGAAGGTGAGCGCGCA

CACCGTGGAGCTGATGAATGCAGAACTGAAAAAGTTGGGTGCGCCGGAAAACATTATCCAGATCGTTGAAGCC

CCAAGCCGTGAAGCAGCCAAGGAGTTGATGGAGAGCGCAGACGTGGTTATCGCCACGGGTGGCGCAGGCCGTG

TTAAAGCAGCGTACTCCTCCGGCCGTCCGGCATACGGTGTCGGTCCGGGCAATTCTCAGGTCATTGTCGATAA

GGGTTACGATTATAACAAAGCTGCCCAGGACATCATTACCGGCCGCAAGTATGACAACGGTATCATTTGCAGC

TCTGAGCAGAGCGTGATCGCACCGGCGGAGGACTACGACAAGGTCATCGCGGCTTTCGTCGAGAATGGCGCGT

TCTATGTCGAGGATGAGGAAACTGTGGAGAAATTCCGTAGCACGCTGTTCAAGGATGGCAAGATCAATAGCAA

AATCATCGGTAAATCCGTGCAGATCATCGCTGACCTGGCTGGTGTCAAGGTGCCGGAAGGCACCAAGGTGATC

GTGTTGAAGGGCAAGGGTGCCGGTGAAAAGGACGTTCTGTGCAAGGAGAAAATGTGCCCGGTCCTGGTTGCCC

TGAAATATGACACCTTTGAGGAGGCGGTCGAGATCGCGATGGCCAACTATATGTACGAGGGTGCGGGCCATAC

CGCCGGTATCCACAGCGATAACGACGAGAATATCCGCTACGCGGGTACGGTGCTGCCAATCAGCCGTCTGGTT

GTCAACCAGCCAGCAACTACGGCCGGTGGTAGCTTTAACAATGGTTTTAATCCGACCACCACCTTGGGCTGCG

GTAGCTGGGGCCGTAACTCCATTAGCGAGAACCTGACGTATGAGCATCTGATTAATGTCAGCCGTATTGGCTA

TTTCAATAAGGAGGCAAAAGTTCCTAGCTACGAGGAGATCTGGGGTTAA

Gene ID 001 Amino Acid Sequence: Clostridium kluyveri succinate
semialdehyde dehydrogenase gene SucD*
                                                      (SEQ ID NO: 17)
MSNEVSIKELIEKAKVAQKKLEAYSQEQVDVLVKALGKVVYDNAEMFAKEAVEETEMGVYEDKVAKCHLKSGA

IWNHIKDKKTVGIIKEEPERALVYVAKPKGVVAATTPITNPVVTPMCNAMAAIKGRNTIIVAPHPKAKKVSAH

TVELMNAELKKLGAPENIIQIVEAPSREAAKELMESADVVIATGGAGRVKAAYSSGRPAYGVGPGNSQVIVDK

GYDYNKAAQDIITGRKYDNGIICSSEQSVIAPAEDYDKVIAAFVENGAFYVEDEETVEKFRSTLFKDGKINSK
```

-continued

IIGKSVQIIADLAGVKVPEGTKVIVLKGKGAGEKDVLCKEKMCPVLVALKYDTFEEAVEIAMANYMYEGAGHT

AGIHSDNDENIRYAGTVLPISRLVVNQPATTAGGSFNNGFNPTTTLGCGSWGRNSISENLTYEHLINVSRIGY

FNKEAKVPSYEEIWG

Gene ID 002 Nucleotide Sequence: *Arabidopsis thaliana* succinic
semialdehyde reductase gene ssaR$_{At}$*
(SEQ ID NO: 18)
ATGGAAGTAGGTTTTCTGGGTCTGGGCATTATGGGTAAAGCTATGTCCATGAACCTGCTGAAAAACGGTTTCA

AAGTTACCGTGTGGAACCGCACTCTGTCTAAATGTGATGAACTGGTTGAACACGGTGCAAGCGTGTGCGAGTC

TCCGGCTGAGGTGATCAAGAAATGCAAATACACGATCGCGATGCTGAGCGATCCGTGTGCAGCTCTGTCTGTT

GTTTTCGATAAAGGCGGTGTTCTGGAACAGATCTGCGAGGGTAAGGGCTACATCGACATGTCTACCGTCGACG

CGGAAACTAGCCTGAAAATTAACGAAGCGATCACGGGCAAAGGTGGCCGTTTTGTAGAAGGTCCTGTTAGCGG

TTCCAAAAAGCCGGCAGAAGACGGCCAGCTGATCATCCTGGCAGCAGGCGACAAAGCACTGTTCGAGGAATCC

ATCCCGGCCTTTGATGTACTGGGCAAACGTTCCTTTTATCTGGGTCAGGTGGGTAACGGTGCGAAAATGAAAC

TGATTGTTAACATGATCATGGGTTCTATGATGAACGCGTTTAGCGAAGGTCTGGTACTGGCAGATAAAAGCGG

TCTGTCTAGCGACACGCTGCTGGATATTCTGGATCTGGGTGCTATGACGAATCCGATGTTCAAAGGCAAAGGT

CCGTCCATGACTAAATCCAGCTACCCACCGGCTTTCCCGCTGAAACACCAGCAGAAAGACATGCGTCTGGCTC

TGGCTCTGGGCGACGAAAACGCTGTTAGCATGCCGGTCGCTGCGGCTGCGAACGAAGCCTTCAAGAAAGCCCG

TAGCCTGGGCCTGGGCGATCTGGACTTTTCTGCTGTTATCGAAGCGGTAAAATTCTCTCGTGAATAA

Gene ID 002 Amino Acid Sequence: *Arabidopsis thaliana* succinic
semialdehyde reductase gene SsaR$_{At}$*
(SEQ ID NO: 19)
MEVGFLGLGIMGKAMSMNLLKNGFKVTVWNRTLSKCDELVEHGASVCESPAEVIKKCKYTIAMLSDPCAALSV

VFDKGGVLEQICEGKGYIDMSTVDAETSLKINEAITGKGGRFVEGPVSGSKKPAEDGQLIILAAGDKALFEES

IPAFDVLGKRSFYLGQVGNGAKMKLIVNMIMGSMMNAFSEGLVLADKSGLSSDTLLDILDLGAMTNPMFKGKG

PSMTKSSYPPAFPLKHQQKDMRLALALGDENAVSMPVAAANEAFKKARSLGLGDLDFSAVIEAVKFSRE

Gene ID 003 Nucleotide Sequence: *Escherichia coli* K-12 substr.
MG1655 L-1,2-propanediol oxidoreductase fucO$_{I6L-L7V}$
(SEQ ID NO: 20)
ATGATGGCTAACAGAATGCTGGTGAACGAAACGGCATGGTTTGGTCGGGGTGCTGTTGGGGCTTTAACCGATG

AGGTGAAACGCCGTGGTTATCAGAAGGCGCTGATCGTCACCGATAAAACGCTGGTGCAATGCGGCGTGGTGGC

GAAAGTGACCGATAAGATGGATGCTGCAGGGCTGGCATGGGCGATTTACGACGGCGTAGTGCCCAACCCAACA

ATTACTGTCGTCAAAGAAGGGCTCGGTGTATTCCAGAATAGCGGCGCGGATTACCTGATCGCTATTGGTGGTG

GTTCTCCACAGGATACTTGTAAAGCGATTGGCATTATCAGCAACAACCCGGAGTTTGCCGATGTGCGTAGCCT

GGAAGGGCTTTCCCCGACCAATAAACCCAGTGTACCGATTCTGGCAATTCCTACCACAGCAGGTACTGCGGCA

GAAGTGACCATTAACTACGTGATCACTGACGAAGAGAAACGGCGCAAGTTTGTTTGCGTTGATCCGCATGATA

TCCCGCAGGTGGCGTTTATTGACGCTGACATGATGGATGGTATGCCTCCAGCGCTGAAAGCTGCGACGGGTGT

CGATGCGCTCACTCATGCTATTGAGGGGTATATTACCCGTGGCGCGTGGGCGCTAACCGATGCACTGCACATT

AAAGCGATTGAAATCATTGCTGGGGCGCTGCGAGGATCGGTTGCTGGTGATAAGGATGCCGGAGAAGAAATGG

CGCTCGGGCAGTATGTTGCGGGTATGGGCTTCTCGAATGTTGGGTTAGGGTTGGTGCATGGTATGGCGCATCC

ACTGGGCGCGTTTTATAACACTCCACACGGTGTTGCGAACGCCATCCTGTTACCGCATGTCATGCGTTATAAC

GCTGACTTTACCGGTGAGAAGTACCGCGATATCGCGCGCGTTATGGGCGTGAAAGTGGAAGGTATGAGCCTGG

AAGAGGCGCGTAATGCCGCTGTTGAAGCGGTGTTTGCTCTCAACCGTGATGTCGGTATTCCGCCACATTTGCG

TGATGTTGGTGTACGCAAGGAAGACATTCCGGCACTGGCGCAGGCGGCACTGGATGATGTTTGTACCGGTGGC

AACCCGCGTGAAGCAACGCTTGAGGATATTGTAGAGCTTTACCATACCGCCTGGTAA

Gene ID 003 Amino Acid Sequence: *Escherichia coli* K-12 substr.
MG1655 L-1,2-propanediol oxidoreductase FucO$_{I16L-L7V}$ (SEQ ID NO: 21)

MANRMLVNETAWFGRGAVGALTDEVKRRGYQKALIVTDKTLVQCGVVAKVTDKMDAAGLAWAIYDGVVPNPTI

TVVKEGLGVFQNSGADYLIAIGGGSPQDTCKAIGIISNNPEFADVRSLEGLSPTNKPSVPILAIPTTAGTAAE

VTINYVITDEEKRRKFVCVDPHDIPQVAFIDADMMDGMPPALKAATGVDALTHAIEGYITRGAWALTDALHIK

AIEIIAGALRGSVAGDKDAGEEMALGQYVAGMGFSNVGLGLVHGMAHPLGAFYNTPHGVANAILLPHVMRYNA

DFTGEKYRDIARVMGVKVEGMSLEEARNAAVEAVFALNRDVGIPPHLRDVGVRKEDIPALAQAALDDVCTGGN

PREATLEDIVELYHTAW

Gene ID 004 Nucleotide Sequence: *Pseudomonas putida/Zoogloea ramigera*
polyhydroxyalkanoate synthase fusion gene phaC3/C5

(SEQ ID NO: 22)

ATGAGTAACAAGAACAACGATGAGCTGCAGTGGCAATCCTGGTTCAGCAAGGCGCCCACCACCGAGGCGAACC

CGATGGCCACCATGTTGCAGGATATCGGCGTTGCGCTCAAACCGGAAGCGATGGAGCAGCTGAAAAACGATTA

TCTGCGTGACTTCACCGCGTTGTGGCAGGATTTTTTGGCTGGCAAGGCGCCAGCCGTCAGCGACCGCCGCTTC

AGCTCGGCAGCCTGGCAGGGCAATCCGATGTCGGCCTTCAATGCCGCATCTTACCTGCTCAACGCCAAATTCC

TCAGTGCCATGGTGGAGGCGGTGGACACCGCACCCCAGCAAAAGCAGAAAATACGCTTTGCCGTGCAGCAGGT

GATTGATGCCATGTCGCCCGCGAACTTCCTCGCCACCAACCCGGAAGCGCAGCAAAAACTGATTGAAACCAAG

GGCGAGAGCCTGACGCGTGGCCTGGTCAATATGCTGGGCGATATCAACAAGGGCCATATCTCGCTGTCGGACG

AATCGGCCTTTGAAGTGGGCCGCAACCTGGCCATTACCCCGGGCACCGTGATTTACGAAATCCGCTGTTCCA

GCTGATCCAGTACACGCCGACCACGCCGACGGTCAGCCAGCGCCCGCTGTTGATGGTGCCGCCGTGCATCAAC

AAGTTCTACATCCTCGACCTGCAACCGGAAAATTCGCTGGTGCGCTACGCGGTGGAGCAGGGCAACACCGTGT

TCCTGATCTCGTGGAGCAATCCGGACAAGTCGCTGGCCGGCACCACCTGGGACGACTACGTGGAGCAGGGCGT

GATCGAAGCGATCCGCATCGTCCAGGACGTCAGCGGCCAGGACAAGCTGAACATGTTCGGCTTCTGCGTGGGC

GGCACCATCGTTGCCACCGCACTGGCGGTACTGGCGGCGCGTGGCCAGCACCCGGCGGCCAGCCTGACCCTGC

TGACCACCTTCCTCGACTTCAGCGACACCGGCGTGCTCGACGTCTTCGTCGATGAAACCCAGGTCGCGCTGCG

TGAACAGCAATTGCGCGATGGCGGCCTGATGCCGGGCCGTGACCTGGCCTCGACCTTCTCGAGCCTGCGTCCG

AACGACCTGGTATGGAACTATGTGCAGTCGAACTACCTCAAAGGCAATGAGCCGGCGGCGTTTGACCTGCTGT

TCTGGAATTCGGACAGCACCAATTTGCCGGGCCCGATGTTCTGCTGGTACCTGCGCAACACCTACCTGGAAAA

CAGCCTGAAAGTGCCGGGCAAGCTGACGGTGGCCGGCGAAAAGATCGACCTCGGCCTGATCGACGCCCCGGCC

TTCATCTACGGTTCGCGCGAAGACCACATCGTGCCGTGGATGTCGGCGTACGGTTCGCTCGACATCCTCAACC

AGGGCAAGCCGGGCGCCAACCGCTTCGTGCTGGGCGCGTCCGGCCATATCGCCGGCGTGATCAACTCGGTGGC

CAAGAACAAGCGCAGCTACTGGATCAACGACGGTGGCGCCGCCGATGCCCAGGCCTGGTTCGATGGCGCGCAG

GAAGTGCCGGGCAGCTGGTGGCCGCAATGGGCCGGGTTCCTGACCCAGCATGGCGGCAAGAAGGTCAAGCCCA

AGGCCAAGCCCGGCAACGCCCGCTACACCGCGATCGAGGCGGCGCCCGGCCGTTACGTCAAAGCCAAGGGCTG

A

Gene ID 004 Amino Acid Sequence: *Pseudomonas putiza/Zoogloea ramigera*
polyhydroxyalkanoate synthase fusion gene PhaC3/C5

(SEQ ID NO: 23)

MSNKNNDELQWQSWFSKAPTTEANPMATMLQDIGVALKPEAMEQLKNDYLRDFTALWQDFLAGKAPAVSDRRF

SSAAWQGNPMSAFNAASYLLNAKFLSAMVEAVDTAPQQKQKIRFAVQQVIDAMSPANFLATNPEAQQKLIETK

GESLTRGLVNMLGDINKGHISLSDESAFEVGRNLAITPGTVIYENPLFQLIQYTPTTPTVSQRPLLMVPPCIN

KFYILDLQPENSLVRYAVEQGNTVFLISWSNPDKSLAGTTWDDYVEQGVIEAIRIVQDVSGQDKLNMFGFCVG

GTIVATALAVLAARGQHPAASLTLLTTFLDFSDTGVLDVFVDETQVALREQQLRDGGLMPGRDLASTFSSLRP

NDLVWNYVQSNYLKGNEPAAFDLLFWNSDSTNLPGPMFCWYLRNTYLENSLKVPGKLTVAGEKIDLGLIDAPA

-continued

FIYGSREDHIVPWMSAYGSLDILNQGKPGANRFVLGASGHIAGVINSVAKNKRSYWINDGGAADAQAWFDGAQ

EVPGSWWPQWAGFLTQHGGKKVKPKAKPGNARYTAIEAAPGRYVKAKG

Gene ID 005 Nucleotide Sequence: *Pseudomonas putida/Ralstonia eutropha*
JMP134 polyhydroxyalkanoate synthase fusion gene phaC3/C1*
(SEQ ID NO: 24)

ATGACTAGAAGGAGGTTTCATATGAGTAACAAGAACAACGATGAGCTGGCGACGGGTAAAGGTGCTGCTGCAT

CTTCTACTGAAGGTAAATCTCAGCCGTTTAAATTCCCACCGGGTCCGCTGGACCCGGCCACTTGGCTGGAATG

GAGCCGTCAGTGGCAAGGTCCGGAGGGCAATGGCGGTACCGTGCCGGGTGGCTTTCCGGGTTTCGAAGCGTTC

GCGGCGTCCCCGCTGGCGGGCGTGAAAATCGACCCGGCTCAGCTGGCAGAGATCCAGCAGCGTTATATGCGTG

ATTTCACCGAGCTGTGGCGTGGTCTGGCAGGCGGTGACACCGAGAGCGCTGGCAAACTGCATGACCGTCGCTT

CGCGTCCGAAGCGTGGCACAAAAACGCGCCGTATCGCTATACTGCGGCATTTTACCTGCTGAACGCACGTGCA

CTGACGGAACTGGCTGATGCAGTAGAAGCGGATCCGAAAACCCGTCAGCGTATCCGTTTTGCGGTTTCCCAGT

GGGTAGATGCTATGAGCCCGGCTAACTTCCTGGCCACCAACCCGGACGCTCAGAACCGTCTGATCGAGAGCCG

TGGTGAAAGCCTGCGTGCCGGCATGCGCAATATGCTGGAAGATCTGACCCGCGGTAAAATTTCCCAAACCGAT

GAGACTGCCTTCGAAGTAGGCCGTAACATGGCAGTTACCGAAGGTGCTGTGGTATTCGAAAACGAGTTCTTCC

AGCTGCTGCAGTACAAACCTCTGACTGACAAAGTATACACCCGTCCGCTGCTGCTGGTACCGCCGTGCATTAA

CAAGTTCTATATTCTGGACCTGCAGCCGGAAGGTTCTCTGGTCCGTTACGCAGTCGAACAGGGTCACACTGTA

TTCCTGGTGAGCTGGCGCAATCCAGACGCTAGCATGGCTGGCTGTACCTGGGATGACTATATTGAAAACGCGG

CTATCCGCGCCATCGAGGTTGTGCGTGATATCAGCGGTCAGGACAAGATCAACACCCTGGGCTTTTGTGTTGG

TGGCACGATCATCTCCACTGCCCTGGCGGTCCTGGCCGCCCGTGGTGAGCACCCGGTGGCCTCTCTGACCCTG

CTGACTACCCTGCTGGACTTCACCGATACTGGTATCCTGGATGTTTTCGTGGACGAGCCACACGGTTCAGCTG

CGTGAGGCGACTCTGGGCGGCGCCAGCGGCGGTCTGCTGCGTGGTGTCGAGCTGGCCAATACCTTTTCCTTCC

TGCGCCCGAACGACCTGGTTTGGAACTACGTTGTTGACAACTATCTGAAAGGCAACACCCCGGTACCTTTCGA

TCTGCTGTTCTGGAACGGTGATGCAACCAACCTGCCTGGTCCATGGTACTGTTGGTACCTGCGTCATACTTAC

CTGCAGAACGAACTGAAAGAGCCGGGCAAACTGACCGTGTGTAACGAACCTGTGGACCTGGGCGCGATTAACG

TTCCTACTTACATCTACGTTCCCGTGAAGATCACATCGTACCGTGGACCGCGGCTTACGCCAGCACCGCGCT

GCTGAAGAACGATCTGCGTTTCGTACTGGGCGCATCCGGCCATATCGCAGGTGTGATCAACCCTCCTGCAAAG

AAAAAGCGTTCTCATTGGACCAACGACGCGCTGCCAGAATCCGCGCAGGATTGGCTGGCAGGTGCTGAGGAAC

ACCATGGTTCCTGGTGGCCGGATTGGATGACCTGGCTGGGTAAACAAGCCGGTGCAAAACGTGCAGCTCCAAC

TGAATATGGTAGCAAGCGTTATGCTGCAATCGAGCCAGCGCCAGGCCGTTACGTTAAAGCGAAAGCATAA

Gene ID 005 Amino Acid Sequence: *Pseudomonas putida/Ralstonia eutropha*
polyhydroxyalkanoate synthase fustion gene PhaC3/C1*
(SEQ ID NO: 25)

MSNKNNDELATGKGAAASSTEGKSQPFKFPPGPLDPATWLEWSRQWQGPEGNGGTVPGGFPGFEAFAASPLAG

VKIDPAQLAEIQQRYMRDFTELWRGLAGGDTESAGKLHDRRFASEAWHKNAPYRYTAAFYLLNARLATELADA

VEADPKTRQRIRFAVSQWVDAMSPANFLATNPDAQNRLIESRGESLRAGMRNMLEDLTRGKISQTDETAFEVG

RNMAVTEGAVVFENEFFQLLQYKPLTDKVYTRPLLLVPPCINKFYILDLQPEGSLVRYAVEQGHTVFLVSWRN

PDASMAGCTWDDYIENAAIRAIEVVRDISGQDKINTLGFCVGGTIISTALAVLAARGEHPVASLTLLTTLLDF

TDTGILDVFVDEPHVQLREATLGGASGGLLRGVELANTFSFLRPNDLVWNYVVDNYLKGNTPVPFDLLFWNGD

ATNLPGPWYCWYLRHTYLQNELKEPGKLTVCNEPVDLGAINVPTYIYGSREDHIVPWTAAYASTALLKNDLRF

VLGASGHIAGVINPPAKKKRSHWTNDALPESAQDWLAGAEEHHGSWWPDWMTWLGKQAGAKRAAPTEYGSKRY

AAIEPAPGRYVKAKA

-continued

Gene ID 006 Nucleotide Sequence: *Pseudomonas putida/Delftia acidovorans*
89-11-102 polyhydroxyalkanoate synthase fusion gene phaC3/C33

(SEQ ID NO: 26)

ATGAGTAACAAGAACAACGATGAGCTGGCGAATTTCGACCCGCTGGCTGGCCTGTCTGGTCAATCGGTGCAAC

AGTTCTGGAATGAGCAGTGGAGCCGTACCCTGCAGACCTTGCAGCAGATGGGTCAACCGGGCCTGCCGGGCAT

TCAAGGTATGCCGGGTATGCCAGACATGGCACAAGCGTGGAAAGCCGCTGTGCCGGAACCGGGTGCACTGCCT

GAGAATGCGCTGTCTCTGGATCCGGAGAAGCTGCTGGAACTGCAGCGTCAATATCTGGACGGTGCAAAAGCGA

TGGCAGAGCAGGGCGGTGCGCAAGCATTGCTGGCAAAAGATAAACGTTTCAATACCGAATCGTGGGCAGGTAA

TCCGCTGACGGCTGCGACCGCGGCAACCTACCTGCTGAACTCCCGTATGCTGATGGGTCTGGCGGACGCTGTT

CAGGCGGACGATAAGACCCGTAACCGTGTGCGTTTTGCGATTGAGCAGTGGCTGGCAGCGATGGCGCCGAGCA

ACTTCCTGGCGCTGAATGCTGAGGCCCAAAAGAAGGCGATCGAGACTCAGGGCGAGAGCCTGGCCCAAGGCGT

GGCGAACCTGCTGGCGGATATGCGTCAGGGTCATGTCTCCATGACCGACGAAAGCCTGTTTACGGTGGGCAAG

AACGTGGCAACGACCGAAGGTGCGGTTGTTTTCGAGAATGAGCTGTTCCAGTTGATTGAGTATAAGCCGTTGA

CGGATAAGGTGCATGAGCGCCCGTTCCTGATGGTGCCGCCGTGCATCAACAAATTCTATATCCTGGATCTGCA

ACCGGACAACAGCCTGATCCGTTATGCCGTTAGCCAGGGCCATCGCACGTTCGTCATGTCCTGGCGCAATCCA

GACGAATCTCTGGCCCGTAAAACGTGGGATAACTACATCGAAGATGGCGTTCTGACGGGTATTCGCGTCGCGC

GTGAGATTGCTGGTGCGGAGCAGATCAACGTTCTGGGTTTTTGTGTGGGCGGCACTATGTTGAGCACCGCGTT

GGCGGTTCTGCAAGCCCGCCACGACCGCGAGCACGGCGCAGTCGCAGCACCAGCCGCTAAAGCGCCAGCGGCG

AAACGTGCGGCAGGTAGCCGCAGCGCGGCTCGTACGTCCACTGCGCGTGCCACCGCCCCTGCAGGTGTTCCGT

TCCCGGTTGCGAGCGTCACCTTGCTGACCACCTTTATCGATTTCTCCGACACCGGCATCCTGGACGTGTTCAT

TGATGAATCTGTCGTCCGTTTTCGCGAGATGCAAATGGGTGAAGGTGGTTTGATGAAGGGCAAGACCTGGCG

AGCACCTTTAGCTTTCTGCGCCCGAATGACTTGGTTTGGAATTACGTCGTGGGCAACTACCTGAAAGGTGAAA

CCCCTCCGCCGTTTGACCTGCTGTATTGGAACAGCGATAGCACCAACCTGCCGGGTCCGTACTACGCGTGGTA

CCTGCGTAATCTGTACCTGGAAAATCGCCTGGCACAGCCGGGTGCGTTGACTGTTTGCGGTGAACGTATCGAC

ATGCACCAGCTGCGTCTGCCGGCGTACATCTATGGCAGCCGCGAAGATCACATTGTTCCGGTTGGTGGTAGCT

ATGCCAGCACCCAAGTGCTGGGTGGTGATAAGCGCTTTGTGATGGGTGCGTCCGGTCACATTGCAGGCGTCAT

CAACCCGCCTGCAAAGAAGAAACGTAGCTACTGGCTGCGTGAAGATGGCCAGCTGCCGGCCACGCTGAAAGAG

TGGCAGGCCGGTGCCGACGAGTATCCTGGTAGCTGGTGGGCGGATTGGAGCCCGTGGCTGGCCGAGCACGGTG

GCAAACTGGTGGCAGCGCCGAAGCAATACGGCAAAGGCCGTGAGTACACGGCGATTGAACCGGCTCCAGGCCG

CTACGTTTTGGTCAAGGCGTAA

Gene ID 006 Amino Acid Sequence: *Pseudomonas putida/Delftia acidovorans*
89-11-102 polyhydroxyalkanoate synthase fusion gene phaC3/C33

(SEQ ID NO: 27)

MSNKNNDELANFDPLAGLSGQSVQQFWNEQWSRTLQTLQQMGQPGLPGIQGMPGMPDMAQAWKAAVPEPGALP

ENALSLDPEKLLELQRQYLDGAKAMAEQGGAQALLAKDKRFNTESWAGNPLTAATAATYLLNSRMLMGLADAV

QADDKTRNRVRFAIEQWLAAMAPSNFLALNAEAQKKAIETQGESLAQGVANLLADMRQGHVSMTDESLFTVGK

NVATTEGAVVFENELFQLIEYKPLTDKVHERPFLMVPPCINKFYILDLQPDNSLIRYAVSQGHRTFVMSWRNP

DESLARKTWDNYIEDGVLTGIRVAREIAGAEQINVLGFCVGGTMLSTALAVLQARHDREHGAVAAPAAKAPAA

KRAAGSRSAARTSTARATAPAGVPFPVASVTLLTTFIDFSDTGILDVFIDESVVRFREMQMGEGGLMKGQDLA

STFSFLRPNDLVWNYVVGNYLKGETPPPFDLLYWNSDSTNLPGPYYAWYLRNLYLENRLAQPGALTVCGERID

MHQLRLPAYIYGSREDHIVPVGGSYASTQVLGGDKRFVMGASGHIAGVINPPAKKKRSYWLREDGQLPATLKE

WQADADEYPGSWWADWSPWLAEHGGKLVAAPKQYGKGREYTAIEPAPGRYVLVKA

Those skilled in the art will recognize, or be able to ascertain using no more than routine experimentation, many equivalents to the specific embodiments described herein. Such equivalents are intended to encompassed in the claims that follow.

REFERENCE TO A "SEQUENCE LISTING," A TABLE, OR A COMPUTER PROGRAM LISTING APPENDIX SUBMITTED AS AN ASCII TEXT FILE

The material in the ASCII text file, named "MBLX_50416WO_SequenceListing_ST25.txt", created Sep. 16, 2017, file size of 41,042 bytes, is hereby incorporated by reference.

What is claimed is:

1. A method of making a polyhydroxyalkanoate copolymer composition comprising a plurality of polyhydroxyalkanoate copolymer molecules, wherein the polyhydroxyalkanoate copolymer molecules (i) comprise 3-hydroxybutyrate monomers and 4-hydroxybutyrate monomers, (ii) have a monomeric molar percentage of 4-hydroxybutyrate monomers of 23.5 to 75%, and (iii) have a biobased content of ≥80% corresponding to amount of biobased carbon as a percent of weight (mass) of total organic carbon as defined in ASTM D6866-12, and (iv) have a weight average molecular weight of 250 kDa to 2.0 MDa, and further wherein the composition has a glass transition temperature of −60° C. to −5° C., the method comprising:

culturing an organism in the presence of one or more carbon raw materials under conditions under which (a) the one or more carbon raw materials are converted to 3-hydroxybutyryl-CoA and 4-hydroxybutyryl-CoA and (b) the 3-hydroxybutyryl-CoA and the 4-hydroxybutyryl-CoA are polymerized to form the polyhydroxyalkanoate copolymer molecules, thereby forming the composition, wherein:

the organism has been genetically engineered to comprise enzymatic activities of a polyhydroxyalkanoate synthase, an acetyl-CoA acetyltransferase, an acetoacetyl-CoA reductase, a succinate semialdehyde dehydrogenase, a succinic semialdehyde reductase, and a CoA transferase by stable incorporation of genes encoding the polyhydroxyalkanoate synthase, the acetyl-CoA acetyltransferase, the acetoacetyl-CoA reductase, the succinate semialdehyde dehydrogenase, the succinic semialdehyde reductase, and the CoA transferase into the organism by introduction of one or more stable plasmids comprising the genes and/or by integration of the genes into the genome of the organism, and to not comprise enzymatic activities of either an NAD+-dependent succinate-semialdehyde dehydrogenase or an NADP+-dependent succinate-semialdehyde dehydrogenase or both, and the one or more carbon raw materials, taken together, have a biobased content of ≥80%.

2. The method of claim 1, wherein the organism has further been genetically engineered (a) to comprise enzymatic activities of (i) an alpha-ketoglutarate decarboxylase or 2-oxoglutarate decarboxylase and (ii) an L-1,2-propanediol oxidoreductase, and (b) to not comprise enzymatic activities of one or more of (i) a thioesterase II, (ii) a multifunctional acyl-CoA thioesterase I and protease I and lysophospholipase L, (iii) an acyl-CoA thioesterase, and (iv) an aldehyde dehydrogenase.

3. The method of claim 1, wherein the one or more carbon raw materials comprise a carbon source selected from the group consisting of glucose, levoglucosan, sucrose, lactose, fructose, xylose, maltose, arabinose, and mixtures thereof.

4. The method of claim 1, wherein the one or more carbon raw materials comprise one or more of molasses, starch, a fatty acid, a vegetable oil, a lignocellulosic material, ethanol, acetic acid, glycerol, a biomass-derived synthesis gas, and methane originating from a landfill gas.

5. The method of claim 1, wherein the one or more carbon raw materials do not comprise γ-butyrolactone, 1,4-butanediol, 4-hydroxybutyrate, 3-hydroxybutyrate, α-ketoglutarate, oxaloacetate, malate, fumarate, citrate, succinate, or 3-hydroxybutyrate.

6. The method of claim 1, wherein the one or more carbon raw materials, taken together, have a biobased content of ≥95%.

7. The method of claim 1, wherein the one or more carbon raw materials, taken together, have a biobased content of ≥99%.

8. The method of claim 1, wherein the one or more carbon raw materials, taken together, have a biobased content of 100%.

9. The method of claim 1, wherein the monomeric molar percentage of 4-hydroxybutyrate monomers of the polyhydroxyalkanoate copolymer molecules is 25 to 70%.

10. The method of claim 1, wherein the monomeric molar percentage of 4-hydroxybutyrate monomers of the polyhydroxyalkanoate copolymer molecules is 30 to 40%.

11. The method of claim 1, wherein the monomeric molar percentage of 4-hydroxybutyrate monomers of the polyhydroxyalkanoate copolymer molecules is 40 to 50%.

12. The method of claim 1, wherein the monomeric molar percentage of 4-hydroxybutyrate monomers of the polyhydroxyalkanoate copolymer molecules is 50 to 60%.

13. The method of claim 1, wherein the monomeric molar percentage of 4-hydroxybutyrate monomers of the polyhydroxyalkanoate copolymer molecules is 60 to 70%.

14. The method of claim 1, further comprising isolating the polyhydroxyalkanoate copolymer molecules from the organism, such that the polyhydroxyalkanoate copolymer composition is substantially free of the organism.

* * * * *